(12) United States Patent
Hahn et al.

(10) Patent No.: US 7,662,644 B2
(45) Date of Patent: *Feb. 16, 2010

(54) LABELED PEPTIDES, PROTEINS AND ANTIBODIES AND PROCESSES AND INTERMEDIATES USEFUL FOR THEIR PREPARATION

(75) Inventors: Klaus M. Hahn, San Diego, CA (US); Alexei Toutchkine, San Diego, CA (US); Rajeev Muthyala, Champaign, IL (US); Vadim Kraynov, San Diego, CA (US); Steven J. Bark, San Diego, CA (US); Dennis R. Burton, La Jolla, CA (US); Chester Chamberlain, Cambridge, MA (US)

(73) Assignee: The Scripps Research Institute, La Jolla, CA (US)

( * ) Notice: Subject to any disclaimer, the term of this patent is extended or adjusted under 35 U.S.C. 154(b) by 268 days.

This patent is subject to a terminal disclaimer.

(21) Appl. No.: 11/673,909

(22) Filed: Feb. 12, 2007

(65) Prior Publication Data

US 2007/0218502 A1 Sep. 20, 2007

Related U.S. Application Data

(63) Continuation of application No. 10/455,713, filed on Jun. 3, 2003, now Pat. No. 7,176,037, which is a continuation of application No. PCT/US01/22194, filed on Jul. 13, 2001.

(60) Provisional application No. 60/218,113, filed on Jul. 13, 2000, provisional application No. 60/279,302, filed on Mar. 28, 2001.

(51) Int. Cl.
*G01N 33/533* (2006.01)
*G01N 33/532* (2006.01)
*G01N 33/53* (2006.01)
*C07K 1/10* (2006.01)
*C07D 277/62* (2006.01)

(52) U.S. Cl. .................. 436/546; 436/544; 436/172; 530/391.3; 530/402; 435/7.1; 548/152

(58) Field of Classification Search .................. None
See application file for complete search history.

(56) References Cited

U.S. PATENT DOCUMENTS

| | | |
|---|---|---|
| 3,578,456 A | 5/1971 | Petro et al. |
| 3,764,322 A | 10/1973 | Kampfer et al. |
| 3,810,760 A | 5/1974 | Kampfer al. |
| 3,862,111 A | 1/1975 | Low et al. |
| 4,036,945 A | 7/1977 | Haber |
| 4,331,647 A | 5/1982 | Goldenberg |
| 4,469,768 A | 9/1984 | Hori et al. |
| 4,750,228 A | 6/1988 | Naef |
| 4,816,567 A | 3/1989 | Cabilly et al. |
| 4,994,356 A | 2/1991 | Diehl et al. |
| 5,268,486 A | 12/1993 | Waggoner et al. |
| 5,733,743 A | 3/1998 | Johnson et al. |
| 5,750,373 A | 5/1998 | Garrard et al. |
| 5,814,468 A | 9/1998 | Siiman et al. |
| 5,880,270 A | 3/1999 | Berninger et al. |
| 5,998,204 A | 12/1999 | Tsien et al. |
| 6,001,364 A | 12/1999 | Rose et al. |
| 6,180,295 B1 | 1/2001 | Helber et al. |
| 6,290,957 B1 | 9/2001 | Lowman et al. |
| 6,331,385 B1 | 12/2001 | Deaton et al. |
| 6,461,813 B2 | 10/2002 | Lorens |
| 6,649,421 B1 | 11/2003 | Eigenthaler et al. |
| 6,887,675 B1 | 5/2005 | Luo et al. |
| 7,070,943 B2 | 7/2006 | Darzynkiewicz et al. |
| 2002/0055133 A1 | 5/2002 | Hahn et al. |
| 2002/0094534 A1 | 7/2002 | Greene et al. |
| 2006/0029946 A1 | 2/2006 | Hahn |

FOREIGN PATENT DOCUMENTS

| | | |
|---|---|---|
| EP | 0949269 A1 | 10/1999 |
| EP | 969284 A1 | 1/2000 |
| EP | 0985970 A1 | 3/2000 |
| WO | WO-9640662 A2 | 12/1996 |

(Continued)

OTHER PUBLICATIONS

Maeda et al. Polymethine dye lasers. Opto-electronics 2, 1970, pp. 227-233.*

(Continued)

*Primary Examiner*—Shafiqul Haq
(74) *Attorney, Agent, or Firm*—Schwegman, Lundberg & Woessner, P.A.

(57) ABSTRACT

The invention provides peptide synthons having protected functional groups for attachment of desired moieties (e.g. functional molecules or probes). Also provided are peptide conjugates prepared from such synthons, and synthon and conjugate preparation methods including procedures for identifying optimum probe attachment sites. Biosensors are provided having functional molecules that can locate and bind to specific biomolecules within living cells. Biosensors can detect chemical and physiological changes in those biomolecules as living cells are moving, metabolizing and reacting to its environment. Methods are included for detecting GTP activation of a Rho GTPase protein using polypeptide biosensors. When the biosensor binds GTP-activated Rho GTPase protein, an environmentally sensitive dye emits a signal of a different lifetime, intensity or wavelength than when not bound. New fluorophores whose fluorescence responds to environmental changes are also provided that have improved detection and attachment properties, and that can be used in living cells, or in vitro.

18 Claims, 26 Drawing Sheets

FOREIGN PATENT DOCUMENTS

| | | |
|---|---|---|
| WO | WO-0075105 A1 | 12/2000 |
| WO | WO-0208245 A2 | 1/2002 |
| WO | WO-0228890 A1 | 4/2002 |
| WO | WO-03003666 A1 | 1/2003 |
| WO | WO-03033666 A2 | 4/2003 |
| WO | WO-2005088308 A2 | 9/2005 |

OTHER PUBLICATIONS

"U.S. Appl. No. 11/122,795, Response filed Jul. 31, 2009 to Final Office Action mailed May 1, 2009", 23 pgs.

"U.S. Appl. No. 11/22/795, Non Final Office Action mailed May 5, 2007", 13 pgs.

"U.S. Appl. No. 11/22/795, Non Final Office mailed May 5, 2007", 11 pgs.

"U.S. Appl. No. 11/122,795, Final Office Action mailed Mar. 10, 2008", FOAR, 12.

"U.S. Appl. No. 11/079,907, Amendment and Response filed 3-28-08 to Final Office Action mailed Jan. 28, 2008", 28 pages.

05753652.6, "European Application No. 05753652.6, Office Action Mailed Jul. 14, 2009", 4 pgs.

Etienne-Manneville, Sandrine, "Cdc42—The Centre of Polarity", Journal of Cell Science, 117(8), (2004), 1291-1300.

"U.S. Appl. No. 09/839,577, Non Final Office Action mailed Jul. 7, 2003", 8 pgs.

"U.S. Appl. No. 09/839,577, Non Final Office action mailed Dec. 10, 2003", 20 pgs.

"U.S. Appl. No. 09/839,577, Response filed Jun. 24, 2004 to a Non Final Office Action mailed Dec. 10, 2003", 13 pgs.

"U.S. Appl. No. 09/839,577, Response filed Oct. 7, 2003", 28 pgs.

"U.S. Appl. No. 10/455,713, Non Final Office Action mailed Feb. 6, 2006", 8 pgs.

"U.S. Appl. No. 10/455,713 Notice of Allowance mailed Jul. 26, 2006", 6 pgs.

"U.S. Appl. No. 09/839,577, Notice of Allowance mailed Sep. 8, 2004", 9 pgs.

"U.S. Appl. No. 09/839,577, Non Final Action mailed Feb. 27, 2004", 21 Pgs.

"U.S. Appl. No. 09/839,577, Response filed Oct. 7, 2003 to restiction requirement mailed Jul. 7, 2003", 25 pgs.

"U.S. Appl. No. 10/455,713, Response filed May 8, 2006 to Non Final Office Action mailed Feb. 6, 2006", 16 pgs.

"U.S. Appl. No. 10/455,713, Preliminary Amendment Jun. 3, 2003", 2 pgs.

"U.S. Appl. No. 10/455,713, Response to Non Final Office Action filed May 23, 2005", 13 pgs.

"U.S. Appl. No. 10/455,713, Non Final Office Action mailed Feb. 23, 2005", 5 pgs.

"U.S. Appl. No. 11/079,907, Final Office Action mailed Jan. 28, 2008", 20 pgs.

"U.S. Appl. No. 11/079,907, Notice of Allowance mailed Aug. 11, 2008", NOAR, 10 pgs.

"U.S. Appl. No. 11/079,907, Supplemental Notice Of Allowance Mailed on Oct. 27, 2008", SNOA, 5 Pgs.

"U.S. Appl. No. 11/079,907, Second Supplemental Notice of Allowability mailed on Mar. 18, 2009", 3 pgs.

"U.S. Appl. No. 11/122,795, Amendment and Response filed Jul. 10, 2008 to Final Office Action mailed Mar. 10, 2008", 19 pages.

"U.S. Appl. No. 11/122,795, Final Office Action mailed Mar. 10, 2008", 9 pgs.

"U.S. Appl. No. 11/122,795, Preliminary Amendment filed Aug. 22, 2005", 18 pgs.

"U.S. Appl. No. 11/122,795, Preliminary Amendment filed Sep. 14, 2006", 18 pgs.

"U.S. Appl. No. 11/122,795, Response filed Mar. 30, 2007", 19 pgs.

"U.S. Appl. No. 11/122,795,Final Office Action mailed May 1, 2009", 17 pgs.

"U.S. Appl. No. 11/122,795, Non Final Office Action mailed Mar. 15, 2006", 11 pgs.

"U.S. Appl. No. 11/122,795, Preliminary Amendment filed Sep. 14, 2006", 18 pgs.

"U.S. Appl. No. 11/122,795, Non -Final Office Action mailed Oct. 20, 2008", OARN, 14 pgs.

"U.S. Appl. No. 11/079,907, Amendment filed Nov. 2, 2007 to Non-Final Office Action mailed May 4, 2007", 39 pages.

"Fluorescent Dyes for Flow Cytometry & Microscopy", www.abdirect.com, (2006), 1.

"Fluorochrome data tables", Olympus, http://www.olympusmicro.com/primer/techniques/fluorescence/fluorotable2.html, (2007), 1-6.

"HIV type,groups & subtypes", http://www.avert.org/hivtypes.htm, (Apr. 17, 2007), 1-5.

"International Search Report for corresponding PCT Application No. PCT/US2005/008426", (Nov. 4, 2005), 6 pgs.

"Sulfo-SMCC", Pierce, http://www.piercenet.com/Objects/View.cfm?type=ProductFamily&ID=02030378&Format=Print, (2007), 1.

01954689.4, "European Application No. 01954689.4 ,Office Action Mailed Nov. 4, 2008", 5.

05753652.6, "European Application serial No. 05753652.6 ,Office Action mailed on", 4.

Alzari, P. M, "Three-Dimensional Structure of Antibodies", Annual Review of Immunology, 6, (1988), 555-580.

Bart, J. C., et al., "Environmental Immunoassay for the explosive RDX using a fluorescent dye-labeled antigen and the continuous-flow immunosensor", Sensors and Actuators B,38-39, (1997), 411-418.

Batard, et al., "Use of phycoerythrin and allophycocyanin for fluorescence resonance energy transfer analyzed by flow cytometry: advantages and limitations", Cytometry, vol. 48(2), (2002), 97-105.

Bebbington, C. R., et al., "High-Level Expression of a Recombinant Antibody From Myeloma Cells Using a Glutamine Synthetase Gene as an Amplifiable Selectable Marker", Bio/Technology, 10, (Feb. 1992), 169-175.

Benniston, Andrew C., et al., "Spin-Orbital Coupling Effects on the Photophysical Properties and Photocytotoxicity of Merocyanine Dyes", J. Chem. Soc., Faraday Trans., 93(15), (1997), 2491-2501.

Berridge, Michael J., "Calcium Oscillations", The Journal of Biological Chemistry, 265(17), (1990), 9583-9586.

Binley, James M., et al., "Redox-Triggered Infection by Disulfide-Shackled Human Immunodeficiency Virus Type I Pseudovirions", Journal of Virology, 77(10), (May 2003), 5678-5684.

Bird, R. E., "Single-Chain Antigen-Binding Proteins", Science, 242(4877), (Oct. 21, 1988), 423-426.

Bishop, Anne L., et al., "Rho GTPases and their effector proteins", Biochem. J., 348(Pt. 2), (2000), 241-255.

Boder, Eric T., et al., "Directed Evolution of Antibody Fragments With Monovalent Femtomolar Antigen-Binding Affinity", Proc. Natl. Soc. Sci. USA, 97(20), (Sep. 26, 2000), 10701-10705.

Bright, G. R., et al., "Fluorescence Ratio Imaging Microscopy", Methods in Cell Biology, 30, (1989), 157-192.

Brown, D. J., et al., "The stimulation of pp60v-src kinase activity by vanadate in intact cells accompanies a new phosphorylation state of the enzyme", J Biol Chem., 259(15), (1984), 9580-9586.

Burton, Dennis R., et al., "Human Antibodies From Combinatorial Libraries", Advances in Immunology, 57, (1994), 191-280.

Chamberlain, K. M, et al., "Watching Proteins in the Wild: Fluorescence Methods to Study Protein Dynamics in Living Cells", Traffic, 1(10), (Oct. 2000), 755-762.

Cheng, et al., "Separation distance dependent fluorescence enhancement of fluorescein isothiocyanate by silver nanoparticles", Chem. Commun. (Camb), vol. 21(3), (2007), 21, 248-250.

Chiswell, D. J., "Phage Antibodies: Will New 'Coliclonal' Antibodies Replace Monoclonal Antibodies?", Trends in Biotechnology, 10, (1992), 80-84.

Clackson, Tim, "Making Antibody Fragments Using Phage Display Libraries", Nature, 352(6336), (Aug. 15, 1991), 624-628.

Collis, Abigail V. J., et al., "Analysis of the Antigen Combining Site: Correlations Between Length and Sequence Composition of the Hypervariable Loops and the Nature of an Antigen", Journal of Molecular Biology, 325, (2003), 337-354.

Collman, James P., et al., "Metal Ion Facilitation of Atom-Transfer Oxidation-Reduction Reactions", Journal of the American Chemical Society, 89(18), (Aug. 30, 1967), 4809-4811.

Correa, Paul E., et al., "Selective Autoxidation of Electron-Rich Substrates Under Elevated Oxygen Pressures", J. Org. Chem., 53, (1988), 1695-1702.

Cunningham, B. C., et al., "Production of an Atrial Natriuretic Peptide Variant That is Specific for Type A Receptor", *The EMBO Journal*, 13(11), (1994), 2508-2515.

Cwirla, S. E., et al., "Peptides on Phage: a Vast Library of Peptides for Identifying Ligands", *Proc. Natl. Acad. Sci. USA*, 87(16), (1990), 6378-6382.

Czurylo, et al., "Does Calponin Interact with Caldesmon", *J. Biol. Chem.* vol. 272(51), (1997), 32067-32070.

Del Pozo, Miguel Angel, et al., "Integrins regulate GTP-Rac localized effector interactions through dissociation of Rho-GDI", *Nature Cell Biology*, 4(3), (Mar. 2002), 232-9.

Demas, J. N., et al., "The Measurement of Photoluminescence Quantum Yields. A Review", *The Journal of Physical Chemistry*, 75(8), (Apr. 15, 1971), 991-1024.

Der Maur, Adrian Auf, et al., "Direct in Vivo Screening of Intrabody Libraries Constructed on a Highly Stable Single-Chain Framework", *The Journal of Biological Chemistry*, 277(47), (Nov. 22, 2002), 45075-45085.

Feldhaus, Michael J., et al., "Flow-cytometric isolation of human antibodies from a nonimmune *Saccharomyces cerevisiae* surface display library", *Nature Biotechnology*, 21(2), (Feb. 2003), 163-170.

Flanagan, James H., et al., "Functionalized tricarbocyanine dyes as near-infrared fluorescent probes for biomolecules", *Bioconjugate Chem.*, 8(5), (1997), 751-756.

Foote, Christopher S., et al., "Chemistry of Singlet Oxygen. XIV. A Reactive Intermediate in Sulfide Photooxidation", *Journal of the American Chemical Society*, 93(15), (Jul. 28, 1971), 3795-3796.

Gardiner, Elisabeth M., et al., "Spatial and temporal analysis of Rac activation during live neutrophil chemotaxis", *Current Biology*, 12(23), (Dec. 10, 2002), 2029-2034.

Garofalo, et al., "Ganglioside GM3 activates ERKs in human lymphocytic cells", *Journal of Lipid Research*, vol. 43(6), (2002), 971-978.

Geoghegan, K. F., et al., "Site-directed conjugation of non-peptide groups to peptides and proteins via periodate oxidation of a 2-amino alcohol. Application to modification at N-terminal serine.", *Bioconjugate*, 3(2), (Mar.-Apr. 1992), 138-146.

Glogauer, M., et al., "Introduction of Large Molecules Into Viable Fibroblasts by Electroporation: Optimization of Loading and Identification of Labeled Cellular Compartments", *Experimental Cell Research*, 200(2), (1992), 227-234.

Gok, et al., "Binding of Fluorscein isothiocyanate to Insulin: a fluorimetric labeling study", *J.Fluoresc*,14(2),(2004), 203-206.

Hahn, et al., "A Photocross-linking Fluorescent Indicator of Mitochondrial membrane Potential", The Journal of Histochemistry and Cytochemistry, 41(4), 631-634, 1993.

Hahn, K. M, et al., "A calcium-sensitive fluorescent analog of calmodulin based on a novel calmodulin-binding fluorophore.", *J. Biol. Chem.*, 265(33), (Nov. 25, 1990), 20335-45.

Hahn, Klaus, et al., "Live-Cell Fluorescent Biosensors for Activated Signaling Proteins", *Current Opinion in Cell Biology*, 14, (2002), 167-172.

Hanes, J., et al., "In vitro Selection and Evolution of Functional Proteins by Using Ribosome Display", *Proc. Natl. Acad. Sci. USA*, 94(10), (1997), 4937-4942.

Hanes, Jozef, et al., "Picomolar affinity antibodies from a fully synthetic naive library selected and evolved by ribosome display", *Nature Biotechnology*, 18(12), (Dec. 2000), 1287-1291.

Hawkins, R. E, "Selection of Phage Antibodies by Binding Affinity. Mimicking Affinity Maturation.", *Journal of Molecular Biology*, 254, (1992), 889-896.

Higgs, Henry N., et al., "Activation by Cdc42 and PIP2 of Wiskott-Aldrich Syndrome Protein (WASp) Stimulates Actin Nucleation by Arp2/3 Complex", *The Journal of Cell Biology*, 150(6), (Sep. 18, 2000), 1311-1320.

Hoffman, Gregory R., et al., "Structure of the Rho family GTP-binding protein Cdc42 in complex with the multifunctional regulator RhoGDI", *Cell*, 100(3), (Feb. 4, 2000), 345-356.

Holmes, M. A., et al., "Structural Consequences of Humanizing an Antibody.", *Journal of Immunology*, 158(5), (1997), 2192-2201.

Hoogenboom, H. R., "Building Antibodies From Their Genes", *Immunological Reviews*, 130, (Dec. 1992), 41-68.

Ischenko, A. A., "Structure and Spectral-Luminescent Properties of Polymethine Dyes", *Russian Chemical Reviews*, 60(8), (1991), 865-884.

Iwatani, Shintaro, et al., "Mechanical and chemical properties of cysteine-modified kinesin molecules", *Biochemistry*, 38(32), (Aug. 10, 1999), 10318-10323.

Jobling, Stephen, et al., "Immunomodulation of Enzyme Function in Plants by Single-Domain Antibody Fragments", *Nature Biotechnology*, 21, (Jan. 2003), 77-80.

Johnson, George, et al., "Kabat Database and its Applications: 30 Years After the First Variability Plot", *Nucleic Acids Research*, 28(1), (2000), 214-218.

Jones, P. T., et al., "Replacing the Complementarity-Determining Regions in a Human Antibody With Those From a Mouse", *Nature*, 321(6069), (1986), 522-525.

Jones, T. A., et al., "[10] Electron-Density Map Interpretation", *Methods in Enzymology*, 277(Part B), (1987), 173-208.

Kanony, Claire, et al., "Photobleaching of Asymmetric Cyanines Used for Fluorescence Imaging of Single DNA Molecules", *J. Am. Chem. Soc. 123*, (2001), 7985-7995.

Knappik, Achim, et al., "Fully Synthetic Human Combinatorial Antibody Libraries (HuCAL) Based on Modular Consensus Frameworks and CDRs Randomized With Trinucelotides", *Journal of Molecular Biology*, 296, (2000), 57-86.

Kohler, G., et al., "Continuous Cultures of Fused Cells Secreting Antibody of Predefined Specificity", *Nature. 256*(5517), (Aug. 7, 1975), 495-497.

Kozma, Robert, et al., "The Ras-Related Protein Cdc42Hs and Bradykinin Promote Formation of Peripheral Actin Microspikes and Filopodia in Swiss 3T3 Fibroblasts", *Molecular and Cellular Biology*, 15(4), (Apr. 1995), 1942-1952.

Kwong, Peter D., et al., "Structuree of an HIV gp120 Envelope Glycoprotein in Complex With the CD4 Receptor and a Neutralizing Human Antibody", *Nature. 393*, (Jun. 18, 1998), 648-659.

Larrick, James W, "PCR Amplification of Antibody Genes", *Methods: a Companion to Methods in Enzymology*, 2(2), (1991), 106-110.

Lednev, I. K., et al., "A Raman Spectroscopic study of photochromic benzothiazolium dyes", *Spectrochimica Acta*, 49A(8), (1993), 1055-1063.

Lippincott-Schwartz, Jennifer, et al., "Development and Use of Fluorescent Protein Markers in Living Cells", *Science*, 300, (Apr. 4, 2003), 87-91.

Lippincott-Schwartz, Jennifer, et al., "Studying Protein Dynamics in Living Cells", *Nature Reviews*, 2(6), (Jun. 2001), 444-456.

Lowman, H. B, et al., "Selecting high-affinity binding proteins by monovalent phage display.", *Biochemistry*, 30(45), (Nov. 12, 1991), 10832-8.

Lu, Liangde, et al., "Exciton and Charge-Transfer Interactions in Nonconjugated Merocyanine Dye Dimers: Novel Solvatochromic Behavoir for Tethered Bichromophores and Excimers", *J. Am. Chem. Soc.*, 121, (1999), 8146-8156.

Ludeman, et al., "Structure of a serpin-enzyme complex probed by cysteine substitutions and fluorescence spectroscopy", *Biophys. J.*, vol. 80(1), (2001), 491-497.

Machesky, L. M, et al., "Signaling to actin dynamics", *J Cell Biol.*, 146(2), (Jul. 26, 1999), 267-72.

Machesky, Laura M., et al., "Signaling to Actin Dynamics", *Journal of Cell Biology*, 146(2), (Jul. 26, 1999), 267-272.

Mandel, Debabrata, et al., "Photophysical Processes of Merocyanine 540 in Solutions and in Organized Metals", *J. Phys. Chem. A*, 103, (1999), 8156-8159.

Manning, W. B., et al., "Synthesis of 6-Aminobenzothiazoles from p-Benzoquinone Imine Derivatives", *Synthesis*, 5, (May 1978), 363.

Marks, J. D., "By-passing Immunization. Human Antibodies From V-Gene Libraries Displayed on Phage", *Journal of Molecular Biology*, 222(3), (1991), 581-597.

Marvin, et al., "Engineering Biosensors by Introducing Fluorenscent Allosteric Signal Transducers: Construction of a Novel Glucose Sensor", *J.Am. Chem. Soc.*,120, (1998), 7-11.

McNeil, Paul L., et al., "A Method for Incorporating Macromolecules Into Adherent Cells", *The Journal of Cell Biology*, 98(4), (Apr. 1984), 1556-1564.

McNeil, Paul L., et al., "Glass Beads Load Macromolecules Into Living Cells", *Journal of Cell Science*, 88(Part 5), (Dec. 1987), 669-678.

Miller, Peter J., et al., "Cdc42p GTPase Is Involved in Controlling Polarized Cell Growth in *Schizosaccharomyces pombe*", *Molecular and Cellular Biology*, 14(2), (Feb. 1994), 1075-1083.

Mochizuki, Naoki, et al., "Spatio-Temporal Images of Growth-Factor-Induced Activation of Ras and Rap1", *Nature*, 411, (Jun. 28, 2001), 1065-1068.

Morrison, Sherie L., "Chimeric Human Antibody Molecules: Mouse Antigen-Binding Domains With Human Constant Region Domains", *Proc. Natl. Acad. Sci. USA*, 81(21), (Nov. 1984), 6851-6855.

Moulard, Maxime, et al., "Broadly Cross-Reactive HIV-1-Neutralizing Human Monoclonal Fab Selected for Binding to gp120-CD4-CCR5 Complexes", *Proc. Natl. Acad. Sci. USA*, 99(10), (May 14, 2002), 6913-6918.

Nakahara, Hiroo, et al., "Two-Dimensional Arrangement of Chromophores in J Aggregates of Long-Chain Merocyanines and Its Effect on Energy Transfer in Monolayer Systems", *J. Phys. Chem.*, 90, (1986), 6144-6148.

Nalbant, Perihan, et al., "Activation of Endogenous Cdc42 Visualized in Living Cells", *Science*, 305, (Sep. 10, 2004), 1615-1619.

Narayanan, Narasimhachari, et al., "A New Method for the Synthesis of Heptamethine Cyanine Dyes: Synthesis of New Near-Infrared Fluorescent Labels", *J. Org. Chem.*, 60, (1995), 2391-2395.

Nizak, Clement, et al., "Recombinant Antibodies to the Small GTPase Rab6 as Conformation Sensors", *Science*, 300(5621), (May 9, 2003), 984-987.

Nobes, C. D., "Rho, rac and cdc42 GTPases: Regulators of Actin Structures, Cell Adhesion and Motility", *Biochemical Society Transations*, 23(3), (Aug. 1995), 456-459.

Okada, Craig Y., et al., "Introduction of Macromolecules Into Cultured Mammalian Cells by Osmotic Lysis of Pinocytic Vesicles", *Cell*, 29(1), (May 1982), 33-41.

Onganer, Yavuz, et al., "Dynamical Solvation Effects on the Cis-Trans Isomerization Reaction: Photoisomerization of Merocyanine 540 in Polar Solvents", *J. Phys. Chem.*, 97, (1993), 2344-2354.

Pack, P., et al., "Improved Bivalent Miniantibodies, With Identical Avidity as Whole Antibodies, Produced by High Cell Density Fermentation of *Escherichia coli.*", *Bio/Technology*, 11(11), (1993), 1271-1277.

Park, Ro Dong, et al., "Hypertonic Sucrose Inhibition of Endocytic Transport Suggests Multiple Early Endocytic Compartments", *Journal of Cellular Physiology*, 135(3), (1988), 443-450.

Parmley, S. F., et al., "Antibody-Selectable Filamentous fd Phage Vectors: Affinity Purification of Target Genes", *Gene*, 73(2), (1988), 305-318.

Pestic-Dragovich, Lidija, et al., "A Myosin I Isoform in the Nucleus", *Science*, 290(5490), (Oct. 13, 2000), 337-341.

Post, Penny L., et al., "A Genetically Engineered, Protein-based Optical Biosensor of Myosin II Regulatory Light Chain Phosphorylation", *J. Biol. Chem.*, (1994), 12880-12887.

Prendergast, et al., "Systhesis, spectral properties, and use of 6-acryloyl-2-dimethylaminonapthalene (Acrylodan)", *A thiol-selective, polarity-sensitive fluorescent probe. J. Bio.L Chem.*, 258(12), (1983), 7541-7544.

Presta, L. G, "Antibody Engineering", *Current Opinion in Structural Biology*, 3(4), (1992), 593-596.

Proba, Karl, et al., "Antibody scFv Fragments Without Disulfide Bonds Made by Molecular Evolution", *Journal of Molecular Biology*, 275, (1998), 245-253.

Rader, Christoph, et al., "Phage Display of Combinatorial Antibody Libraries", *Current Opinion in Biotechnology*, 8(4), (Aug. 1997), 503-508.

Regitz, Manfred, "Reaktionen aktiver Methylenverbindungen mit Aziden, V—Uber ein a-Diazo-b-keto-sulfon", *Chemische Berichte*, 98(1), (1965), 36-45.

Renard, M., et al., "Deriving Topological Constraints From Functional Data for the Design of Reagentless Fluorescent Immunosensors", *J. Mol. Biol.*, 326(1), (2003), 167-175.

Renard, Martial, et al., "Knowledge-Based Design of Reagentless Fluorescent Biosensors From Recombinant Antibodies", *J. Mol. Biol.*, 318(2), (2002), 429-442.

Riechmann, L., et al., "Reshaping Human Antibodies for Therapy.", *Nature*, 332(6162), (1988), 323-327.

Russell, Stephen J., "Retroviral Vectors Displaying Functional Antibody Fragments", *Nucleic Acids Research*, 21(5), (1993), 1081-1085.

Saphire, Erica O., et al., "Crystal Structure of a Neutralizing Human IgC Against HIV-1: A Template for Vaccine Design", *Science*, 293, (Aug. 10, 2001), 1155-1159.

Schaffitzel, Christine, et al., "Ribosome Display: An in vitro Method for Selection and Evolution of Antibodies From Libraries", *Journal of Immunological Methods*, 231, (1999), 119-135.

Schneckenburger, H., et al., "Laser-assisted optoporation of single cells", *Journal of Biomedical Optics*, 7(3), (Jul. 2002), 410-416.

Scott, J. K., "Discovering Peptide Ligands Using Epitope Libraries", *Trends in Biochemical Sciences*, 17(7), (1992), 241-245.

Seth, Abhinav, et al., "Rational Design of Genetically Encoded Fluorescence Resonance Energy Transfer-Based Sensors of Cellular Cdc42 Signalling", *Biochemistry*, 42(14), (Apr. 15, 2003), 3997-4008.

Sloan, David J., et al., "Structure-Based Engineering of Environmentally Sensitive Flurophores for Monitoring Protein-Protein Interactions", *Protein Engineering*, 11(9), (1998), 819-823.

Soper, Steven A., et al., "Steady-State and Picosecond Laser Fluorescence Studies of Nonradiative Pathways in Tricarbocyanin Dyes: Implications to the Design of Near-IR Fluorochromes With High Fluorescence Efficiencies", *Journal of the American Chemical Society*, 116, (1994), 3744-3752.

Soughayer, Joseph S., et al., "Characterization of Cellular Optoporation With Distance", *Analytical Chemistry*, 72(6), (Mar. 15, 2000), 1342-1347.

Subauste, M. C., et al., "A Catalytic Antibody Produces Fluorescent Tracers of Gap Junction Communication in Living Cells", *The Journal of Biological Chemistry*, 276(52), (2001), 49164-49168.

Tanakka, Tomoyuki, et al., "De novo Production of Diverse Intracellular Antibody Libraries", *Nucleic Acids Research*, 31(5)(e23), (2003), 10 pgs.

Tansey, et al., "Ca(2+) dependent phosphorylation of mtosin light chain kinase decreases the Ca2+ sensitivity of light chain phosphorylation within smooth muscle cells", *J. Boil. Chem.*, 269(13), (1994), 9912-9920.

Teruel, Mary N., et al., "A Versatile Microporation Technique for the Transfection of Cultured CNS Neurons", *Journal of Neuroscience Methods*, 93, (1999), 37-48.

Teruel, Mary N., et al., "Parallel Single-Cell Monitoring of Receptor-Triggered Membrane Translocation of a Calcium-Sensing Protein Module", *Science*, 295, (Mar. 8, 2002), 1910-1912.

Ting, Alice Y., et al., "Genetically Encoded Fluorescent Reporters of Protein Tyrosine Kinase Activities of Living Cells", *Proc. Natl. Acad. Sci. USA*, 98(26), (Dec. 18, 2001), 15003-15008.

Toomre, Derek, et al., "Lighting Up the Cell Surface With Evanescent Wave Microscopy", *Trends in Cell Biology*, 11(7), (Jul. 2001), 298-303.

Torchilin, Vladimir P., et al., "Cell Transfection in vitro and in vivo With Nontoxic TAT Peptide-Liposome-DNA Complexes", *Proc. Natl. Acad. Sci. USA*, 100(4), (Feb. 18, 2003), 1972-1977.

Toutchkine, A., et al., "Solvent-sensitive dyes to report protein conformational changes in living cells", *Journal of the American Chemical Society,American Chemical Society*,Washington,DC,US,vol. 125(14), (Apr. 9, 2003), 4132-4145.

Trinkaus-Randall, V., et al., "Role of Calcium and Calmodulin in Hemidesmosome Formation In Vitro", *The Journal of Cell Biology*, 98, (Apr. 1984), 1565-1571.

Tse, Eric, et al., "Intracellular Antibody-Caspase-Mediated Cell Killing: An Approach for Application in Cancer Therapy", *Proc. Natl. Acad. Sci. USA*, 97(22), (Oct. 24, 2000), 12266-12271.

Turro, Nicholas J., "The Role of Intersystem Crossing Steps in Singlet Oxygen Chemistry and Photo-Oxidations", *Tetrahedron*, 41(11), (1985), 2089-2098.

Valdes-Aguilera, Oscar, et al., "Aggregation Phenomena in Xanthene Dyes", *Acc. Chem. Res.*, 22, (1989), 171-177.

Vaswani, S. K., "Humanized Antibodies as Potential Therapeutic Drugs", *Annals of Allergy, Asthma, & Immunology*, 81(2), (1998), 105-119.

Verveer, Peter J., et al., "Quantitative Imaging of Lateral ErbB1 Receptor Signal Propagation in the Plasma Membrane", *Science*, 290(5496), (2000), 1567-1570.

Vignal, Emmanuel, et al., "Characterization of TCL, a New GTPase of the Pho Family Related to TC10 and Cdc42", *The Journal of Biological Chemistry*, 275(46), (2000), 36457-36464.

Vilaseca, L. A., et al., "Protein conjugates of defined structure: synthesis and use of a new carrier molecule", *Bioconjugate Chem.*,4(6), (Nov.-Dec. 1993), 515-520.

Visintin, Michela, et al., "The Intracellular Antibody Capture Technology (IACT): Towards a Consensus Sequence for Intracellular Antibodies", *Journal of Molecular Biology*, 317, (2002), 73-83.

Watanabe, Yasumasa, et al., "Persulfoxide and Thiadioxirane Intermediates in the Reaction of Sulfides and Singlet Oxygen", *Journal of American Chemical Society*, 113, (1991), 2677-2682.

Whitlow, Marc, et al., "Single-Chain Fv Proteins and Their Fusion Proteins", *Methods: a Companion to Methods in Enzymology*, 2(2), (1991), 97-105.

Wilder, et al., "Recognition of the tumor suppressor protein p53 and other protein targets by the calcium-binding protein S100B", *Biochim, Biophys. Acta.*, vol. 1763(11), (2006), 1284-1297.

Wilk, et al., "Evolution of a light-harvesting protein by addition of new subunits and rearrangement of conserved elements: Crystal structure of a cryptophyte phycoerythrin at 1.63-Å? resolution", *Proc. Natl. Acad. Sci.* USA, vol. 96 (16), 8901-8906.

Williams, David A., et al., "Calcium Gradients in Single Smooth Muscle Cells Revealed by the Digital Imaging Microscope Using Fura-2", *Nature*, 318(6046), (Dec. 12, 1985), 558-561.

Winter, Greg, et al., "Making Antibodies by Phage Display Technology", *Annual Review of Immunology*, 12, (1994), 433-455.

Wouters, Fred S., et al., "Imaging Biochemistry Inside Cells", *Trends in Cell Biology*, 11(5), (May 2001), 203-211.

Wurthner, Frank, et al., "Dipolar Dye Aggregates: A Problem for Nonlinear Optics, but a Chance for Supramolecular Chemistry", *Angew. Chem. Int. Ed.*, 39(11), (2000), 1978-1981.

Yang, Yonghui, et al., "HIV-1 TAT-Mediated Protein Transduction and Subcellular Localization Using Novel Expression Vectors", *FEBS Letters*, 532, (2002), 36-44.

Zaccolo, Manuela, et al., "A Genetically Encoded, Fluorescent Indicator for Cyclic AMP in Living Cells", *Nature Cell Biology*, 2(1), (Jan. 2000), 25-29.

Zelphati, Olivier, et al., "Intracellular Delivery of Proteins With a New Lipid-Mediated Delivery System", *The Journal of Biological Chemistry*, 276(37), (2001), 35103-35110.

Zhang, Jin, et al., "Genetically Encoded Reporters of Protein Kinase A Activity Reveal Impact of Substrate Testing", *Proc. Natl. Acad. Sci.* USA, 98(26), (Dec. 18, 2001), 14997-15002.

Zombeck, Alan, et al., "Novel Catalytic Oxidations of Terminal Olefins by Cobalt(II)-Schiff Base Complexes", *Journal of the American Chemical Society*, 104, (1982), 6782-6784.

Abdul-Manan, Norzehan, et al., "Structure of Cdc42 in Complex With the GTPase-binding Domain of the 'Wiskott-Aldrich Syndrome' Protein.", *Nature*, 399(6734), (1999),379-83.

Adamczyk, M., et al., "A Chemoselective Method for Site-Specific Immobilization of Peptides via Aminooxy Group", *Bioconjugate Chemistry*, 12, (Feb. 28, 2001), 139-142.

Adams, S R., et al., "Fluorescence ratio imaging of cyclic AMP in single cells", *Nature.* 349(6311), (1991),694-7.

Anderson, G. W., et al., "The Use of Esters of N-Hydroxysuccinimide in Peptide Synthesis", *Journal of the American Chemical Society*, 86, (1964),1839-1842.

Bark, Steven J., et al., "A Highly Efficient Method for Site-Specific Modification of Unprotected Peptides After Chemical Synthesis", *Journal of American Chemical Society*, 122(15), (Apr. 19, 2000),3567-3573.

Benard, V , et al., "Characterization of rac and cdc42 activation in chemoattractant-stimulated human neutrophils using a novel assay for active GTPases", *Journal of Biological Chemistry*, 274(19), (1999),13198-204.

Brinkley, Michael , "A brief survey of methods for preparing protein conjugates with dyes, haptens, and cross-linking reagents", *Bioconjugate Chemistry.* 3(1), (1992),2-13.

Bryan, D. B., et al., "Nuclear Analogues of B-Lactam Antibiotics. 2. The Total Synthesis of 8-Oxo-4-thia-1-azabicyclo[4.2.0]oct-2-ene-2-carboxylic Acids", (1977),2353-2355.

Canne, L E., "Extending the Applicability of Native Chemical Ligation", *Journal of the American Chemical Society*, 118, (1996),5891-5896.

Canne, L. E., "Total Chemical Synthesis of a Unique Transcription Factor-Related Protein: cMyc-Max", *J. Am. Chem. Soc.*, 117, (1995),2998-3007.

Carroll, B. H., "Supersensitization with Merocyanine Dyes", Abstract Only, Caplus Database, Document No. 51:70442,(1957),2 p.

Cervigni, S. E., et al., "Synthesis of Glycopeptides and Lipopeptides by Chemoselective Ligation", *Angew. Chem. Int. Ed. Engl.*, 35, (1996),1230-1232.

Cervigni, Stefano E., et al., "Synthesis of Glycopeptides and Lipopeptides by Chemselective Ligation", *Angew. Chem. Int. Ed. Engl.*, 35(11), (Jun. 17, 1996),1230-1232.

Chamberlain, C. E., et al., "[35] Imaging Spatiotemporal Dynamics of Rac Activation in Vivo with FLAIR", *Methods of Enzymology*, 325, (2000),389-400.

Chamberlain, C. , et al., "Watching Proteins in the Wild: Fluorescence Methods to Study Protein Dynamics in Living Cells", *Traffic*, 1, (2000),755-762.

Chung, C Y., "Role of Rac in controlling the actin cytoskeleton and chemotaxis in motile cells", *Proceedings of the National Academy of Sciences of the United States of America.* 97(10), (2000),5225-30.

Cornish, V W., et al., "Site-Specific Protein Modification Using a Ketone", *Journal of the American Chemical Society*, 118, (1996),8150-8151.

Cotton, G J., et al., "Insertion of a Synthetic Peptide into a Recombinant Protein Framework: A Protein Biosensor", *Journal of the American Chemical Society*, 121, (1999),1100-1101.

Dawson, P. E., "Synthesis of Proteins by Native Chemical Ligation", *Science*, 266, (1994),pp. 776-779.

Day, R N., "Visualization of Pit-1 transcription factor interactions in the living cell nucleus by fluorescence resonance energy transfer microscopy.", *Molecular Endocrinology.* 12(9), (1998),1410-9.

Deaton, J. C., et al., "Photographic Material Having Enhanced Light Absorption", Abstract Only, Caplus Database, Document No. 132:229435,(2000),2 p.

Debiasio, R. , et al., "Five-Parameter Fluorescence Imaging: Wound Healing of Living Swiss 3T3 Cells", *The Journal of Cell Biology*, 105, (1987),1613-1622.

Dharmawardhane, S. , et al., "Localization of p21-Activated Kinase 1 (PAK1) to Pseudopodia, Membrane Ruffles, and Phagocytic Cups in Activated Human Neutrophils", *Journal of Leukocyte Biology*, 66, (1999),521-527.

Diehl, D. R., et al., "Solid Particle Dispersions of Filter Dyes for Photographic Elements", Abstract Only, Caplus Database, Document No. 116:48759,(1992),2 p.

Ely, C M., et al., "A 42-kD tyrosine kinase substrate linked to chromaffin cell secretion exhibits an associated MAP kinase activity and is highly related to a 42-kD mitogen-stimulated protein in fibrobla", *Journal of Cell Biology.* 110(3), (1990),731-42.

Evans, Jr., T. C., et al., "Semisynthesis of Cytotoxic Proteins Using a Modified Protein Splicing Element", *Protein Science*, 7, (1998),2256-2264.

Gaertner, H. F., et al., "Site-Specific Attachment of Functionalized Poly(ethylene glycol) to the Amino Terminus of Proteins", *Bioconiugate Chem.* 7, (1996),38-44.

Giuliano, K A., et al., "Fluorescent protein biosensors: measurement of molecular dynamics in living cells.", *Annual Review of Biophysics & Biomolecular Structure.* 24:, (1995),405-34.

Gonzalez, F A., et al., "Heterogeneous expression of four MAP kinase isoforms in human tissues", *FEBS Letters.* 304(2-3), (1992),170-8.

Griffin, B A., et al., "Specific covalent labeling of recombinant protein molecules inside live cells", *Science*, 281(5374), (Jul. 10, 1998),269-72.

Hackeng, T. M., et al., "Chemical Synthesis and Spontaneous Folding of a Multidomain Protein: Anticoagulant Microprotein S", *Proc. Natl. Acad. Sci.* USA, 97(26), (2000),14074-14078.

Hahn, K M., et al., "A calcium-sensitive fluorescent analog of calmodulin based on a novel calmodulin-binding fluorophore", *Journal of Biological Chemistry*, 265(33), (Nov. 25, 1990), 20335-45.

Hahn, K , et al., "Patterns of elevated free calcium and calmodulin activation in living cells", *Nature.* 359(6397), (1992),736-8.

Hall, A, "Rho GTPases and the actin cytoskeleton", *Science.* 279(5350), (1998),509-14.

Hawkins, P T., et al., "PDGF stimulates an increase in GTP-Rac via activation of phosphoinositide 3-kinase", *Current Biology*, 5(4), (1995),393-403.

Helber, M. J., et al., "Liquid-crystalline Filter Dye for Imaging element", Abstract Only, Caplus Database, Document No. 132:229438,(2400),2 p.

Hojo, H. , et al., "Development of a Linker With an Enhanced Stability for the Preparation of Peptide Thioesters and Its Application to the Synthesis of a Stable-Isotoope-Labelled HU-Type DNA-Binding Protein", *Bulletin of the Chemical Society of Japan*, 66(9), (1993),2700-2706.

Horie, S. , et al., "Electrophotographic Light-sensitive Material", Abstract Only, Caplus Database, Document No. 98:188999,(1983),1 p.

Itoh, Reina E., et al., "Activation of Rac and Cdc42 Video Imaged by Fluorescent Resonance Energy Transfer-Based Single-Molecule Probes in the Membrane of Living Cells", *Molecular and Cellular Biology*, 22(18), (2002),6582-6591.

Jencks, W. P., et al., "General Base Catalysis of the Aminolysis of Phenyl Acetate", *Journal of American Chemical Society*, 82, (1960),675-681.

Jencks, W. P., "The Reaction of Hydroxylamine With Activated Acyl Groups. II. Mechanism of the Reaction", *Journal of the American Chemical Society*, 80, (1958),4585-4588.

Joneson, T , et al., "Suppression of Ras-induced apoptosis by the Rac GTPase", *Molecular & Cellular Biology*, 19(9), (1999),5892-901.

Kaiser, E , et al., "Color test for detection of free terminal amino groups in the solid-phase synthesis of peptides", *Analytical Biochemistry.* 34(2), (1970),595-8.

Kampfer, H. , et al., "Dry Photocopy Process", Abstract Only, Caplus Database, Document No. 77:68574,(1972),1 p.

Kampfer, H. , et al., "Photographic Dry-copying Process", Abstract Only, Caplus Database, Document No. 77:65233,(1973),1 p.

Katz, B Z., et al., "Green fluorescent protein labeling of cytoskeletal structures—novel targeting approach based on leucine zippers", *Biotechniques.* 25(2), (1998),298-302.

Kent, S. B., "Chemical Synthesis of Peptides and Proteins", *Ann. Rev. Biochem.*, 57, (1988),957-989.

Kim, Annette S., et al., "Autoinhibition and Activation Mechanisms of the Wiskott-Aldrich Syndrome protein", *Nature*, 404(6774), (Mar. 9, 2000),151-158.

King, T P., et al., "Preparation of protein conjugates via intermolecular hydrazone linkage", *Biochemistry*, 25(19), (1986),5774-9.

Kjoller, L , et al., "Signaling to Rho GTPases", *Experimental Cell Research*, 253(1), (1999),166-79.

Knaus, U G., "Purification and Characterization of Rac 2. A Cytosolic GTP-Binding Protein that Regulates Human Neutrophil NADPH Oxidase", *Journal of Biological Chemistry*, 267(33), (Nov. 25, 1992),23575-23582.

Kraynov, Vadim S., et al., "Localized Rac Activation Dynamics Visualized in Living Cells", *Science*, 290(5490), (Oct. 13, 2000),333-336.

Lelievre, D. , et al., "Simple and Efficient Solid-Phase Synthesis of Unprotected Peptide Aldehyde for Peptide Segment Ligation", *Tetrahedron Letters*, 39, (1998),9675-9678.

Leonard, D A., et al., "Use of a fluorescence spectroscopic readout to characterize the interactions of Cdc42Hs with its target/effector, mPAK-3", *Biochemistry.* 36(5), (1997),1173-80.

Manser, E , et al., "A brain serine/threonine protein kinase activated by Cdc42 and Rac1", *Nature.* 367(6458), (1994),40-46.

Marcaurelle, L A., et al., "Direct incorporation of unprotected ketone groups into peptides during solid-phase synthesis: Application to the one-step modification of peptides with two different biophysical probes for FRET", *Tetrahedron Letters.* 39(40), (1998),7279-7282.

Matsuyama, J. , et al., "Sensitization of photographic silver halide emulsions to electron beams", Abstract Only, Caplus Database, Document No. 77:12280,(1972),1 p.

Mckee, T. , et al., "Biochemistry, Molecular Basis of Life", *McGraw-Hill*, (2003),108,133,135.

Menard, L , et al., "Rac1, a low-molecular-mass GTP-binding-protein with high intrinsic GTPase activity and distinct biochemical properties", *European Journal of Biochemistry.* 206(2), (1992),537-46.

Michiels, F , et al., "A role for Rac in Tiam1-induced membrane ruffling and invasion", *Nature.* 375(6529), (1995),338-40.

Miyasaka, T , et al., "Nerve growth factor stimulates a protein kinase in PC-12 cells that phosphorylates microtubule-associated protein-2", *Journal of Biological Chemistry.* 265(8), (1990),4730-5.

Miyawaki, A , et al., "Fluorescent indicators for Ca2+ based on green fluorescent proteins and calmodulin", *Nature.* 388(6645), (1997),882-7.

Motorina, I. A., at al., "Selective O-Allylation of Amidoalcohols on Solid Support", *Synlett—Accounts and Rapid Communications in Synthetic Organic Chemistry*, 4, (1996),389-391.

Muir, T. W., "Expressed Protein Ligation: A General Method for Protein Engineering" *PNAS USA*, 95, (Jun. 1998),6705-6710.

Mujumdar, Ratnakar B., et al., "Cyanine Dye Labeling Reagents Containing Isothiocyanate Groups", *Cytometry*, 10(1), (1989),11-19.

Naef, R. , "Disperse Dyes", Abstract Only, Caplus Database, Document No. 109:39399,(1988),2 p.

Nel, A E., et al., "Stimulation of Map-2 kinase activity in T lymphocytes by anti-CD3 or anti-Ti monoclonal antibody is partially dependent on protein kinase C", *Journal of Immunology.* 144(7), (1990),2683-9.

NG, T , et al., "Imaging protein kinase Calpha activation in cells", *Science*, 283(5410), (1999),2085-9.

Nobes, C D., et al., "Rho GTPases control polarity, protrusion, and adhesion during cell movement", *Journal of Cell Biology.* 144(6), (1999),1235-44.

Nomanbhoy, T K., et al., "Investigation of the GTP-binding/GTPase cycle of Cdc42Hs using extrinsic reporter group fluorescence", *Biochemistry.* 35(14), (1996),4602-8.

Nyberg, D. D., et al., "The Synthesis of DL-Canaline, DL-Canavanine and Related Compounds", *Journal of American Chemical Society*, 79, (1957),1222-1226.

OI, Vernon T., et al., "Chimeric Antibodies", *BioTechniques*, 4(3), (1986),214-21.

Perler, F. B., et al., "Protein Splicing and its Applications", *Current Opinion in Biotechnology*, 11, (2000),377-383.

Petro, V. P., et al., "Silver-free Photosensitive Compounds", Abstract Only, Caplus Database, Document No. 72:116794,(1970),1 p.

Pokrovskaya, K. I., et al., "Study of Interaction between Merocyanines and Silver Ions in Solution", Abstract Only, Caplus Database, Document No. 55:142216,(1960),4 p.

Pollok, B. A., "Using GFP in FRET-based applications", *Trends Cell Biol.*, 9, (1999),57.

Quinlan, M. P., et al., "Establishment of the Circumferential Actin Filament Network is a Prerequisite for Localization of the Cadherin-Catenin Complex of Epithelial Cells", *Cell Growth & Differentiation*, 10, (1999),839-854.

Rabinowitch, Eugene , et al., "Polymerization of dyestuffs in solution. Thionine and methylene blue.", *Journal of the American Chemical Society*, 63, (1941),69-78.

Ray, L B., et al., "Rapid stimulation by insulin of a serine/threonine kinase in 3T3-L1 adipocytes that phosphorylates microtubule-associated protein 2 in vitro", *Proceedings of the National Academy of Sciences of the United States of America.* 84(6), (1987),1502-6.

Renard, Martial , et al., "Knowledge-Based Design of Reagentless Fluorescent Biosensors from Recombinant Antibodies", *Journal of Molecular Biology*, 318, (2002),429-442.

Richieri, G V., et al., "The measurement of free fatty acid concentration with the fluorescent probe ADIFAB: a practical guide for the use of the ADIFAB probe", *Molecular & Cellular Biochemistry*, 192(1-2), (1999),87-94.

Ridley, A J., et al., "The small GTP-binding protein rac regulates growth factor-induced membrane ruffling", *Cell.* 70(3), (1992),401-10.

Rose, K, "Facile Synthesis of Homogeneous Artificial Proteins", *Journal of the American Chemcial Society*, 116., (1994),30-33.

Rose, K, et al., "Natural peptides as building blocks for the synthesis of large protein-like molecules with hydrazone and oxime linkages", *Bioconiugate Chemistry.* 7(5), (1996),552-6.

Schnolzer, M , et al., "In situ neutralization in Boc-chemistry solid phase peptide synthesis. Rapid, high yield assembly of difficult sequences", *International Journal of Peptide & Protein Research*, 40(3-4), (1992),180-93.

Severin, K , et al., "A synthetic peptide ligase", *Nature, 389*(6652), (1997),706-9.

Shiba, K. , et al., "Photographic Silver Halide Emulsion", Abstract Only, Caplus Database, Document No. 74:36922,(1971),1 p.

Subauste, M C., et al., "Rho family proteins modulate rapid apoptosis induced by cytotoxic T lymphocytes and Fas", *Journal of Biological Chemistry.* 275(13), (Mar. 31, 2000),9725-33.

Sun, Lee K., et al., "Chimeric antibodies with 171A-derived variable and human constant regions", *Hybridoma*, 5(Supp 1), (1986),S17-S20.

Terpetschnig, E , et al., "Synthesis of squaraine-N-hydroxysuccinimide esters and their biological application as long-wavelength fluorescent labels", *Analytical Biochemistry.* 217(2), (1994),197-204.

Theriot, J A., et al., "Actin microfilament dynamics in locomoting cells", *Nature. 352*(6331), (1991),126-31.

Thompson, G , et al., "Delineation of the Cdc42/Rac-binding domain of p21-activated kinase", *Biochemistry.* 37(21), (1998),7885-91.

Troung, K. , et al., "The use of FRET imaging microscopy to detect protein-protein interactions and protein conformational changes in vivo", *Current opinion in structural biology*, (2001),573-578.

Tsien, Roger Y., "The Green Fluorescent Protein", *Annu. Rev. Biochem.*, 67, (1998),509-544.

Van Dormael, A. , et al., "Electronic Structure of Trinuclear Cyanines", Abstract Only, Caplus Database, Document No. 54:26887,(1958),1 p.

Wahl, F , et al., "Analogues of oxytocin with an oxime bridge using chemoselectively addressable building blocks", *Tetrahedron Letters. 37*(38), (1996),6861-6864.

Wang, Y L., "Exchange of actin subunits at the leading edge of living fibroblasts: possible role of treadmilling", *Journal of Cell Biology. 101*(2), (1985),597-602.

Weiner, O D., et al., "Spatial control of actin polymerization during neutrophil chemotaxis", *Nature Cell Biology. 1*(2), (1999),75-81.

West, W , et al., "The dimeric state of cyanine dyes", *The Journal of Physical Chemistry*, 69(6), (1965),1894-1903.

Whish, W. J., et al., "Studies on the aminoxyalanine methyl ester and its alphaN-acetyl derivative", *Canadian Journal of Biochemistry*, 48(4), (Apr. 1970),520-522.

Whish, W. J., et al., "Studies on the Aminoxyalanine Methyl Ester and Its alpha-N-acetyl Derivative", *Canadian Journal of Biochemistry*, 48, (1970),520-522.

Wilken, J , et al., "Chemical protein synthesis", *Current Opinion in Biotechnology. 9*(4), (1998),412-26.

Yang, T T., et al., "Dual color microscopic imagery of cells expressing the green fluorescent protein and a red-shifted variant" *Gene. 173*(1 Spec No), (1996),19-23.

Zhang, W. , et al., "A Chemically Modified Green-Fluorescent Protein that Responds to cleavage of an Engineered Disulphide Bond by Fluorescence Resonance Enger Transfer (FRET)-Based Changes", *Chemistry Letters*, 34 (6), (2005),766-767.

Zhang, Jin , "Creating New Fluorescent Probes for Cell Biology", *Nature Reviews*, 3(12), This reference is not a relevant prior art because it does not disclose key aspects of the claimed invention. RAC Dec. 5, 2006,(Dec. 2002),906-918.

Zhou, K , et al., "Guanine nucleotide exchange factors regulate specificity of downstream signaling from Rac and Cdc42", *Journal of Biological Chemistry.* 273(27), (Jul. 3, 1998),16782-6.

* cited by examiner

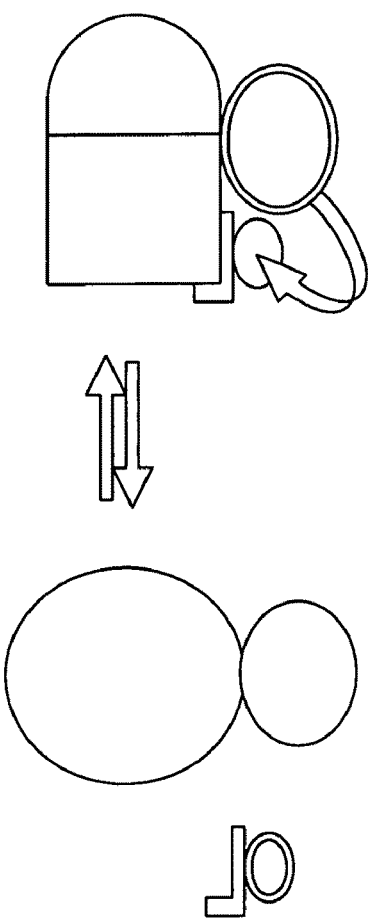
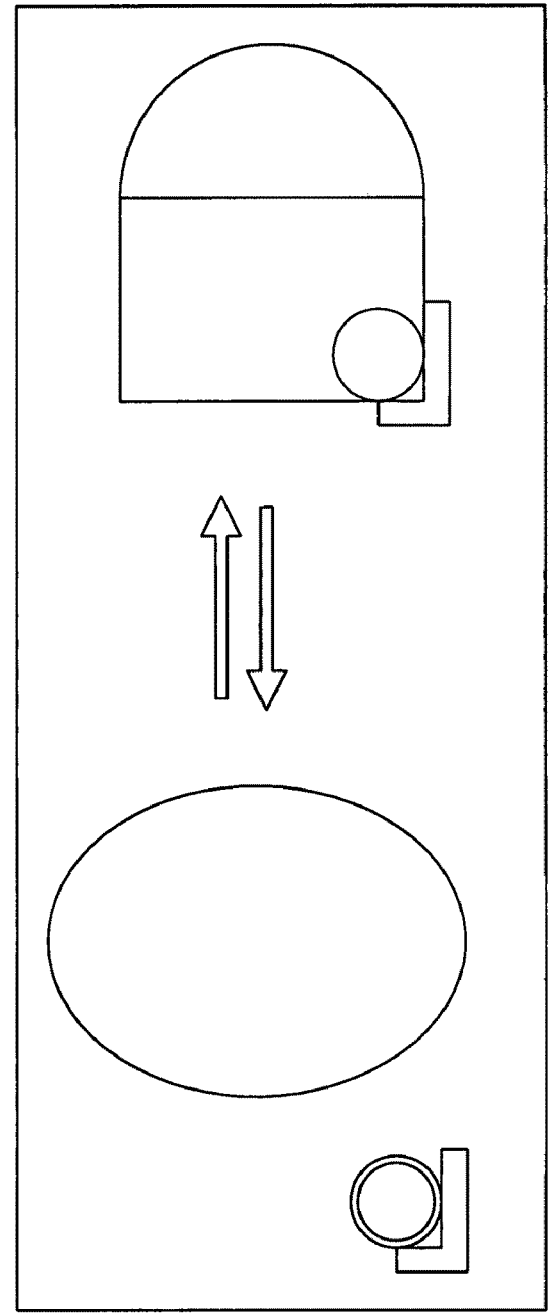
FIG. 6A
FIG. 6B

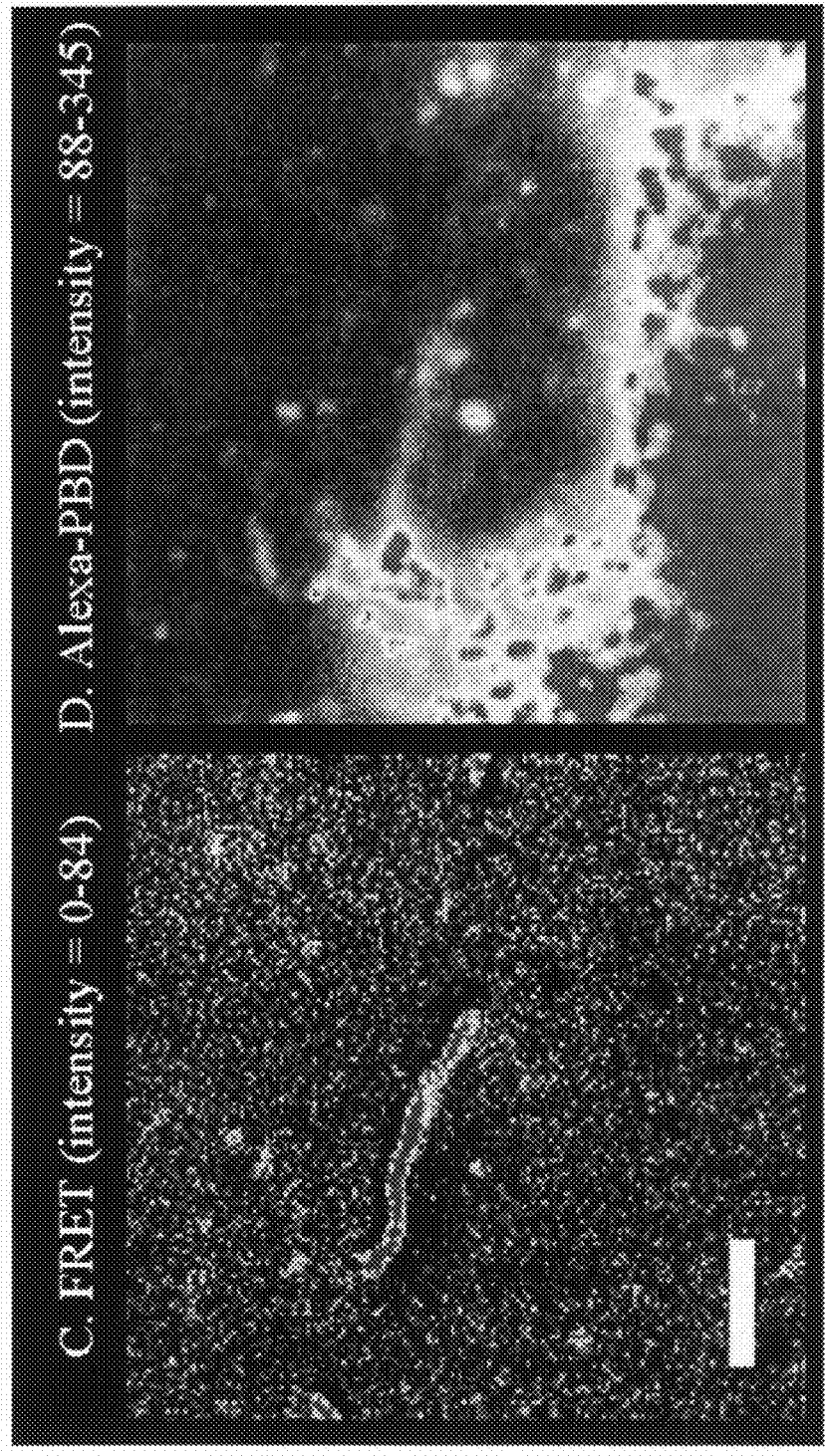

Fig. 10A: Rac-GFP
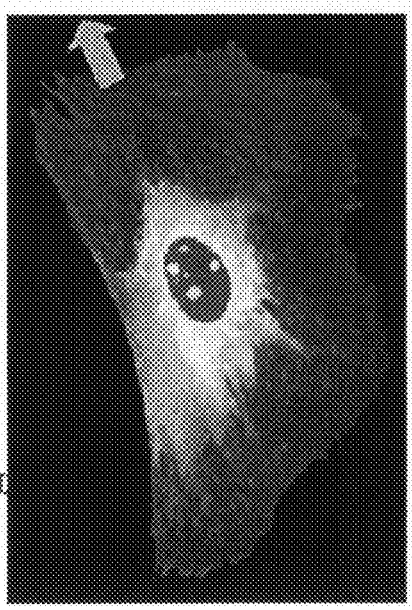
Fig. 10B. FRET
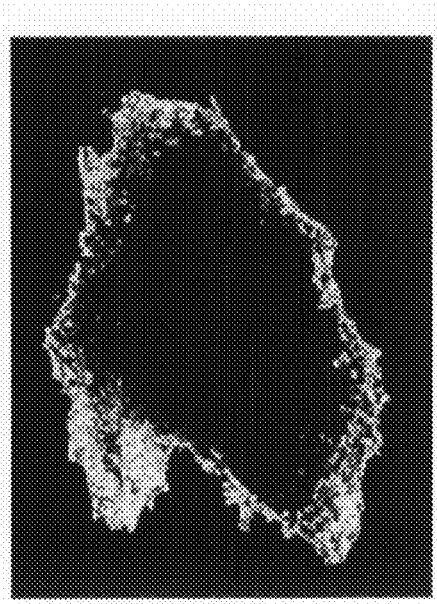
Wound healing
Confluent monolayer
Magnitude of gradient when highest at front  128 +/- 51 %  n=12
Magnitude of gradient highest at rear  9 +/- 4 %  n=4

LABELED PEPTIDES, PROTEINS AND ANTIBODIES AND PROCESSES AND INTERMEDIATES USEFUL FOR THEIR PREPARATION

RELATED APPLICATIONS

This application is a continuation under 37 C.F.R. 1.53(b) of U.S. application Ser. No. 10/455,713 filed Jun. 3, 2003 now U.S. Pat. No. 7,176,037, which is a continuation of International Application No. PCT/US20010/22194 filed on Jul. 13, 2001, which claimed priority under 35 U.S.C. 119 of U.S. application Ser. No. 09/839,577 filed Apr. 20, 2001, U.S. Provisional Application Ser. No. 60/279,302 filed Mar. 28, 2001, PCT/US2000/026821 filed Sep. 29, 2000, and U.S. Provisional Application Ser. No. 60/218,113 filed Jul. 13, 2000, which applications are incorporated herein by reference.

GOVERNMENT FUNDING

The invention described herein was made with United States Government support under Grant Number MCB-9812248 awarded by the National Science Foundation, and under Grant Numbers CA58689, AG15430 and GM 57464 awarded by the National Institutes of Health. The United States Government has certain rights in this invention.

BACKGROUND OF THE INVENTION

Modified peptides and proteins are valuable biophysical tools for studying biological processes, both in vitro and in vivo. They are also useful in assays to identify new drugs and therapeutic agents. In particular, quantitative live cell imaging using fluorescent proteins and peptides is revolutionizing the study of cell biology. An exciting recent development within this field has been the construction of peptide and protein biosensors exhibiting altered fluorescence properties in response to changes in their environment, oligomeric state, conformation upon ligand binding, structure, or direct ligand binding. Appropriately labeled fluorescent biomolecules allow spatial and temporal detection of biochemical reactions inside living cells. See for example Giuliano, K. A., et al., *Annu. Rev. Biophys. Biomol. Struct.* 1995, 24:405-434; Day, R. N., *Mol. Endocrinol.* 1998, 12:1410-9; Adams, S. R., et al., *Nature* 1991, 349:694; Miyawaski, A., et al., *Nature* 1997, 388:882-7; Hahn, K., et al., *Nature* 1992, 359:736; Hahn, K. M., et al., *J. Biol. Chem.* 1990, 265:20335; and Richieri, G. V., et al., *Mol. Cell. Biochem.* 1999, 192:87-94.

Procedures for site-specific modification of polypeptides have been described, including: chemically selective labeling in solution (Brinkley, M. *Bioconjugate Chemistry* 1992, 3:2-13) and on resin bound peptides (Hackeng, T., et al., *J. Biol. Chem.* Submitted); introduction of ketone amino acids through synthetic procedures (Rose, K. *J. Am. Chem. Soc.* 1994, 116:30-33; King, T. P., et al., *Biochemistry*, 1986, 25:5774-5779; Rose, K., et al., *Bioconjugate Chem.* 1996, 7:552-556; Marcaurelle, L. A., Bertozzi, C. R. *Tett. Lett.* 1998, 39:7279-7282; and Wahl, F., Mutter, M. *Tett. Lett.* 1996, 37:6861-6864; and molecular biology techniques (Cornish, V. W., et al., *J. Am. Chem. Soc.* 1996, 118:8150). For example, green fluorescence protein (GFP) is a fluorescent protein that has been fused to other proteins using molecular biology techniques and has been used to visualize intracellular proteins (see, e.g., Katz et al., *BioTechniques* 25: 298-304 (1998)).

While each of these methods has utility for producing a particular class of biosensor or labeled polypeptide, all have limitations that restrict their general use. Labeling of natural amino acid side-chains in solution is often impractical because of the existence of many other competing nucleophiles. Additionally, the use of unnatural amino acids, such as those bearing ketones for selective labeling, requires the synthesis of dye constructs or amino acids that are difficult to make and are not available commercially. While a variety of proteins have been fused to GFP, some GFP-labeled proteins fail to fluoresce. Mutational analysis indicates that the structure of GFP is extremely sensitive to molecular or biochemical modifications. Moreover, GFP is extremely large (238 amino acids). Hence, fusion of GFP to other proteins can alter the function of GFP or even the function of the protein to which it is fused. Moreover, GFP does not have the diverse capabilities of smaller, synthetic molecules, some of which provide a variety of fluorescence wavelengths, or are capable of reporting on protein conformation, or can photo-crosslink or act as NME or EPR probes. Accordingly, new fluorescent molecules with more diverse properties and new attachment methods are needed.

Currently, the major obstacles to the development of fluorescent biosensors and labeled polypeptides remain: (1) The difficulty in site-specific placement of the dye in the polypeptide and (2) determining exactly which site is optimal for dye placement (Giuliano, K. A., et al., *Annu. Rev. Biophys. Biomol. Struct.* 1995, 24:405-434). Solvent-sensitive dyes and other biophysical probes must be placed precisely for optimal response to changes in protein structure without interference with biological activity. Also, the need for site-specific incorporation of two dyes without impairment of biological activity has proven a serious limitation for utilization of fluorescence resonance energy transfer (FRET) within a single protein. Total chemical synthesis of proteins provides a potential solution to these problems (Wilken, J., Kent, S. B. H. *Curr. Op. Biotechnology.* 1998, 9:412; Kent, S. B. H. *Ann. Rev. Biochem.* 1988, 57, 957-989; Dawson, P. E., et al., *Science* 1994, 266:776-779; Muir, T. W., et al., *Proc. Natl. Acad. Sci.* 1998, 95:6705-6710; and Cotton, G. J., et al., *J. Am. Chem. Soc.* 1999, 121:1100-1101). However, many biophysical probes suitable for fluorescent biosensors or other purposes are not stable to the various conditions used for peptide synthesis, and site-specific incorporation after synthesis has been difficult to achieve.

Moreover, labeling with hydrophobic dyes such as thionine or methylene blue can be problematic because these dyes autoaggregate in aqueous solution at high concentration. See, *J. Am. Chem. Soc.* 63, 69 (1941). These aggregates cause a change in the absorption spectrum and a reduction in the fluorescence of the dyes. Cyanines and merocyanines are also thought to aggregate, causing a quenching of fluorescence (*J. Phys. Chem.* 69, 1894 (1965)). Such aggregation interferes with conjugation of these fluorescent dyes to other molecules such as proteins. Moreover aggregation by cyanines and merocyanines can be exacerbated after the dyes are conjugated. For example, Waggoner et al. have observed an aggregation phenomenon following the conjugation of cyanin isothiocyanate with an antibody (*Cytometry* 10, 11-19 (1989)). Fluorescence of a conjugate between a cyanin fluorescent dye and an anti-HCG antibody (molar ratio=1.7) named CY5.18 is quenched in comparison with that of the free cyanin (see U.S. Pat. No. 5,268,486 and Anal. Biochem. 217, 197-204 (1994)). Also, while cyanines are generally stable, inexpensive, simple to conjugate to other molecules and of a suitable size for the recognition of small molecules, they do not change their fluorescence in response to environmental factors, such as solvent polarity. New dyes that eliminate these problems are needed.

Thus, there is currently a need for new fluorescent dyes and peptide synthons having protected functional groups that can be selectively modified to incorporate one or more functional molecules (e.g. a fluorescent label) following peptide synthesis. There is also a need for proteins and antibodies with biophysical probes attached to precise locations, and for simple, non-destructive methods of making such labeled proteins and antibodies. Simpler methods for using these labeled peptides, proteins and antibodies in vivo as biosensors are also needed.

SUMMARY OF THE INVENTION

The present invention provides a highly efficient method for the site-specific attachment of biophysical probes or other molecules to unprotected peptides following chemical synthesis. The methodology utilizes amino acids having one or more protected aminooxy groups, which can be incorporated during solid-phase peptide synthesis or which can be combined with recombinant peptides through post expression steps. It has been discovered that the protected aminooxy group can be unmasked following peptide synthesis, and reacted with an electrophilic reagent to provide a modified (e.g. a labeled) peptide. The aminooxy group reacts selectively with electrophiles (e.g. an activated carboxylic ester such as an N-hydroxy-succinimide ester) in the presence of other nucleophilic groups including cysteine, lysine and amino groups.

Thus, selective peptide modification (e.g. labeling) can be accomplished after synthesis using commercially available and/or chemically sensitive molecules (e.g. probes). The methodology is compatible with the synthesis of $C^\alpha$-thioester containing peptides and amide-forming ligations, required steps for the synthesis of proteins by either total chemical synthesis or expressed protein ligation. An aminooxy containing amino acid can be introduced into different sites by parallel peptide synthesis to generate a polypeptide analogue family with each member possessing a single specifically-labeled site. The parallel synthesis enables the development of optimized biosensors or other modified polypeptides through combinatorial screening of different attachment sites for maximal response and minimal perturbation of desired biological activity.

Thus, a simple and efficient methodology for site-specific modification (e.g. labeling) of peptides after synthesis has been developed that provides high yield, selectivity, and compatibility with both solid-phase peptide synthesis and $C^\alpha$-thioester peptide recombinant synthesis.

Accordingly, the invention provides a synthetic intermediate (i.e. a synthon) useful for preparing modified peptides, which is a compound of formula (I):

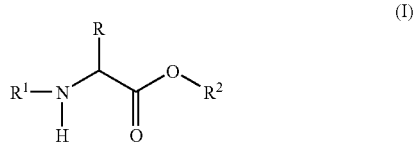

wherein:
$R^1$ is hydrogen or an amino protecting group;
$R^2$ is hydrogen or a carboxy protecting group;

R is an organic radical comprising one or more aminooxy groups.

Peptides including one or more aminooxy groups are also useful synthetic intermediates that can be modified to provide related peptides having altered biological, chemical, or physical properties, such as, for example, a peptide linked to a fluorescent label. Accordingly, the invention also provides a peptide having one or more (e.g. 1, 2, 3, or 4) aminooxy groups; provided the peptide is not glutathione. The invention also provides a peptide having one or more (e.g. 1, 2, 3, or 4) secondary aminooxy groups.

The invention generally provides intermediates and methods that allow for site-specific modification of peptides after synthesis. Accordingly, functional molecules can be selectively linked to a peptide to provide a peptide conjugate having altered biological, chemical, or physical properties. For example, functional molecules (e.g. biophysical probes, peptides, polynucleotides, and therapeutic agents) can be linked to a peptide to provide a peptide conjugate having differing and useful properties.

Thus, the invention also provides a compound of formula (III):

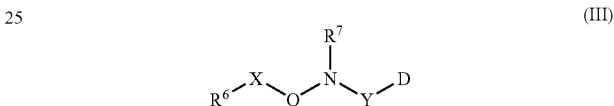

wherein:
$R^6$ is a peptide, polypeptide or antibody;
X is a direct bond or a linking group;
$R^7$ is hydrogen, $(C_1$-$C_6)$alkyl, an amino protecting group, or a radical comprising one or more aminooxy groups;
Y is a direct bond or a linking group; and
D is a functional molecule.

A functional molecule can be any label, dye, pharmaceutical, toxin, Preferably the functional molecule is a biophysical probe, such as a fluorescent group that can be used for FRET studies or other studies involving fluorescent signals, such as excimer pair formation.

Processes for preparing synthons of the invention as well as the polypeptide, antibody and protein conjugates of the invention are provided as further embodiments of the invention and are illustrated by the procedures in the Examples below.

Thus, the invention also provides a method for preparing a peptide conjugate comprising a peptide and a functional molecule, comprising reacting a peptide having one or more aminooxy groups with a corresponding functional molecule having an electrophilic moiety, to provide the peptide conjugate.

The present invention further provides environment-sensing dyes that can be readily conjugated to proteins and other molecules without the problems of aggregation, fluorescence quenching and the like. The present dyes strongly fluoresce and can fluoresce in an environmentally-sensitive manner suitable for use in living cells. Unlike cyanine dyes, the environmental sensitivity of these dyes can be used to form biosensors that can report many aspects of protein behavior, or the behavior of other molecules. Protein behaviors including conformational change, phosphorylation state, ligand interaction, protein-protein binding and various post-translational modifications affect the distribution of charged and hydrophobic residues can be reported by the present dyes by changes in their fluorescence.

The present invention overcomes the disadvantages of the available environmentally-sensitive fluorescent dyes. The present fluorescent probes exhibit high fluorescence levels before and after conjugation to other molecules, including peptides, proteins and antibodies, and changes in fluorescence suitable for many purposes, including in vivo and in vitro assays of protein behavior.

The present invention provides new fluorescent dyes that can be used in any manner chosen by one of skill in the art. The dyes can be linked to any useful molecule known to one of skill in the art using any available procedure. In one embodiment the fluorescent dyes are linked to peptides, polypeptides or antibodies using the methods provided herein. These dyes have the following structure (IV).

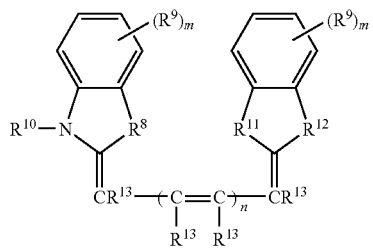

wherein:
each m is separately an integer ranging from 1-3;
n is an integer ranging from 0 to 5;
$R^8$, $R^{11}$ and $R^{12}$ are separately CO, $SO_2$, C=$C(CN)_2$, S, O or $C(CH_3)_2$;
each $R^{13}$ is alkyl, branched alkyl or heterocyclic ring derivatized with charged groups to enhance water solubility and enhance photostability;
$R^9$ and $R^{10}$ are chains carrying charged groups to enhance water solubility (i.e. sulfonate, amide, ether) and/or chains bearing reactive groups for conjugation to other molecules. The reactive group is a functional group that is chemically reactive (or that can be made chemically reactive) with functional groups typically found in biological materials, or functional groups that can be readily converted to chemically reactive derivatives using methods well known in the art. In one embodiment of the invention, the charged and reactive groups are separately haloacetamide (—NH—(C=O)—$CH_2$—X), where X is Cl, Br or I. Alternatively, the charged and reactive groups are separately amine, maleimide, isocyanato (—N=C=O), isothiocyanato(—N=C=S), acyl halide, succinimidyl ester, or sulfosuccinimidyl ester. In another embodiment, the charged and reactive groups are carboxylic acid (COOH), or derivatives of a carboxylic acid. An appropriate derivative of a carboxylic acid includes an alkali or alkaline earth metal salt of carboxylic acid. Alternatively, the charged and reactive groups are reactive derivatives of a carboxylic acid (—COORx), where the reactive group Rx is one that activates the carbonyl group of —COORx toward nucleophilic displacement. In particular, Rx is any group that activates the carbonyl towards nucleophilic displacement without being incorporated into the final displacement product. Examples of COORx: ester of phenol or naphtol that is further substituted by at least one strong electron withdrawing group, or carboxylic acid activated by carbodiimide, or acyl chloride, or succinimidyl or sulfosuccinimidyl ester. Additional charged and reactive groups include, among others, sulfonyl halides, sulfonyl azides, alcohols, thiols, semicarbazides, hydrazines or hydroxylamines.

The invention still further provides a method of identifying an optimal position for placement of a functional molecule on a peptide having a peptide backbone and a known activity, which includes making a series of peptide conjugates, each peptide conjugate having the same amino acid sequence and the same functional molecule, wherein the functional molecule is linked at a different location along the backbone of every peptide conjugate in the series, and observing which functional molecule location does not substantially interfere with the known activity of the peptide.

The invention also provides a method of identifying an optimal position for placement of a functional molecule in a protein having a known activity and an identified peptide segment for attachment of the functional molecule, which includes making a series of peptide conjugates, each peptide conjugate having the amino acid sequence of the identified peptide segment and the same functional molecule, wherein the functional molecule is linked at a different location along the backbone of every peptide conjugate in the series; replacing the identified peptide segment in each protein of a series of said proteins with a peptide conjugate selected from the series of peptide conjugates to create a series of protein conjugates each having the functional molecule at a different location; and observing which functional molecule location does not substantially interfere with the known activity of the protein.

The invention further provides a method of identifying an optimal position for placement of an environmentally-sensitive functional molecule on a peptide biosensor having a backbone, which includes making a series of peptide conjugates, each peptide conjugate having the same amino acid sequence and the same functional molecule, wherein the functional molecule is at a different location along the backbone of every peptide conjugate in the series, and observing which functional molecule location provides the strongest signal change in response to an environmental change in the peptide conjugate. The signal change can be any observable change in a signal, for example, the change can be a change in fluorescence emission intensity, fluorescence duration or fluorescence emission wavelength. The environmental change in the peptide biosensor can be, for example, an interaction with a target molecule.

The invention still further provides a method of identifying an optimal position for placement of an environmentally-sensitive functional molecule in a protein having a known activity and an identified peptide segment for attachment of the functional molecule, which includes making a series of peptide conjugates, each peptide conjugate having the amino acid sequence of the identified peptide segment and the same environmentally-sensitive functional molecule, wherein the environmentally-sensitive functional molecule is linked at a different location along the backbone of every peptide conjugate in the series; replacing the identified peptide segment in each protein of a series of said proteins with a peptide conjugate selected from the series of peptide conjugates to create a series of protein conjugates, each having the environmentally-sensitive functional molecule at a different location; and observing which functional molecule location provides the strongest signal change in response to an environmental change in the protein conjugate.

The invention also provides a method for detecting GTP activation of a Rho GTPase protein, which includes contacting a polypeptide biosensor with a test substance, wherein said polypeptide biosensor comprises a polypeptide capable of binding a GTP-activated Rho GTPase protein, and wherein said polypeptide is operatively linked to an environmentally sensitive fluorescent dye; and observing fluorescence emissions from the polypeptide biosensor at a wavelength emitted by said fluorescent acceptor dye; wherein the environmentally sensitive fluorescent dye will emit light of a different intensity or a different wavelength when the polypeptide biosensor is bound to the GTP-activated Rho GTPase protein than when the polypeptide biosensor is not bound.

The invention further provides a method of detecting the location of a cellular protein within a living cell that includes providing the living cell with a biosensor capable of binding to a tag on the cellular target protein; and detecting the location of a functional molecule on the biosensor within the living cell. The tag on the cellular target protein can be a peptide segment that has been fused to the cellular protein. In one embodiment, the tag is a peptide which includes SEQ ID NO:16 and that can bind to a biosensor having a peptide segment with SEQ ID NO:15. The biosensor can include a peptide-conjugate of the invention. Any of the functional molecules, pharmaceuticals, toxins, labels, dyes or compounds can also be present on the biosensor. Moreover, any cellular protein can be detected using this method, for example, calmodulin, Rho GTPase, rac, cdc42, mitogen-activated protein kinase, Erk1, Erk2, Erk3, Erk4, IgE receptor ($F_c\epsilon RI$), actin, $\alpha$-actinin, myosin, or a major histocompatibility protein. The methods provided herein can detect and identify the cellular location of proteins and cellular proteins that have never been successful labeled and observed in vivo.

BRIEF DESCRIPTION OF THE FIGURES

In the following detailed description of example embodiments of the invention, reference is made to the accompanying drawings which form a part hereof, and which is shown by way of illustration only, specific embodiments in which the invention may be practiced. It is to be understood that other embodiments may be utilized and structural changes may be made without departing from the scope of the present invention.

FIG. 6 illustrates one method of using an environmentally sensitive fluorescent dye in the present methods so that changes in naturally existing proteins can be detected and observed in vivo or in vitro.

FIG. 6a depicts FRET between the Rac1-Green Fluorescent Protein (GFP-Rac1) fusion and the p21-activated kinase biosensor (PBD) labeled with Alexa-546 dye as shown in FIG. 5. Inactive Rac1 is depicted as a larger gray circle with Green Fluorescent Protein (smaller circle) attached. Upon activation by GTP, Rac1 undergoes a structural change depicted as a gray circle changing to a half-rounded gray rectangle. Unbound PBD is depicted as a black L-shape with an attached Alexa-546 dye (open circle). Before Rac1 is activated, PBD cannot bind and the Alexa-546 cannot undergo FRET. However, after Rac1 activation, the Rac1 assumes a conformation that permits PBD binding. Such binding juxtaposes the Green Fluorescence Protein and the Alexa-546, which produces FRET.

FIG. 6b illustrates how an environmentally sensitive fluorescent dye eliminates the need to create a fusion protein like the GFP-Rac1 protein depicted in FIG. 6a. In FIG. 6b, a natural, unmodified protein is depicted as a gray oval. The protein changes conformation upon activation by GTP, depicted as the transition to a half-rounded gray rectangle. When the protein is in the activated state, a polypeptide-biosensor that binds only to the activated state (black L-shape), with an attached environmentally sensitive dye (open circle), can bind. Upon binding, the environmentally sensitive dye will emit light of a different wavelength, duration or intensity (filled circle) than before binding. Use of this type of environmentally sensitive dye is further illustrated in the Figures to follow.

FIG. 7 illustrates what conditions will optimally provide FRET between GFP-Rac and Alexa-PBD in vitro.

FIG. 8 illustrates how GFP-Rac expression levels and levels of intracellular Alexa-PBD (as observed by fluorescence) correlate with changes in normal cell behavior produced by these proteins.

FIG. 9 illustrates the dynamics of Rac activation during growth factor stimulation of quiescent cells.

FIGS. 9C and 9D demonstrate that simple localization of Alexa-PBD is inferior to FRET in quantifying and localizing Rac-GTP binding (Bar=8 μm). The ruffle in FIG. 9B is shown in close-up in FIG. 9C, visualized using FRET. PBD localization in the same region is visualized using Alexa fluorescence in FIG. 9D, with scaling optimized for detection of the ruffle. Without prior knowledge of the ruffle's location, this localization would have been difficult to discern. The high background due to unbound PBD cannot be eliminated in FIG. 9D and binding to other target proteins is not eliminated as it is in the highly specific FRET signal.

In each of the GFP-Rac images above, intensities range between 300-1100. The image of FRET before serum addition was scaled to demonstrate the low levels of FRET, with values ranging between 0 and 15. In the image of FRET after stimulation, the ruffle contains the highest values of 40 to 65. Nuclear FRET was not seen in any of the cells examined.

FIG. 10 illustrates Rac activation in motile Swiss 3T3 fibroblast cells. This figure shows two examples of where a Rac 1 activation gradient is formed, in confluent monolayer cells and in "wound healing" cells. High Rac1 activation occurred at the leading edge of motility, particularly in wound healing cells. In these experiments high levels of Rac-GTP were frequently seen in the juxtanuclear region of the cell (FIG. 10A). The strong correlation of this gradient with the direction of movement indicates that activated Rac is spatially organized in polarized cells to help guide or propagate movement. Comparison of the GFP (FIG. 10A) and FRET (FIG. 10B) images shows that the distribution of activated Rac does not parallel that of Rac 1 itself. FRET intensities (FIG. 10B) are 0-18 (top image) and 0-32 (bottom image). In the GFP images (FIG. 10A), intensities range between 98-700 (top image) and 100-1100 (bottom image).

Figure 11A:
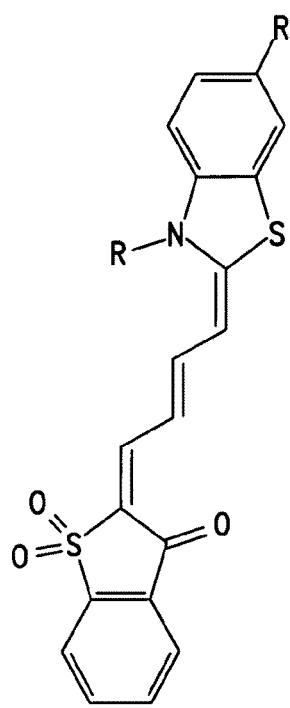
Figure 11B:
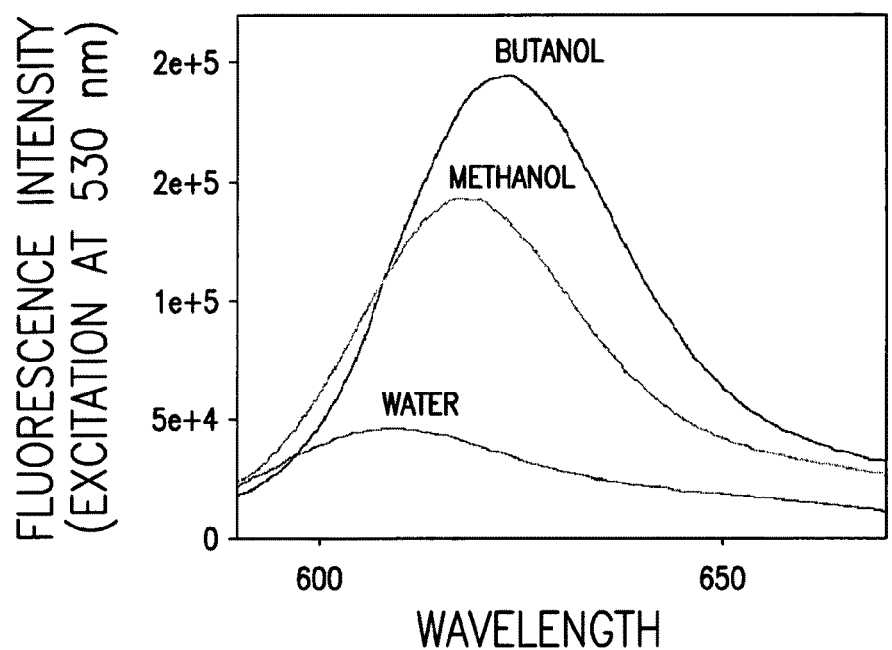

FIG. 11 provides the structure of one of the present fluorescent dyes and the spectrum of fluorescence emission for that dye in water, methanol and butanol. As illustrated, the fluorescent emission of this dye increases with increasing solvent hydrophobicity. This figure illustrates the environmental-sensitivity of this dye.

Figure 12A:
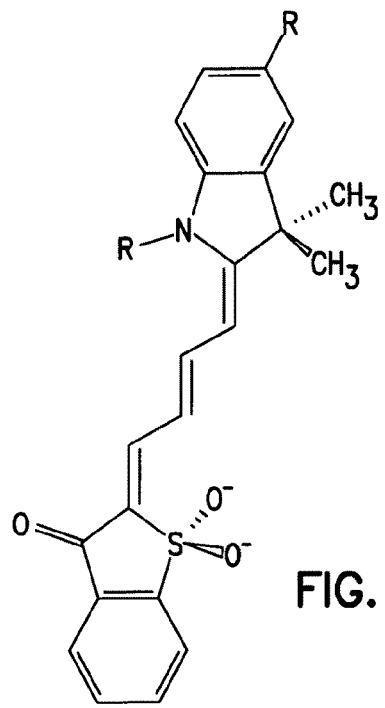
Figure 12B:
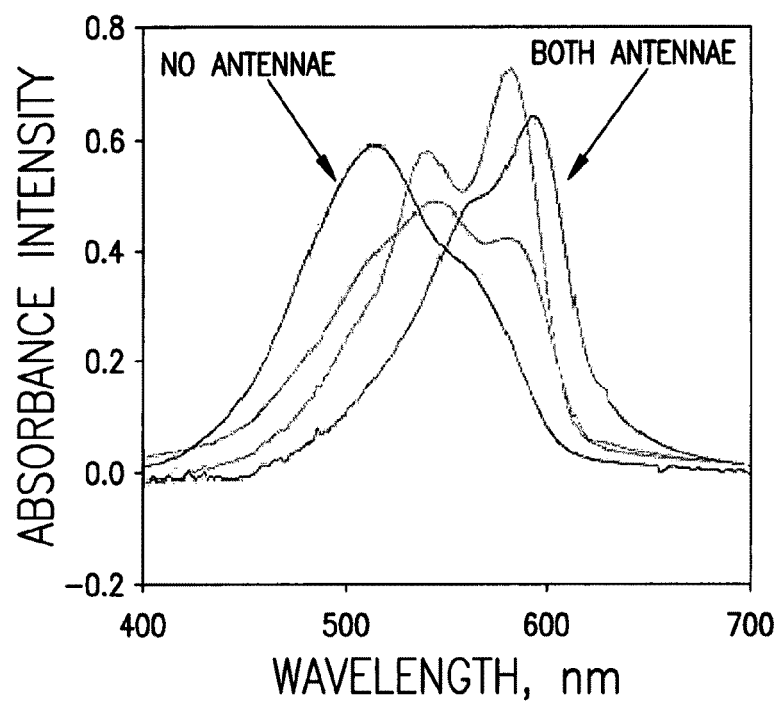

FIG. 12 provides the structure of another fluorescent dye of the present invention and shows its spectrum in aqueous solution, compared to similar dyes lacking the groups designed to prevent aggregation. In the curve from each dye, the peak to the right is the unconjugated, highly fluorescent form of the dye, while that to the left is the weakly fluorescent form. The curve furthest to the right is the dye containing groups to prevent aggregation. As illustrated, the chosen groups help prevent aggregation of the dye.

Figure 13:
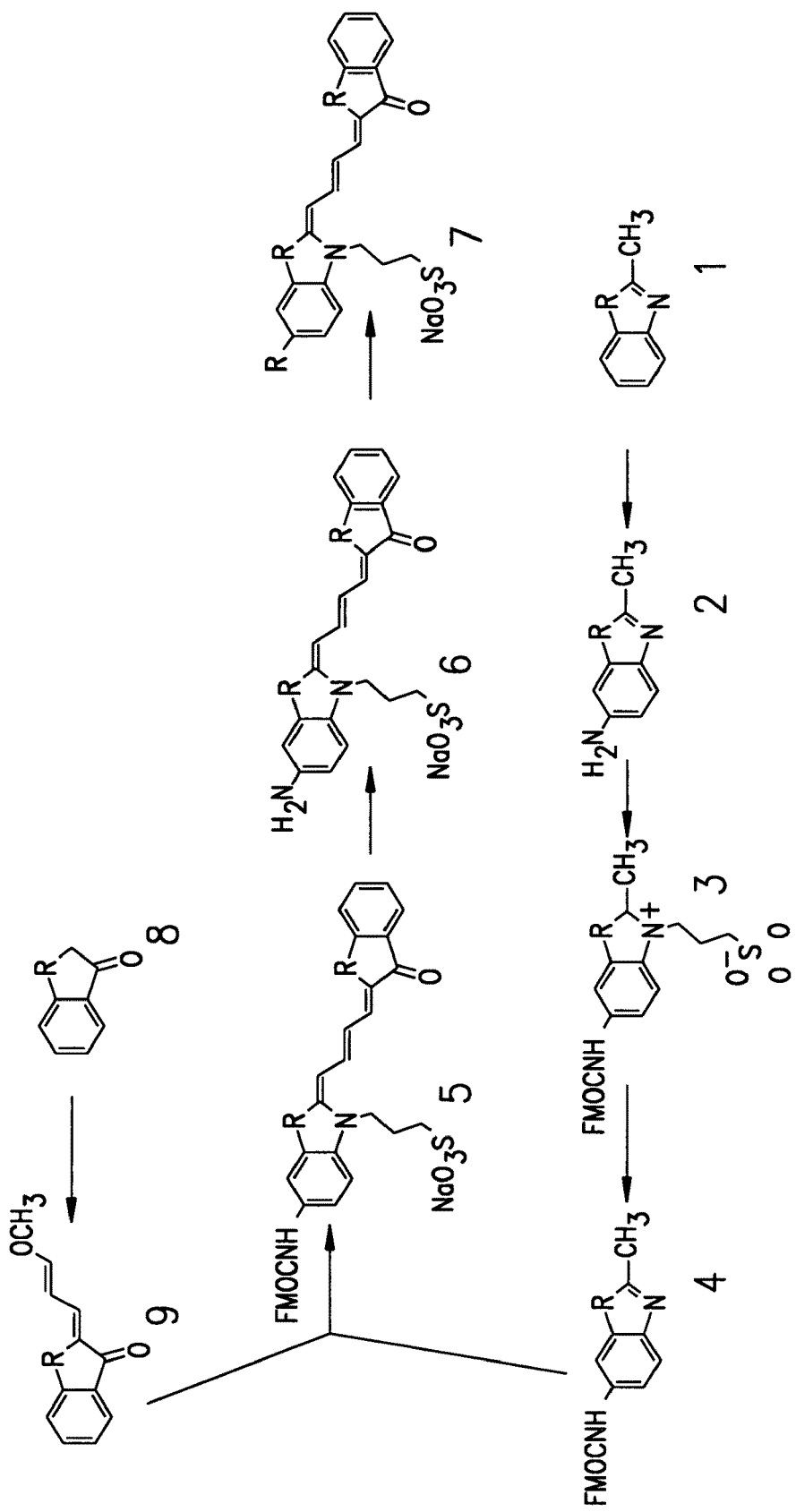
Figure 14:
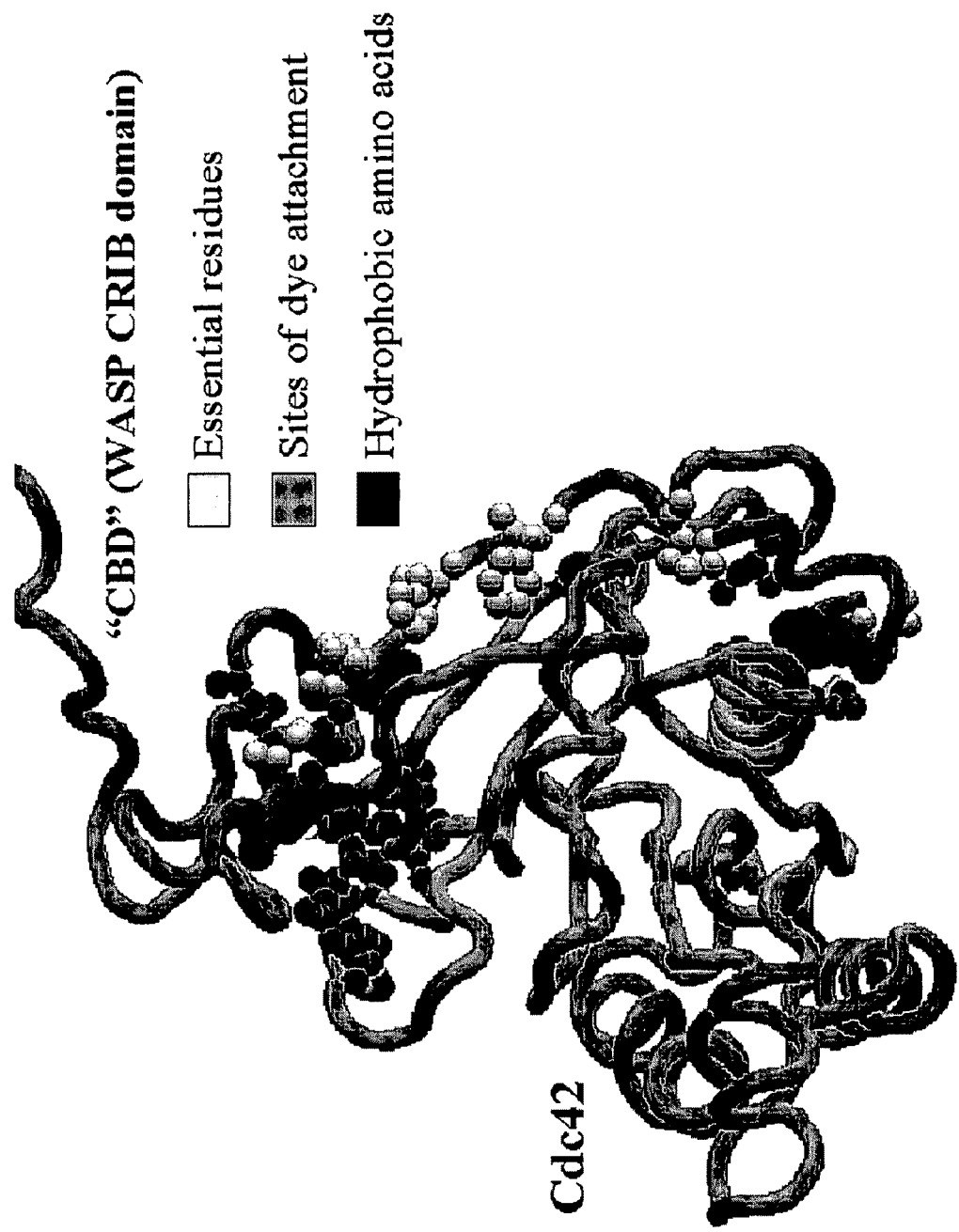

FIG. 13 provides one method for synthesizing a dye of the present invention. Conversion of compound 1 to an amine 2 followed by protection of the amine provides compound 3, which can be alkylated to give compound 4. Reaction of compound 4 with compound 9 provides compound 5, which can be deprotected to provide amine 6. Alkylation or acylation of amine 6 with a chain carrying a charged group, or with a chain bearing a reactive group for conjugation to another molecule, or with another molecule directly provides a dye of the invention 7. Intermediate compound 9 can be prepared by condensation of compound 8 with the requisite aldehyde, under conditions that are known in the art FIG. 14 provides a three-dimensional image of the CRIB domain ("CBD") of the Wiscott-Aldrich syndrome protein (WASP) bound to Cdc42. The essential residues are depicted in yellow, hydrophobic residues depicted in purple and the red sites show positions where the new dyes were attached to generate changes in fluorescence when the CBD bound Cdc42.

Figure 15:
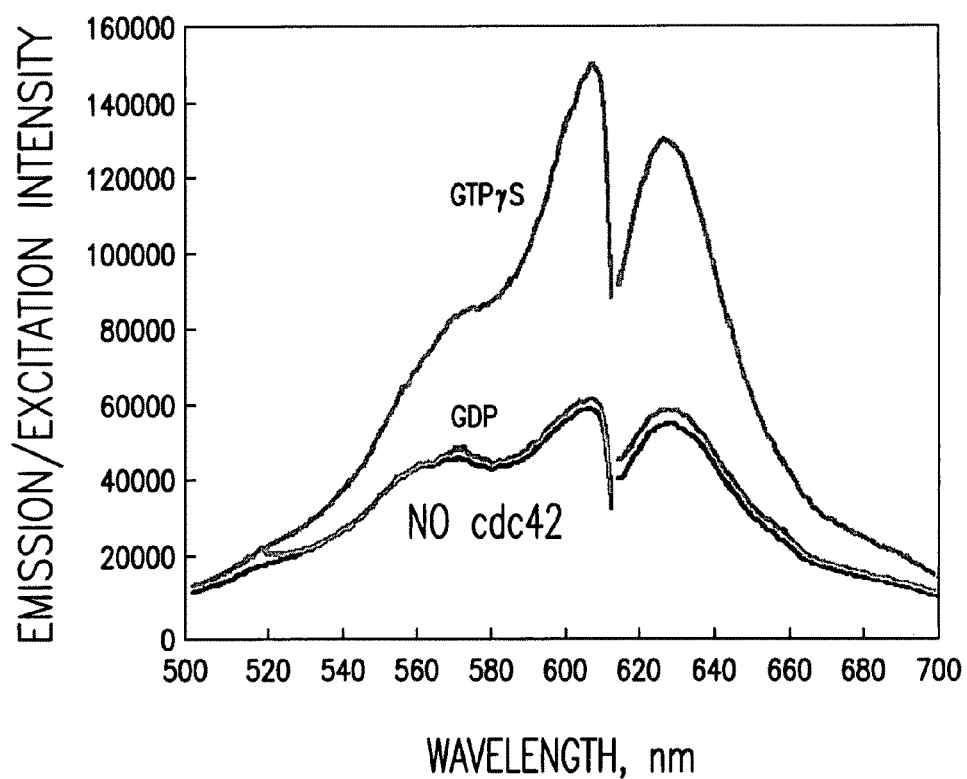

FIG. 15 provides the intensity of fluorescence at various wavelengths observed when fluorescently labeled CBD binds to cdc42. When cdc42 is activated with GTPγS, highly intense fluorescence is observed (line labeled "GTPγS"), compared to when no cdc42 is present (line labeled "no cdc42"), or when cdc42 is not activated (line labeled "GDP").

Figure 16:
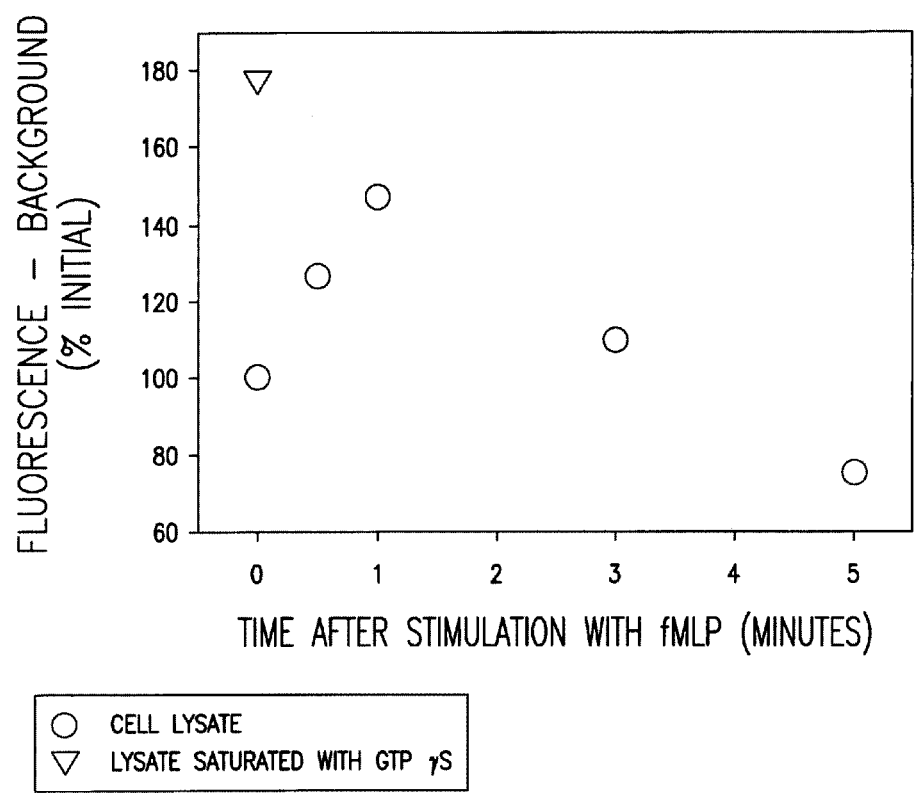

FIG. 16 shows how the present methods can be used for in vitro assays on crude cellular lysates. In this case, the fluorescently labeled CBD was added to a neutrophil lysate. Upon binding to activated cdc42, CBD will emit fluorescence of greater intensity. At time zero fMLP, which stimulates neutrophils to activate cdc42, was added to the cellular lysate and the amount of fluorescence generated by the lysate (●) was measured as a function of time. As a control, the maximal amount of fluorescence that could be obtained from the lysate was estimated by adding saturating levels of GTPγS (▼), which would activate most or all of the cdc42 in the cellular lysate. In this manner the levels of cdc42 in a cellular population can be quantified.

Figure 17:
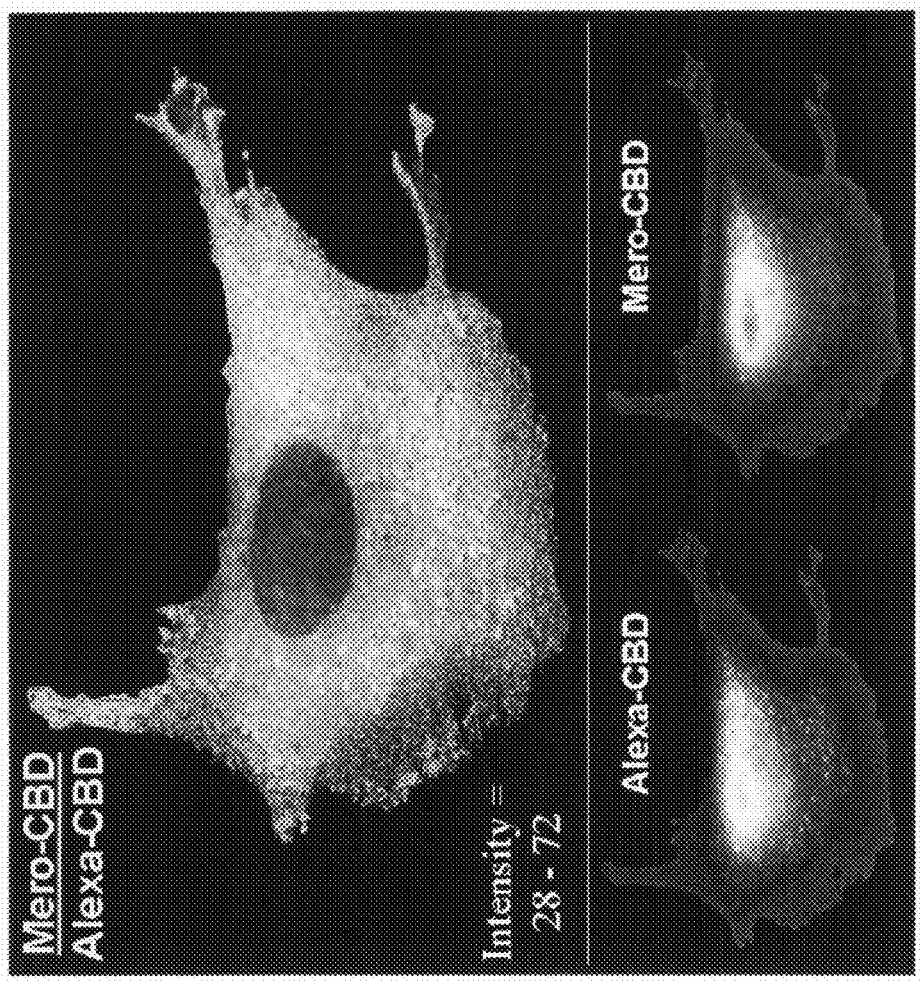

FIG. 17 provides photomicrographs of live cells injected with fluorescently labeled CBD. The lighter colors indicate where the activated cdc42 is present within the cells. The merocyanin dye ("mero") is an environmentally sensitive dye that will fluoresce at higher intensity upon binding of the CBD-mero conjugate to activated cdc42. In this case, the intensity of fluorescence emitted by a non-environmentally sensitive fluorophore (Alexa) linked to CBD was determined relative to the intensity of fluorescence emitted by the CBD-mero fluorophore. The ratio of the two permitted background fluorescence intensity to be subtracted so that the fluorescence from activated cdc-42 could be localized with greater precision.

Figure 18:
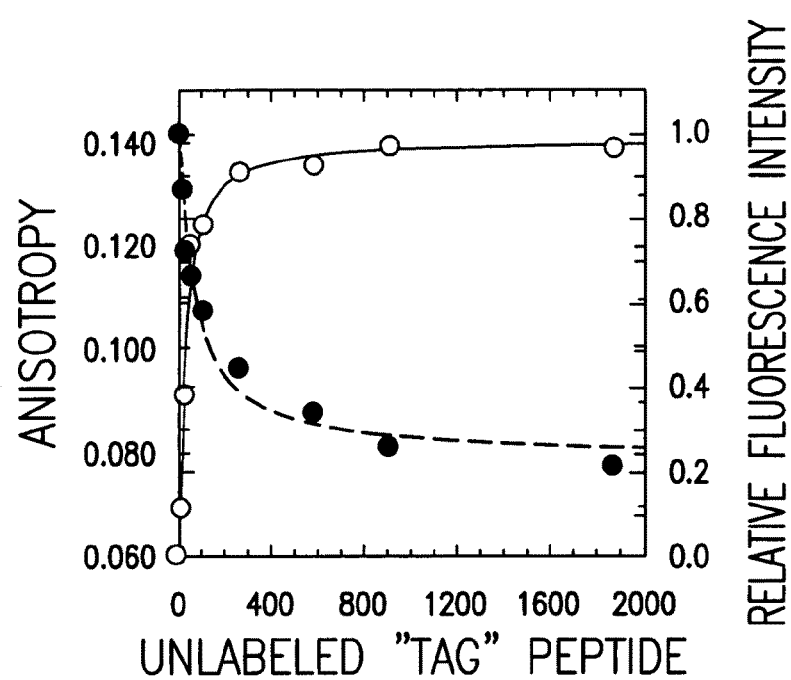

FIG. 18 illustrates the affinity of the labeled leucine zipper peptide biosensor for the leucine peptide tag as determined by equilibrium fluorescence titration, which monitored the changes in anisotropy (o) and fluorescence intensity (•) as the amount of tag binding peptide was increased. Upon binding, the labeled biosensor showed a drop in quantum yield and a more than 230% increase in rhodamine anisotropy, indicating considerable reduction in rotation of the dye. The anisotropy values plotted against the unlabeled peptide tag concentration were fit to an equation describing this interaction as a function of unlabeled peptide concentration, indicating a tight interaction with a dissociation constant (Kd) of 5.4±1.1 nM.

Figure 19:
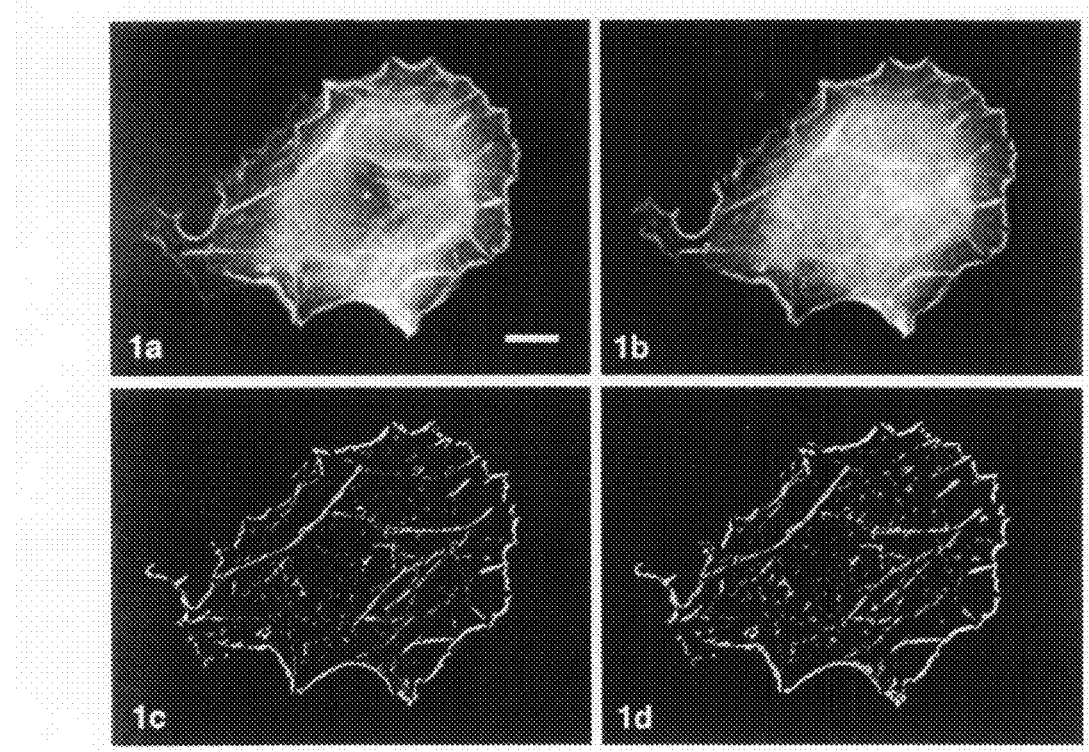

FIG. 19 provides photomicrographs of the same cell with visualization of α-actinin by fluorescently labeled GFP-α-actinin and a rhodamine peptide biosensor of the invention. Cos-7 cells were transfected with an α-actinin construct with GFP fused to the N-terminus and the tag peptide on the C-terminus. The tag peptide and the rhodamine-peptide biosensor bound as illustrated in FIG. 18. The rhodamine-peptide biosensor was injected into these cells and α-actinin localization was visualized using GFP or rhodamine fluorescence. FIGS. 19a and 19c show GFP images and FIGS. 19b and 19d show rhodamine images taken of the same cells. The similar fluorescence distribution in the GFP image (FIG. 19a) and rhodamine image (FIG. 19b) demonstrate labeling of α-actinin with a high degree of specificity. FIGS. 19c (GFP) and 19d (rhodamine) show deconvolution imaging of the same cell. This technique removes out-of-focus light, to demonstrate more clearly the coincidence of emission from the two fluorophores. (Bar=10 microns).

Figure 20:
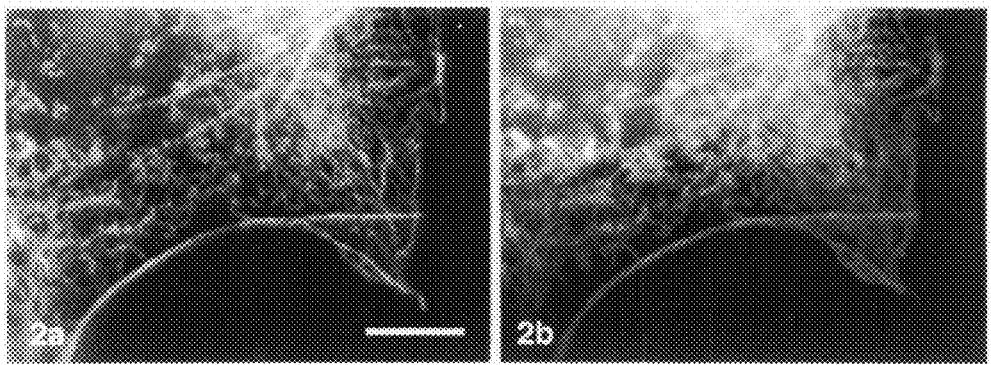

FIG. 20 provides photomicrographs of a different cell than is shown in FIG. 19, with visualization of α-actinin by fluorescently labeled GFP-α-actinin and a rhodamine peptide biosensor of the invention as described in FIG. 19. FIG. 20a provides GFP fluorescence and FIG. 20b provides rhodamine fluorescence. (Bar=10 microns).

Figure 21:
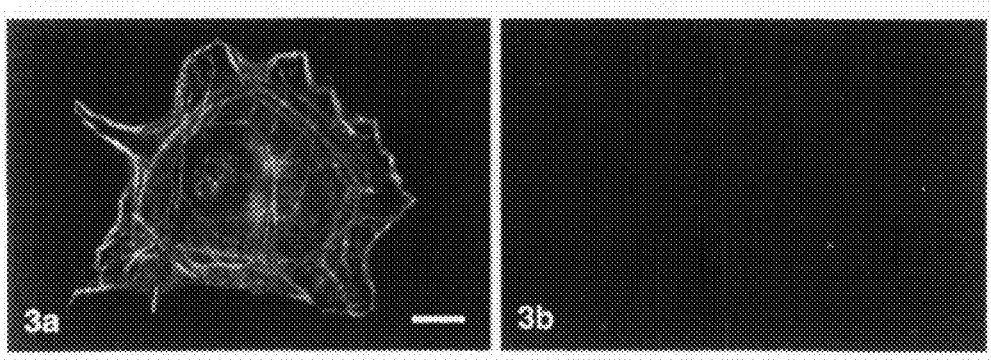

FIG. 21 is a representative example from control experiments in which cells were transfected with the GFP construct described in FIG. 18, but not injected with rhodamine peptide. FIG. 21 a shows GFP fluorescence and FIG. 21b shows rhodamine fluorescence, taken under exposure conditions and with fluorescence levels similar to those in FIGS. 19 and 20. This control demonstrated that the rhodamine fluorescence was not simply 'bleedthrough' of GFP into the rhodamine image. Similar results were obtained by injecting rhodamine peptide biosensor into nontransfected cells, showing that the GFP fluorescence was not due to rhodamine 'bleedthrough' (data not shown). (Bar=10 microns).

Figure 22:
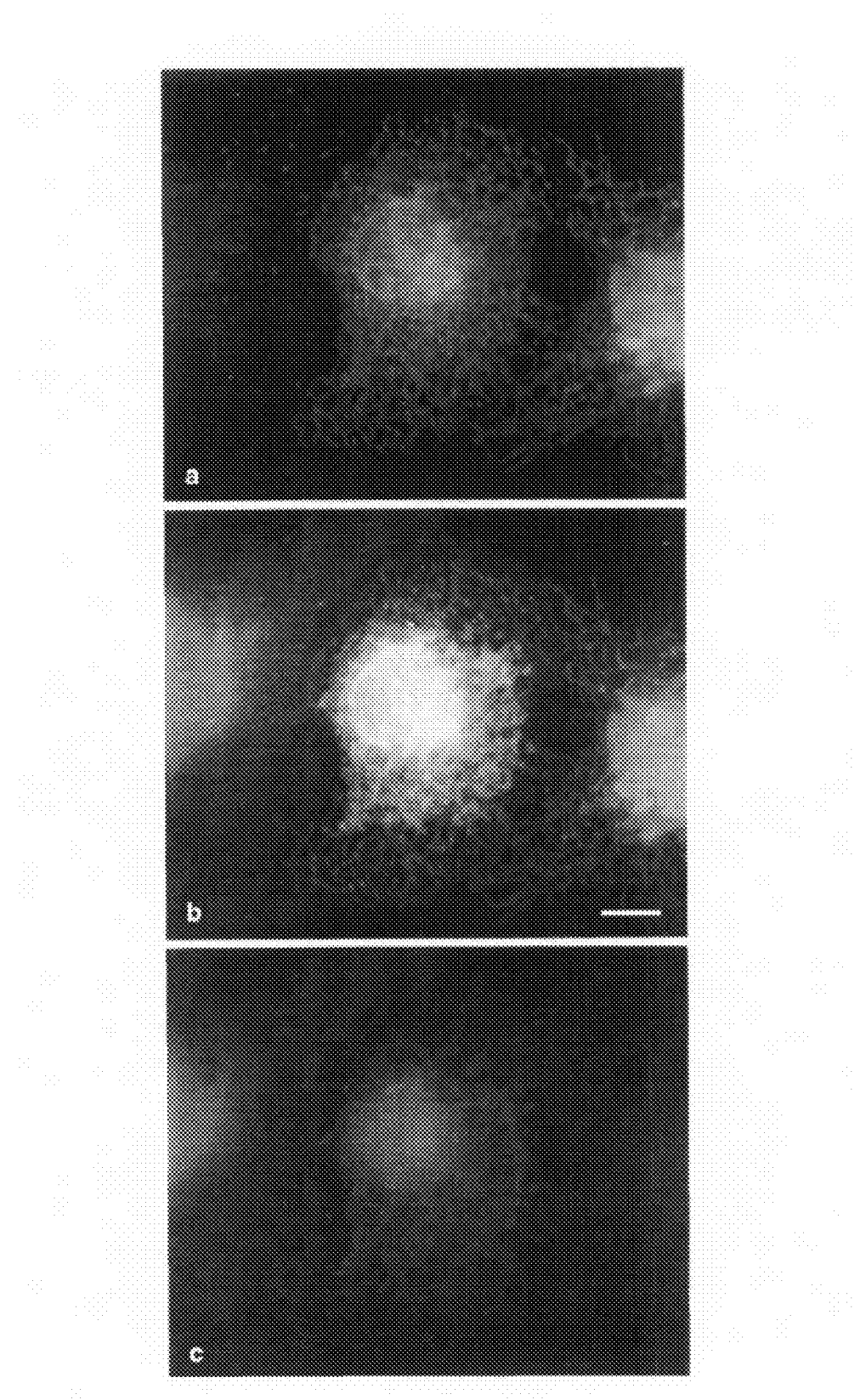

FIG. 22 provides photomicrographs illustrating fluorescent labeling of an endoplasmic reticulum membrane protein in vivo. A subunit of the Fe receptor ($F_c \epsilon RI\ \alpha$), a protein which spans the endoplasmic reticulum membrane, was tagged with. Cells were cotransfected with an MHC-GFP fusion protein as an endoplasmic reticulum marker, and Fe receptor fused to the peptide tag. The cells were then injected with the rhodamine-labeled peptide and imaged in both rhodamine and GFP channels. FIG. 22a shows the GFP fluorescence of the MHC marker, FIG. 22c shows the rhodamine fluorescence of the tagged $F_c \epsilon RI\alpha$ receptor. The images from FIGS. 22a and c are merged in FIG. 22b. The MHC-GFP is more broadly distributed relative to the Fc receptor, which appears to concentrate in ER regions closer to the nucleus and in the nuclear membrane. Note that the GFP-expressing cell which was not injected with rhodamine does not artefactually appear in the rhodamine image, indicating again that similar rhodamine and GFP fluorescence are not due to 'bleedthrough' of GFP fluorescence into the rhodamine image (Bar=10 microns).

Figure 23:
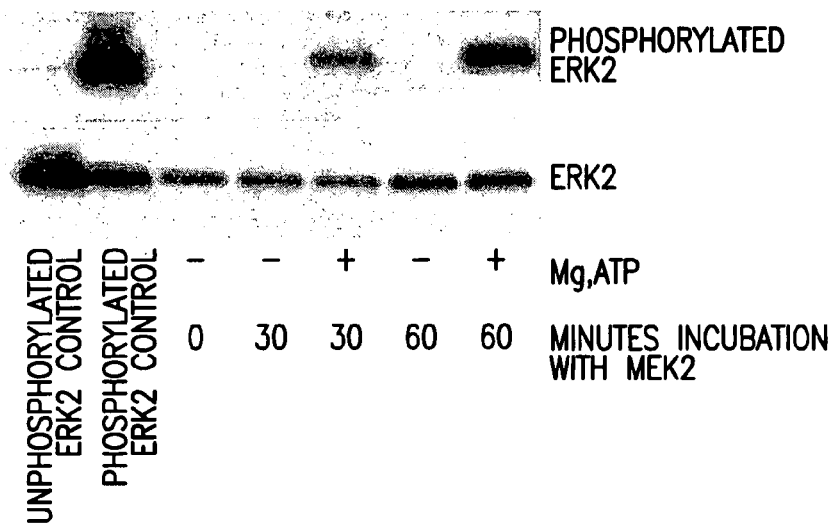

FIG. 23 shows the fluorescence of the ERK2-dye construct under different conditions. ERK2 was activated with MEK for 0-60 min, as indicated in the figure. When Mg and ATP were added, ERK2 was phosphorylated; no such phosphorylation was observed when no Mg, ATP or MEK was present. The data shown here demonstrate that MEK can interact with the labeled protein.

Figure 24:
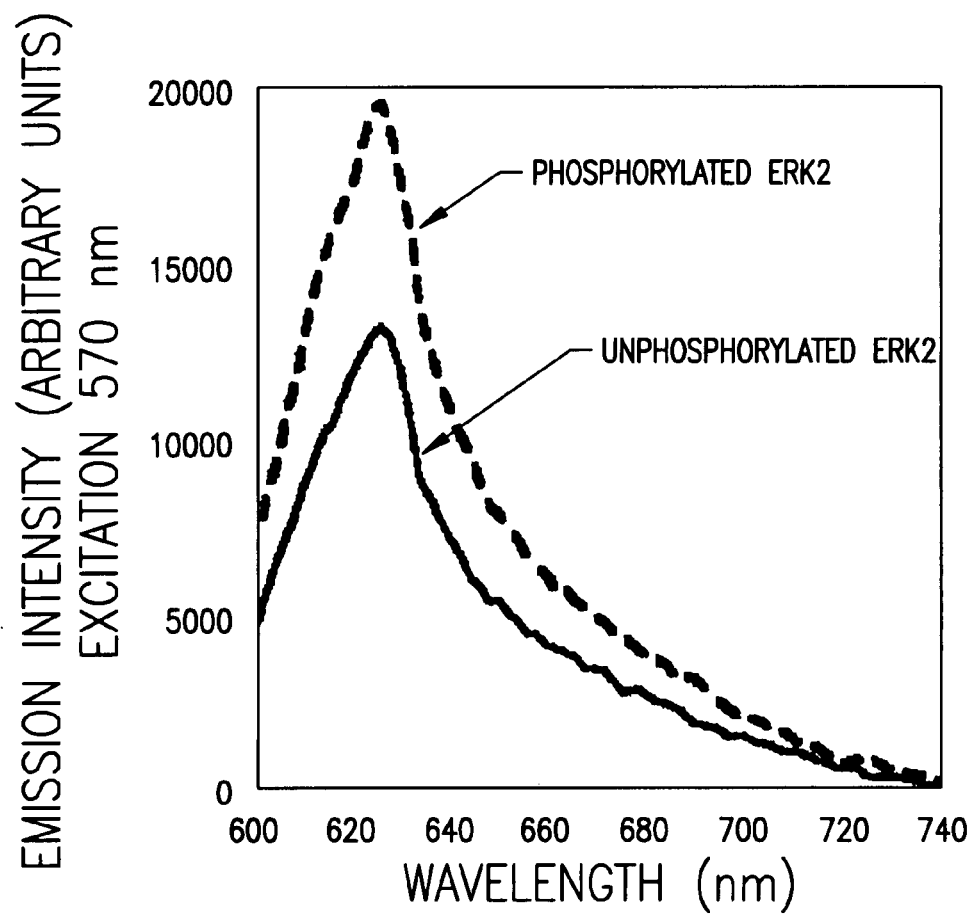

FIG. 24 shows the fluorescence intensity as a function of wavelength for ERK2 when ERK2 is phosphorylated and unphosphorylated. Approximately 1.6-fold increase in emission was observed, when the Erk2 was phosphorylated.

Figure 25:
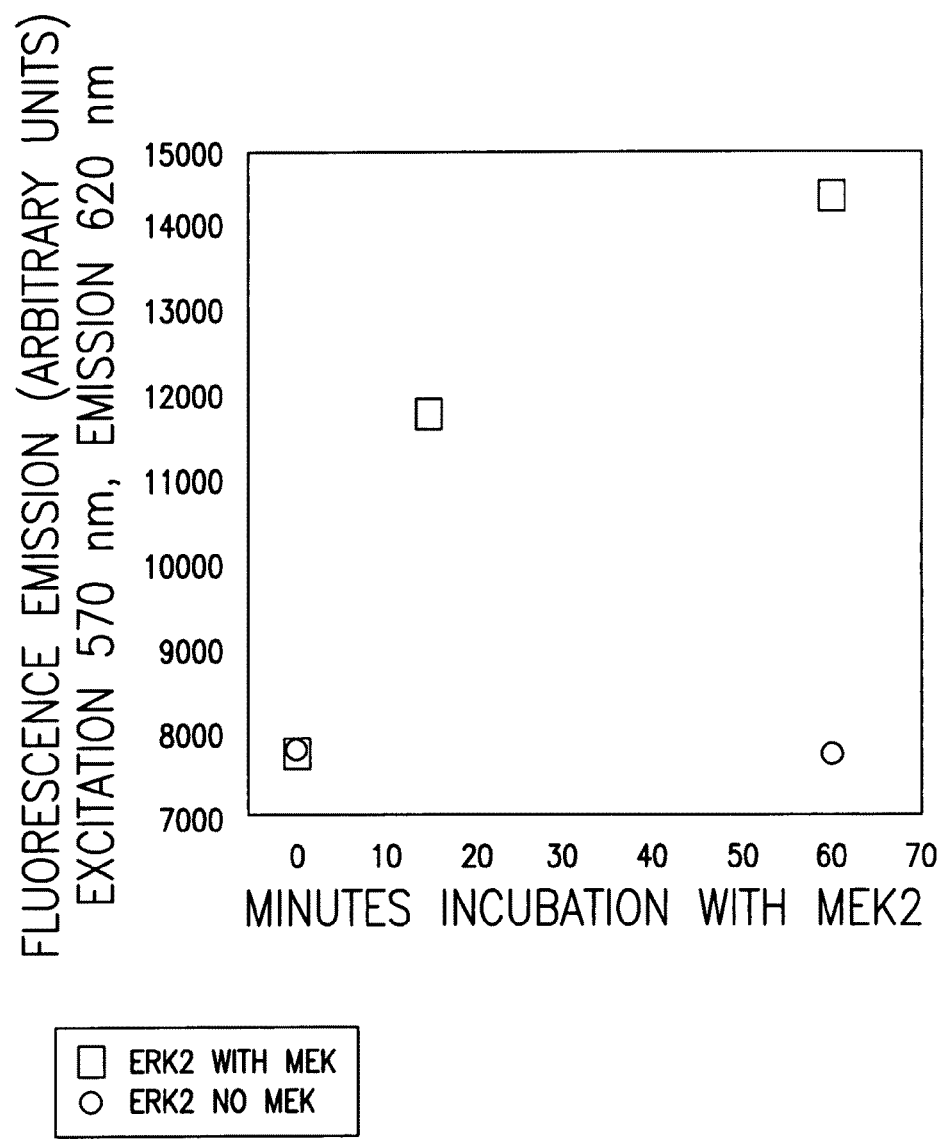

FIG. 25 shows the fluorescence of ERK2, in the presence and absence of MEK, as a function of time of incubation with MEK. No substantial Erk2 fluorescence was observed when MEK was not present. This result demonstrated the suitability of the present methods for detecting activation of ERK2 in live cells.

DETAILED DESCRIPTION

The following definitions are used, unless otherwise described.

Alkylene, alkenylene, alkynylene, etc. denote both straight and branched groups; but reference to an individual radical such as "propylene" embraces only the straight chain radical; a branched chain isomer such as "isopropylene" being specifically referred to. Aryl denotes a phenyl radical or an ortho-fused bicyclic carbocyclic radical having about nine to ten ring atoms in which at least one ring is aromatic.

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methylalanine, para-benzoylphenylalanine, phenylglycine, propargylglycine, sarcosine, and tert-butylglycine). The term also includes natural and unnatural amino acids bearing a conventional amino protecting group (e.g. acetyl or benzyloxycarbonyl), as well as natural and unnatural amino acids protected at the carboxy terminus (e.g. as a ($C_1$-$C_6$)alkyl, phenyl or benzyl ester or amide). Other suitable amino and carboxy protecting groups are known to those skilled in the art (See for example, T. W. Greene, *Protecting Groups In Organic Synthesis*; Wiley: New York, 1981, and references cited therein).

The term "peptide" includes any sequence of 2 or more amino acids. The sequence may be linear or cyclic. For example, a cyclic peptide can be prepared or may result from the formation of disulfide bridges between two cysteine residues in a sequence. Thus, the term includes proteins, enzymes, antibodies, oligopeptides, and polypeptides. Peptide sequences specifically recited herein are written with the amino terminus on the left and the carboxy terminus on the right.

An "aminooxy group" is a group having the following formula

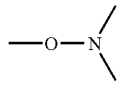

wherein the open valences are filled by any acceptable radical. A "secondary aminooxy group" is an aminooxy group where one of the open valences on the nitrogen is filled by a radical other than a hydrogen.

The term "functional molecule" includes any compound that can be linked to a peptide to provide a peptide conjugate having useful properties. Such conjugates may be useful for studying the structure or function of the peptide, or a polypeptide, antibody, antigen or other protein. Such conjugates can also be used for therapeutic treatments and diagnoses. Functional molecules linked to peptides by the present methods can be used in any assay, procedure or tracing protocol known to one of skill in the art. The functional molecules may also be used with biosensors as contemplated below. Peptide-conjugates with such functional molecules may be useful for drug screening, as pharmacological tools, as research tools, or as therapeutic agents. For example, the term functional molecule includes labels, dyes, ESR probes, reporting groups, biophysical probes, peptides, polynucleotides, therapeutic agents, pharmaceuticals, toxins, cross-linking groups (chemical or photochemical), a compound that modifies the biological activity of the peptide, or a caged molecule (e.g. a reporting molecule or a biologically active agent that is masked and that can be unmasked by photoactivation or chemical means).

The term "biophysical probe" includes any group that can be detected in Vitro or in vivo, such as, for example, a fluorescent group, a phosphorescent group, a nucleic acid indicator, an ESR probe, another reporting group, a moiety, or a dye that is sensitive to pH change, ligand binding, or other environmental aspects.

Amino acids and peptides that include one or more aminooxy groups are useful intermediates for preparing peptide conjugates. The aminooxy group(s) can typically be positioned at any suitable position on the amino acid or peptide. For example, the aminooxy group(s) can conveniently be incorporated into the side chain of the amino acid or into one or more side chains of the peptide. Thus, as used herein with respect to the amino acids and peptides of the invention, the term "a radical comprising one or more aminooxy groups" includes any organic group that can be attached to the amino acid or peptide that includes one or more aminooxy groups. For example, the term includes a carbon chain having two to ten carbon atoms; which is optionally partially unsaturated (i.e. contains one or more double or triple bonds); which chain is optionally interrupted by one or more (e.g. 1, 2, or 3) —NH—, —O—, or —S—; which chain is optionally substituted on carbon with one or more (e.g. 1, 2, or 3) oxo (═O) groups; and which chain is optionally substituted with one or more (e.g. 1, 2, or 3) aminooxy groups. Preferably, the aminooxy group(s) are secondary aminooxy groups.

The term "cross-linking group" refers to any functionality that can form a bond with another functionality, such as photoaffinity label or a chemical crosslinking agent.

The term "caged molecule" includes a molecule or reporter group that is masked such that it can be activated (i.e. unmasked) at a given time or location of choice, for example using light or a chemical agent.

Specific and preferred values listed below for radicals, substituents, and ranges, are for illustration only; they do not exclude other defined values or other values within defined ranges for the radicals and substituents.

Specifically, $(C_1-C_6)$alkylene can be methylene, ethylene, propylene, isopropylene, butylene, iso-butylene, sec-butylene, pentylene, or hexylene; $(C_3-C_8)$cycloalkyl can be cyclopropyl, cyclobutyl, cyclopentyl, cyclohexyl, cycloheptyl, or cyclooctyl; $(C_2-C_6)$alkenylene can be vinylene, allylene, 1-propenylene, 2-propenylene, 1-butenylene, 2-butenylene, 3-butenylene, 1,-pentenylene, 2-pentenylene, 3-pentenylene, 4-pentenylene, 1-hexenylene, 2-hexenylene, 3-hexenylene, 4-hexenylene, or 5-hexenylene; $(C_2-C_6)$alkynylene can be ethynylene, 1-propynylene, 2-propynylene, 1-butynylene, 2-butynylene, 3-butynylene, 1-pentynylene, 2-pentynylene, 3-pentynylene, 4-pentynylene, 1-hexynylene, 2-hexynylene, 3-hexynylene, 4-hexynylene, or 5-hexynylene; and aryl can be phenyl, indenyl, or naphthyl;

A specific value for R is a radical of formula (V):

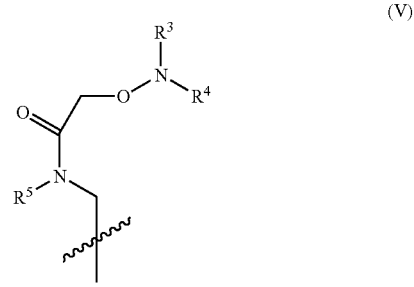

wherein $R^3$ is hydrogen, $(C_1-C_6)$alkyl, an amino protecting group, or a radical comprising one or more aminooxy groups;

$R^4$ is hydrogen, or an amino protecting group; and $R^5$ is hydrogen, or $(C_1-C_6)$alkyl.

A specific value for $R^1$ is hydrogen or benzyloxycarbonyl.

A specific value for $R^2$ is hydrogen.

A specific value for $R^3$ is methyl.

A specific value for $R^4$ is hydrogen, 2-chlorobenzyloxycarbonyl, or benzyloxycarbonyl.

A specific value for $R^5$ is hydrogen.

A specific value for $R^6$ is an antibody.

A specific value for $R^6$ is a peptide or polypeptide or antibody that includes about 2 to about 1000 amino acids. A more specific value for $R^6$ is a peptide that includes about 5 to about 500 amino acids. An even more specific value for $R^6$ is a peptide that includes about 10 to about 100 amino acids.

Specifically X is a linking group that is about 5 angstroms to about 100 angstroms in length. More specifically, X is a linking group of about 5 angstroms to about 25 angstroms in length.

Specifically X is —$R_a$—C(═O)—NH—$R_b$— wherein each of $R_a$ and $R_b$ is independently $(C_1-C_6)$alkylene. Preferably, each of $R_a$ and $R_b$ is methylene (—$CH_2$—).

A preferred value for $R^6$ is KKKEKERPEISLPSDFEHTIHVGF DACTGEFTGMPEQWARLLQT (SEQ ID NO: 1) or an antibody.

A specific value for $R^7$ is hydrogen.

Another specific value for $R^7$ is $(C_1-C_6)$alkyl.

A preferred value for $R^7$ is methyl.

Specifically Y is a linking group that is about 5 angstroms to about 100 angstroms in length. More specifically, Y is a linking group of about 5 angstroms to about 25 angstroms in length.

A specific value for Y is $(C_1-C_6)$alkylene.

A preferred value for Y is methylene (—$CH_2$—).

Fluorescent Dyes

Any fluorescent dye known to one of skill in the art is contemplated by the present invention as a functional molecule. A fluorescent dye can be excited to fluoresce by exposure to a certain wavelength of light. When used as the reporter molecule of the biosensors of the present invention, the dye is preferably environmentally sensitive. As used herein, "environmentally sensitive" means that the signal from the functional molecule changes when the peptide, polypeptide or antibody interacts with, or becomes exposed to, a different environment. For example, when the environmentally sensitive functional molecule is a fluorescent dye, the fluorescence from that fluorescent dye will change as the environment changes. In one embodiment an environmentally sensitive fluorescent dye attached to a peptide, polypeptide or antibody will fluoresce differently upon target binding by the peptide, polypeptide or antibody to which the dye is attached. Any dye which emits fluorescence and whose fluorescence changes when the pH or the hydrophilicity/hydrophobicity of the environment changes is an environmentally sensitive dye contemplated by the present invention.

Preferred fluorescent groups include molecules that are capable of absorbing radiation at one wavelength and emitting radiation at a longer wavelength, such as, for example, Alexa-532, Hydroxycoumarin, Aminocoumarin, Methoxycoumarin, Coumarin, Cascade Blue, Lucifer Yellow, P-Phycoerythrin, R-Phycoerythrin, (PE), PE-Cy5 conjugates, PE-Cy7 conjugates, Red 613, Fluorescein, BODIPY-FL, BODIPY TR, BODIPY TMR, Cy3, TRITC, X-Rhodamine, Lissamine Rhodamine B, PerCP, Texas Red, Cy5, Cy7, Allophycocyanin (APC), TruRed, APC-Cy7 conjugates, Oregon Green, Tetramethylrhodamine, Dansyl, Dansyl aziridine, Indo-1, Fura-2, FM 1-43, DilC18(3), Carboxy-SNARF-1, NBD, Indo-1, Fluo-3, DCFH, DHR, SNARF, Monochlorobimane, Calcein, N-(7-nitrobenz-2-oxa-1,3-diazol-4-yl) amine (NBD), ananilinonapthalene, deproxyl, phthalamide, amino pH phthalamide, dimethylamino-naphthalenesulfonamide, probes comparable to Prodan, Lordan or Acrylodan and derivatives thereof. Coumarin fluorescent dyes include, for example, amino methylcoumarin, 7-diethylamino-3-(4'-(1-maleimidyl)phenyl)-4-methylcoumarin (CPM) and N-(2-(1-maleimidyl)ethyl)7-diethylaminocoumarin-3-carboxamide (MDCC). Preferred fluorescent probes are sensitive to the polarity of the local environment and are available to those of skill in the art.

Other useful functional molecules include those that display fluorescence resonance energy transfer (FRET). Many such donor-acceptor pairs are known, and include fluorescein to rhodamine, coumarin to fluorescein or rhodamine, etc. Still another class of useful label pairs include fluorophore-quencher pairs in which the second group is a quencher, which decreases the fluorescence intensity of the fluorescent group. Some known quenchers include acrylamide groups, heavy atoms such as iodide and bromate, nitroxide spin labels such as TEMPO, etc. These can be adapted for use as environmentally sensitive functional molecules of biosensors.

Exemplary fluorescent proteins which can be used to label the present peptides, polypeptides and antibodies include green fluorescent protein (GFP), cyan fluorescent protein (CFP), red fluorescent protein (RFP), yellow fluorescent protein (YFF), enhanced GFP (EGFF), enhanced YFP (EYFP), and the like.

New Fluorescent Dyes

The present invention also provides novel fluorescent dyes that retain high fluorescence emission after conjugation to other molecules and avoid problems of aggregation and insolubility. These dyes are particularly preferred for many of the imaging methods and conjugates contemplated but need not be restricted to use in the methods and conjugates contemplated herein. Thus, the present invention is directed to highly fluorescent dyes of structure IV wherein, each m is separately an integer ranging from 1-3;

n is an integer ranging from 0 to 5;

$R^8$, $R^{11}$ and $R^{12}$ are separately CO, $SO_2$, C=$C(CN)_2$, S, O or $C(CH_3)_2$;

each $R^{13}$ is alkyl, branched alkyl or heterocyclic ring derivatized with charged groups to enhance water solubility and enhance photostability;

$R^9$ and $R^{10}$ are chains carrying charged groups to enhance water solubility (i.e. sulfonate, amide, ether) and/or chains bearing reactive groups for conjugation to other molecules. The reactive group is a functional group that is chemically reactive (or that can be made chemically reactive) with functional groups typically found in biological materials, or functional groups that can be readily converted to chemically reactive derivatives using methods well known in the art. In one embodiment of the invention, the charged and reactive groups are separately haloacetamide (—NH—(C=O)—$CH_2$—X), where X is Cl, Br or I. Alternatively, the charged and reactive groups are separately amine, maleimide, isocyanato (—N=C=O), isothiocyanato(—N=C=S), acyl halide, succinimidyl ester, or sulfosuccinimidyl ester. In another embodiment, the charged and reactive groups are carboxylic acid (COOH), or derivatives of a carboxylic acid. An appropriate derivative of a carboxylic acid includes an alkali or alkaline earth metal salt of carboxylic acid. Alternatively, the charged and reactive groups are reactive derivatives of a carboxylic acid (—COORx), where the reactive group Rx is one that activates the carbonyl group of —COORx toward nucleophilic displacement. In particular, Rx is any group that activates the carbonyl towards nucleophilic displacement without being incorporated into the final displacement product. Examples of COORx: ester of phenol or naphtol that is further substituted by at least one strong electron withdrawing group, or carboxylic acid activated by carbodimide, or acyl chloride, or succinimidyl or sulfosuccinimidyl ester. Additional charged and reactive groups include, among others, sulfonyl halides, sulfonyl azides, alcohols, thiols, semicarbazides, hydrazines or hydroxylamines.

For all dyes of the invention, any net positive or negative charges possessed by the dye are balanced by a biologically compatible counterion or counterions. As used herein, a substance that is biologically compatible is not toxic as used, and does not have a substantially deleterious effect on biomolecules. Examples of useful counterions for dyes having a net negative charge include, but are not limited to, alkali metal ions alkaline earth metal ions, transition metal ions, ammonium and substituted ammonium ions. Examples of useful counterions for dyes having a net positive charge include, but are not limited to chloride, bromide, iodide, sulfate, phosphate, perchlorate, nitrate, tetrafluoroborate.

As used herein, $R^9$ and $R^{10}$ chains for conjugation are alkyl, of unlimited length, preferably with 1-6 carbons, and can include other moieties such as ether, amide, or sulfonate to improve water solubility. The groups can be substituted on the end or in the middle of the alkyl chain.

In one embodiment, the fluorescent dye of the present invention has the following structure (VI):

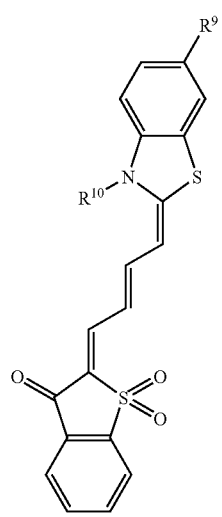

In another embodiment, the fluorescent dye of the present invention has the following structure (VII):

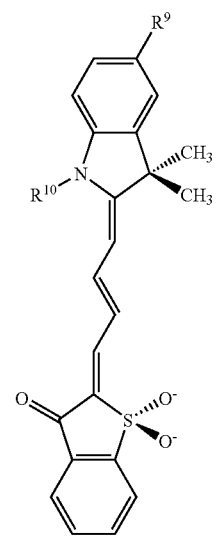

In another embodiment, the fluorescent dye of the present invention has the following structure (VIII):

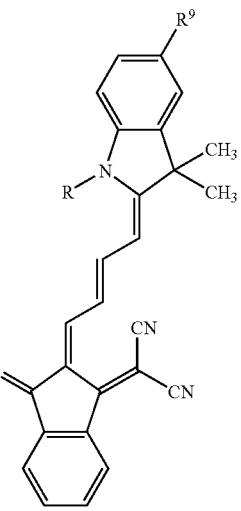

Depending upon their environment, the flourescent dyes of the present invention can exist in somewhat different polarization states. This property can modulate the solubility and the emission wavelength of the dye. For example, the fluorescent dye depicted below can be charged or non-charged.

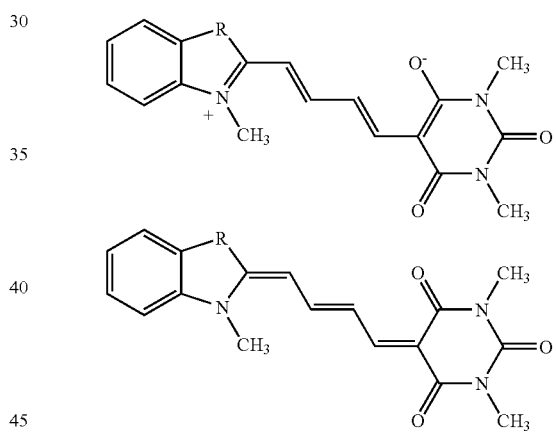

The fluorescent dyes of the present invention can absorb and emit light at a variety of wavelengths, depending on the arrangement and variety of substituents employed. Thus, the choice of whether to use $R^8$, $R^{11}$ and $R^{12}$ as —CO—, —SO$_2$—, —C══C(CN)$_2$—, —S—, —O— or —C(CH$_3$)$_2$— can influence the absorption and emission wavelength. However, by varying the substituents of the present invention, one of skill in the art can readily ascertain which combination of substituents will yield a fluorescent dye with a desired absorption and emission spectrum.

Moreover, according to the present invention, the degree of conjugation of the dye, and in particular, the length of the alkylene chain connecting the two rings, can predictably influence the absorption and emission wavelength of the dye. Thus, addition of one —C══C— group can shift the fluorescence wavelength about +100 nm. Smaller incremental changes in the emission wavelength can be made by adding a conjugated group to one of the rings in the dye. Thus, one of skill in the art can readily modulate the emission wavelength of the dye as desired. In one embodiment, the absorption and emission wavelengths can be altered to range from about 300 nm to about 800 nm. Preferably, the absorption and emission wavelengths of the present dyes range from about 450 nm to higher wavelengths. Any variety of methods can be used to make the present dyes.

Preferred nucleic acid indicators include intercalating agents and oligonucleotide strands, such as, for example, YOYO-1, Propidium Iodide, Hoechst 33342, DAPI, Hoerchst 33258, SYTOX Blue, Chromomycin A3, Mithramycin, SYTOX Green, SYTX Orange, Ethidium Bromide, 7-AAD, Acridine Orange, TOTO-1, TO-PRO-1, Thiazole Orange, Propidium Iodide, TOTO-3, TO-PRO-3, LDS 751.

Synthon and Peptide Intermediates

The synthetic intermediates (i.e. synthons) of the invention that include one or more aminooxy groups can be incorporated into peptides using a variety of techniques that are known in the art. For example, as discussed below, the synthons can be incorporated into a peptide using solid-phase peptide synthesis, solution-phase peptide synthesis, native chemical ligation, intein-mediated protein ligation, and chemical ligation.

Peptides may be prepared using solid-phase peptide synthesis (SPPS). For example, according to the SPPS technique, protected amino acids in organic solvents can be added one at a time to a resin-bound peptide chain, resulting in the assembly of a target peptide having a specific sequence in fully-protected, resin-bound form. The product peptide can then be released by deprotection and cleavage from the resin support (Wade, L. G., JR., Organic Chemistry 4th Ed. (1999)). As illustrated in Example 2 below, amino acids containing an aminooxy functional group can be incorporated into peptides using SPPS. Use of this methodology allows an amino acid containing an aminooxy functional group to be positioned at a desired location within a synthesized peptide chain.

Amino acids containing an aminooxy group can also be incorporated into a peptide using solution-phase peptide synthesis (Wade, L. G., JR. Organic Chemistry 4th Ed. (1999)). Solution-phase peptide synthesis involves protecting the amino-terminus of a peptide chain followed by activation of the carboxyl-terminus allowing the addition of an amino acid or a peptide chain to the carboxy-terminus (Wade, L. G., JR. Organic Chemistry 4th Ed. (1999)).

Native chemical ligation is a procedure that can be used to join two peptides or polypeptides together thereby producing a single peptide or polypeptide having a native backbone structure. Native chemical ligation is typically carried out by mixing a first peptide with a carboxy-terminal α-thioester and a second polypeptide with an amino-terminal cysteine (Dawson, P. E., et al., (1994), Science 266:776-779; Cotton, G. J., et al., (1999), J. Am. Chem. Soc. 121:1100-1101). The thioester of the first peptide undergoes nucleophilic attack by the side chain of the cysteine residue at the amino terminus of the second peptide. The initial thioester ligation product then undergoes a rapid intramolecular reaction because of the favorable geometric arrangement of the alpha-amino group of the second peptide. This yields a product with a native peptide bond at the ligation site. A polypeptide beginning with cysteine can be chemically synthesized or generated by intein vectors, proteolysis, or cellular processing of the initiating methionine. This method allows mixing and matching of chemically synthesized polypeptide segments.

The synthons of the invention are particularly useful in combination with native chemical ligation, because native chemical ligation allows a synthetic peptide having a specifically positioned amino acid (e.g. a synthon of the invention) to be selectively ligated to other peptides or into a larger polypeptide, antibody or protein. The ability to specifically incorporate aminooxy modified amino acids into a peptide chain allows useful moieties to be linked at any position within a peptide, polypeptide, antibody or protein. Examples of such moieties that can be incorporated into a peptide using this method include, but are not limited to, phosphorylated or glycosylated amino acids, unnatural amino acids, tags, labels, crosslinking reagents, biosensors, reactive groups, and fluorophores. Another advantage of native chemical ligation is that it allows incorporation of peptides into a polypeptide that are unable to be added by ribosomal biosynthesis.

Intein-mediated protein ligation may also be used to selectively place amino acids containing aminooxy functional groups into peptides. Inteins are intervening sequences that are excised from precursor proteins by a self-catalytic mechanism and thereby expose reactive ends of a peptide. Intein vectors have been developed that not only allow single-step purification of proteins, but also yield polypeptides with reactive ends necessary for intein-mediated protein ligation (IPL) (also called expressed protein ligation)(EPL) (Perler, F. R. and Adam, E., (2000) Curr. Opin. Biotechnol. 11(4):377-83; and Evans, T. C., et al., (1998) Protein Sci 7:2256-2264). This method allows a peptide having a selectively placed amino acid containing an aminooxy functional group to be readily ligated to any peptide with reactive ends generated by intein excision.

Two peptides or polypeptides may also be linked through use of chemical ligation. Chemical ligation occurs when two peptide segments are each linked to functional groups that react with each other to form a covalent bond producing a non-peptide bond at the ligation site (Wilken, J. and Kent, S. B. H., (1998) Curr. Opin. Biotechnol. 9:412-426). This method can be used to ligate a peptide having a specifically positioned aminooxy functional group to another peptide or polypeptide to produce a desired polypeptide that may be later linked to a detectable group.

A functional molecule ("D") can be attached to a peptide comprising an aminooxy group through a direct linkage (e.g. an amide bond —O—N—C(=O)-D) or through a linking group. The structure of the linking group is not crucial, provided it does not interfere with the use of the resulting labeled peptide. Preferred linking groups include linkers that separate the aminooxy nitrogen and the detectable group by about 5 angstroms to about 100 angstroms. Other preferred linking groups separate the aminooxy nitrogen and the detectable group by about 5 angstroms to about 25 angstroms.

For example, the linking group can conveniently be linked to the detectable group through an: 1) amide (—N(H)C (=O)—, —C(=O)N(H)—), 2) ester (—OC(=O)—, —C(=O)O—), 3) ether (—O—), 4) thioether (—S—), 5) sulfinyl (—S(O)—), or 6) sulfonyl (—S(O)$_2$) linkage. Such a linkage can be formed from suitably functionalised starting materials using synthetic procedures that are known in the art.

The linking group can conveniently be linked to the nitrogen of the aminooxy group to form an amide (—O—N(H)C (=O)— or a thiourea linkage (—O—N—C(=S)—N—) linkage, using reagents and conditions that are known in the art.

The aminooxy group can be attached to a peptide through a direct bond (e.g. a carbon-oxygen bond) between the aminooxy oxygen and a side chain of the peptide, or the aminooxy group can be attached to the peptide through a linking group. The structure of the linking group is not crucial, provided it does not interfere with the use of the resulting labeled peptide. Preferred linking groups include linking groups that separate the aminooxy oxygen and the side chain of the peptide by about 5 angstroms to about 100 angstroms. Other preferred linking groups separate the aminooxy oxygen and the side chain of the peptide by about 5 angstroms to about 25 angstroms.

A specific linking group (e.g. X or Y) can be a divalent ($C_1$-$C_6$)alkylene, ($C_2$-$C_6$)alkenylene, or ($C_2$-$C_6$)alkynylene chain, or a divalent ($C_3$-$C_8$)cycloalkyl, or aryl ring.

Thus, a simple and efficient synthetic methodology for site-specific labeling of peptides after synthesis has been developed that provides high yield, selectivity and compatibility with both solid-phase peptide synthesis and $C^\alpha$-thioester peptides. The approach and primary advantages can be summarized as follows:

(1) A protected aminooxy amino acid that can be incorporated into peptides has been synthesized;

(2) Procedures have been optimized to yield highly efficient and specific modification of the aminooxy nitrogen in the presence of unprotected competing nucleophiles, including cysteine, lysine and amino groups;

(3) One preferred electrophile that can be used for labeling, an activated carboxylic ester, is readily available in the majority of commercially available fluorescent dyes and labels;

(4) Labeling of the aminooxy group occurs after synthesis and purification, thus enabling the use of chemically sensitive fluorophores and labels that would otherwise not survive earlier synthetic procedures;

(5) The synthetic methodology is compatible with the steps required for the synthesis of proteins by total chemical synthesis or expressed protein ligation, namely synthesis of $C^\alpha$-peptide thioesters and amide-forming ligations; and (6) Combinatorial screening of both the functional molecule and its placement will enable the rapid synthesis of optimally labeled polypeptide-based biosensors.

Biosensors

Using the methods of the present invention with the synthons and peptides provided herein, antibodies, antigens and other polypeptides can be labeled with or attached to functional molecules. Such labeled or conjugated antibodies and polypeptides have particular utility as biosensors. As used herein, a "biosensor" is a peptide, antigen, polypeptide or antibody with an attached functional molecule. In one embodiment, the functional molecule is a label or dye, however, as used herein, a biosensor can have any functional molecule attached thereto. For example, the functional molecule can be a label, dye, biophysical probe, peptide, polynucleotide, therapeutic agent, pharmaceutical, toxin, cross-linking group (chemical or photochemical), a compound that modifies the biological activity of the peptide, or a caged molecule (e.g. a reporting molecule or a biologically active agent that is masked and that can be unmasked by photoactivation or chemical means).

In one embodiment the functional molecule is dye or label. Such a dye or label can be an environmentally-sensitive fluorescent dye such that fluorescence is emitted by the dye can change when the protein biosensor becomes exposed to a different environment. Such a change in environment can occur, for example, when the biosensor binds to, or associates with, a target protein or cellular structure. The change in fluorescence can be used to quantify or otherwise monitor the amount of binding or interaction between the biosensor and the target site. The Examples provided herein further illustrate how such a biosensor can be used.

The present invention provides methods for identifying an optimal position for the functional molecule on the peptide, polypeptide or antibody which involve generating a series of peptides, each peptide have the same amino acid sequence and functional molecule. However, the functional molecule is positioned at a different location along the backbone of each peptide in the series. To determine which location is best, the strength of the signal from the various peptides is observed under different conditions and the optimal location provides optimal functioning by the functional molecule and the peptide, polypeptide or antibody. For example, when the functional molecule provides a signal, a stronger signal is preferred so long as the function and the chemical and physical properties of the peptide, protein or antibody are not impaired. When an environmentally sensitive functional molecule is chosen, a maximal change in signal is preferred as the environment is changed. For example, when the environmentally sensitive functional molecule is attached to detect an interaction of the peptide with a target, a maximal change in signal is preferred when the peptide binds or interacts with its target, unless of the location of the functional molecule affects the binding affinity, binding selectivity or another desirable attribute of the peptide.

Thus to determine an optimal location for a functional molecule in an antibody or polypeptide which can bind to a target, a series of peptides are first synthesized, each with the functional molecule at a different position. The peptides can be incorporated into the polypeptide or antibody using the methods described herein to generate a series of biosensors, each with a functional molecule at a somewhat different position. The interaction of the different polypeptide or antibody biosensors with target is observed. In general, an optimal position for the functional molecule on such a biosensor is that position which permits stable and selective binding to target with a maximal signal change upon binding.

However, some variability in binding and signal strength can be tolerated so long as an observable, localized signal is detected upon interaction of the biosensor and the target. Thus, the strength of binding between the biosensor and target should be sufficient to permit observation of bound biosensor. If the biosensor is only transiently bound, little or no localized signal from the probe may be observed; instead, only diffuse signal from biosensor in solution may be observed. Similarly, if the biosensor is bound non-selectively, non-localized signal may be detected from many sites. Obviously, a strongly localized signal that clearly correlates with biosensor binding to target is preferred. A readily detectable change in signal strength or quality as the biosensor and target interact is also preferred.

Procedures known to one of skill in the art can be used to detect a signal provided by the functional molecule and to correlate a change in signal by an environmentally sensitive functional molecule. Signals contemplated by the present invention include fluorescent emissions, radioactive emissions, enzymatic production of a colored product, and the like. One of skill in the art can readily detect these signals using a fluorescence microscope, a scintillation counter, a light or radioactively sensitive photoemulsion, a light microscope, a spectrophotometer or other means. When an environmentally-sensitive functional molecule is used, the signal can change in lifetime, strength, color or other quality to signal interaction of the functional molecule with the environment. For example, when the environmentally-sensitive functional molecule is a fluorescent dye, the signal change can be a color, wavelength, intensity or lifetime of fluorescence emitted by the dye. The change need only be detectable, for example, a change in wavelength of fluorescence of about 50 nm to about 300 nm can be readily detected. However, a change in wavelength of greater than about 10 nm is preferred. More preferably the change in wavelength is greater than 20 nm. In one embodiment the change in wavelength can vary from about 30 nm to about 200 nm.

Where convenient, a peptide, as opposed to a polypeptide or antibody, with an attached functional molecule may be a biosensor, for example, when the binding affinity and selectivity of the peptide is representative of the larger protein of which it is normally a part. Alternatively, the labeled peptide can be ligated into a polypeptide to form the protein or antibody of which it is normally a part using the methods described herein. In one embodiment, the peptide is incorporated onto one of the termini of a protein, for example, through procedures described in Curr. Op. Biotechnology 9:412 (1998) or Ann. Rev. Biochem. 57:957-89 (1988). In another embodiment, the peptide can be incorporated into the middle of a protein, for example, by using the procedures described in PNAS 95:6705 (1998).

Targets

As used herein, a "target" is any molecule, structure or complex that a peptide, polypeptide or antibody linked to a functional molecule by the present methods can interact with. Targets contemplated by the present invention include antigens, antibodies, proteins, enzymes, membrane proteins, endoplasmic reticulum proteins, structural proteins, major histocompatibility proteins, DNA binding proteins, receptors, ligands, cofactors, nucleic acids, kinases, GTPases, ATPases, proteins involved in motility and the like. Targets may undergo structural changes and other types of changes, for example, phosphorylation, de-phosphorylation, conformational changes, ligand binding, co-factor binding, activation, post-translational modification, carbohydrate or sugar attachment, membrane interactions and the like. Specific targets include calmodulin, Rho GTPases, rac, cdc42, mitogen-activated protein kinase (MAP kinase), Erk1, Erk2, Erk3, Erk4, IgE receptor ($F_c$□RI) actin, α-actinin, myosin, and major histocompatibility proteins.

Targets can have "tag" sequences that permit binding of a biosensor or labeled polypeptide to the target. As used herein, a "tag" is any binding site for a biosensor. In general, a tag is a peptide or polypeptide segment that is recognized by the biosensor and to which the biosensor will bind with sufficient binding affinity to permit detection and/or visualization of the target. Any protein binding domain or ligand binding site of a receptor can be used. Thus, a tag can be, for example, an antigenic epitope to which an antibody can bind, a part of a leucine-zipper to which another part of a leucine zipper can bind, a domain of a homeotic protein that mediates binding to a DNA site, receptor-ligand binding site.

The dimerizing domain from yeast GCN4 protein can also be used to form a tag-biosensor dimer. The GCN4 dimerizing domain is a single α-helix which pairs with its partner to form a parallel coiled-coil (O'Shea, Rutkowski, Stafford and Kim, Science, 245, 646, (1989)). The X-ray crystal structure of the GCN4 coiled-coil has been determined (O'Shea, Klemm, Kim and Alber, Science, 254, 539, (1991)), and factors affecting stability and oligomerization state of native and mutant GCN4 coiled-coil peptides have been determined (Harbury, Zhang, Kim and Alber, Science, 262, 1401, (1993); O'Neil, Hoess and DeGrado, Science, 249, 774, (1990)). In addition, several model coiled-coil peptides have been extensively studied and rules governing stability of these designed peptides have been reported (Hodges, Zhou, Kay and Semchuk, Peptide Res., 3, 123, (1990); Zhu et al., Int. J. Peptide Protein Res., 40, 171, (1992); Lumb and Kim, Biochemistry, 34, 8642, (1995)).

Another useful tag-biosensor dimer can be formed from the binding domain from the Arc repressor of bacteriophage P22 (Schildbach, J F, Milla M E, Jeffrey P D, Raumann B E, Sauer R T (1995). Biochemistry 34: 13914-19). Arc repressor is a dimeric polypepfide of 53 amino acids. A tag-biosensor dimmer can also be formed from the C-terminal tetramerizing domain from the tumor suppressor p53. The structure of this domain has been determined from the crystal Jeffrey, Gorina and Pavletich, Science, 267, 1498, (1995)) and in solution (Clore et al., Nature Struct. Biol., 2, 321, (1995)). The Mnt repressor of bacteriophage P22 (Waldburger, C. D. and R. T. Sauer (1995). Biochemistry 34(40): 13109-13116), the Mnt repressor polypeptide and streptavidin-avidin can be used to form tag-biosensor dimers. Streptavidin (Argarana, C., Kuntz, I. D., Birken, S, Axel, R. and Cantor, C. R. (1986) Nucleic Acids Res. 14:1871) and avidin (Green, N. M. (1975) Adv. Protein Chem. 29:85) are homologous tetrameric polypeptides of approximately 125-127 and 128 amino acids, respectively. Biotin ligase (BLS) can also be used to make a tag-biosensor dimmer. BLS polypeptide sequences have been described for various proteins: for example, the C-terminal 87 residues of the biotin carboxy carrier protein of *Escherichia coli* acetyl-CoA carboxylase (Chapman-Smith, A., D. L. Turner, et al. (1994). Biochem J. 302: 881-7). The C-terminal 67 residues of carboxyl-terminal fragments of human propionyl-CoA carboxylase alpha subunit may be used (Leon-Del-Rio, A. and R. A. Gravel (1994) J. Biol. Chem. 269(37): 22964-8); and residues 18-123 of *Propionibacterium freudenreichii* transcarboxylase 1.3S biotin subunit (Yamano, N., Y. Kawata, et al. (1992) Biosci. Biotechnol. Biochem. 56(7): 1017-1026).

Such tag sequences can be present naturally or can be added to the target by methods available to one of skill in the art. Different targets within a single cell can have different tags to which different biosensors can bind. This permits visualization of two or more targets within the same cell so that the interaction and dynamic interplay between targets can be observed in relation to other cellular structures. As described herein, biosensors can also be designed to undergo fluorescence resonance energy transfer (FRET) when they become juxtaposed at an appropriate distance. Similarly, a target can be engineered to have two different tags so that two different biosensors can bind to the same target. Tag sequences can be added to a target protein, for example, by protein ligation procedures described herein or by standard molecular biology techniques where a peptide or polypeptide is fused to another peptide or polypeptide. See, e.g., Sambrook, J., E. F. Fritsch, and T. Maniatis. 1989. *Molecular Cloning: A Laboratory Manual,* 2nd ed., Cold Spring Harbor Laboratory Press, Plainview, N.Y.).

Antigen and Antibody Targets

When antibodies are linked to functional molecules using methods of the present invention the target can be an antigen. Alternatively, an antigen or a peptide epitope can serve as a biosensor for an antibody target. The present invention contemplates use or detection of any antigen or antibody known to one of skill in the art as a target.

In general, a molecule must have sufficient complexity and sufficient molecular weight in order to act as an antigen. In order to have sufficient complexity, the antigen must have at least one epitope. As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

In order to have a sufficient molecular weight, the antigen generally must have a molecular weight that is greater than 2,000 daltons. Formerly, it was thought that the lower molecular weight limit to confer antigenicity was about 5,000 daltons. However, antigenicity has recently been demonstrated with molecules having molecular weights as low as 2,000 daltons. Molecular weights of 3,000 daltons and more appear to be more realistic as a lower limit for immunogenicity, and approximately 6,000 daltons or more is preferred.

In preparing antigens to produce antibodies for attachment to functional molecule, it is desirable to use antigens with a high degree of purity. Accordingly, it is desirable to use a purification process permitting isolation of the antigen from antigenically distinct materials. Antigenically distinct materials are undesired large molecules that may compete with the target antigen for antibody production thereby minimizing production of the desired antibodies or inducing cross-reactive antibodies of low specificity or affinity. The practice of the invention can accordingly include a number of purification steps using available techniques. Purification can, for example, be effected by size exclusion chromatography, ion exchange chromatography, dialysis, cold organic solvent extraction, gel electrophoresis and/or fractional crystallization means which are available to one of skill in the art. Preferably an antigen used for antibody preparation is at least about 90% pure and more preferably at least about 99% pure.

Removal of small molecule reactants and reaction products from the synthesized antigen is generally desirable. However, some small molecular substances may be useful, for example, for control of pH and salinity. Thus, a convenient end-product form in which to recover the antigen is, in a buffered aqueous solution that is suitable for direct administration to animals.

Antibodies

The present invention contemplates linkage of any available antibody to functional molecules. Such antibodies can be polyclonal or monoclonal antibodies. The term "antibody" as used in this invention is meant to include intact antibody molecules as well as fragments thereof, such as, for example, Fab and F(ab')$_2$, which are capable of binding to the antigen or its epitopic determinant.

Polyclonal antibodies can be raised by administration of an antigen of the invention to vertebrate animals, especially mammals such as goats, rabbits, rats or mice using known immunization procedures. Usually a buffered solution of the antigen accompanied by Freund's adjuvant is injected subcutaneously at multiple sites. A number of such administrations at intervals of days or weeks is usually necessary. A number of animals, for example from 3 to 20, are injected with the expectation that only a small proportion will produce desirable antibodies. However, one animal can provide antibodies sufficient for thousands of assays. Antibodies are recovered from animals after some weeks or months.

Exemplary immunogenic carrier materials can be used with the antigen to enhance the immune response. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyamino acid. See also, the carrier molecules and antibody production methods set forth in Cremer et al., "Methods in Immunology" (1963), W. A. Benjamin Inc., New York, pp. 65-113 and Harlow and Lane, "Antibodies: A Laboratory Manual" (1988), Cold Spring Harbor Laboratory, New York, p. 5. These disclosures are herein incorporated by reference.

A preferred class of natural carrier materials is the proteins. Proteins can be expected to have a molecular weight in excess of 5,000 daltons, commonly in the range of from 34,000 to 5,000,000 daltons. Specific examples of such natural proteins are hen ovalbumin (OA), bovine serum albumin (BSA), keyhole limpet hemocyanin (KLH), horse gammaglobulin (HGG), and thyroglobin.

Exemplary of synthetic carrier is the polyamino acid, polylysine. Where the synthetic antigen comprises a partially antigenic carrier conjugated with a hapten, it will generally be desirable for the conjugate to have a molecular weight in excess of 6,000 daltons, although somewhat lower molecular weights may be useful. Preferably, the natural carrier has some solubility in water or aqueous alcohol. Desirably, the carriers are nontoxic to the animals to be used for generating antibodies.

The carrier can be coupled to antigens by any available means, included the procedures provided herein. Preferably, a carrier moiety has a plurality of hapten or antigen moieties coupled to it, for example, about 15 to 30 for a protein of 100,000 daltons. While steric hindrance and reduced structural complexity may reduce the number of haptens or antigens attached to the carrier, the maximum number is preferred. For example, up to about 25 to about 50 hapten moieties can be coupled to BSA carriers.

The use of monoclonal antibodies as biosensors of this invention is preferred because monoclonal antibodies are homogeneous and can be continuously produced in large quantities. Monoclonal antibodies are prepared by recovering lymph node or spleen cells from immunized animals and immortalizing the cells in conventional fashion, e.g., by fusion with myeloma cells or by Epstein-Barr virus transformation. Clones expressing the desired antibody are identified by screening cell line media for reactivity with the antigen used to immunize the animals. One of skill in the art can use readily available methods to make monoclonal antibodies, for example, by using the hybridoma technique described originally by Koehler and Milstein, Eur. J. Immunol., 6:511 (1976), by Hammerling et al., in "Monoclonal Antibodies and T-Cell Hybridomas", Elsevier, N.Y., pp. 563-681 (1981), and by Zola, in "Monoclonal Antibodies: A Manual of Techniques", CRC Press, Boca Raton, Fla. (1987). The hybrid cell lines can be maintained in vitro in cell culture media. The cell lines producing the antibodies by these procedures can be selected and/or maintained in a medium containing hypoxanthine-aminopterin thymidine (HAT). However, once the hybridoma cell line is established, it can be maintained on a variety of nutritionally adequate media. Moreover, the hybrid cells lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant or ascites fluid by conventional methods such as immune precipitation, ion exchange chromatography, affinity chromatography such as protein A/protein G column chromatography, or the like. The antibodies described herein are also recovered from hybridoma cell cultures by conventional methods such as precipitation with 50% ammonium sulfate. If desired, the purified antibodies can then be sterile filtered before use.

The term "monoclonal antibody" as used herein refers to any antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The monoclonal antibodies herein also include hybrid and recombinant antibodies produced by splicing a variable (including hypervariable) domain of an anti-adduct antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$ and Fv), so long as they exhibit the desired biological activity. See e.g. Cabilly et al. U.S. Pat. No. 4,816,567; Mage and Lamoyi, "Monoclonal Antibody Production Technique and Applications", pp. 79-97 (Marcel Dekker, Inc., New York, 1987).

Thus, the modifier "monoclonal" indicates the character of the antibody as being obtained from a substantially homogenous population of antibodies, and is not to be construed as requiring production of the antibody by any particular method. For example, the monoclonal antibodies to be used in accordance with the present invention may be made by the hybridoma method described by Koehler and Milstein, supra, or may be made by recombinant DNA methods (Cabilly, et al. supra).

In one embodiment, the biosensor antibodies or the present invention are used for diagnostic or imaging purposes in vivo, within a mammalian subject. While the in vivo use of a monoclonal antibody from a foreign donor species in a different host recipient species is usually uncomplicated, an adverse immunological response by the host to antigenic determinants present on the donor antibody can sometimes arise. In some instances, this adverse response can be so severe as to curtail the in vivo use of the donor antibody in the host. Further, the adverse host response may serve to hinder the intercellular adhesion-suppressing efficacy of the donor antibody. Methods to avoid such adverse reactions are available. For example, humanized antibodies or chimeric antibodies (Sun, et al., Hybridoma, 5 (Supplement 1):S17, 1986; Oi, et al., Bio Techniques, 4(3):214, 1986) can be used. Chimeric antibodies are antibodies in which the various domains of the antibodies' heavy and light chains are coded for by DNA from more than one species. Typically, a chimeric antibody will comprise the variable domains of the heavy ($V_H$) and light ($V_L$) chains derived from the donor species producing the antibody of desired antigenic specificity, and the constant domains of the heavy ($C_H$) and light ($C_L$) chains derived from the host recipient species. It is believed that by reducing the exposure of the host immune system to the antigenic determinants of the donor antibody domains, especially those in the $C_H$ region, the possibility of an adverse immunological response occurring in the recipient species will be reduced. Thus, for example, it is possible to produce a chimeric antibody for in vivo clinical use in humans which comprises mouse $V_H$ and light $V_L$ domains coded for by DNA isolated from ATCC HB X, and $C_H$ and $C_L$ domains coded for with DNA isolated from a human leukocyte.

The present invention further provides a composition comprising an antibody with a functional molecule attached by the methods of the present invention and a suitable carrier. Further, the present invention also provides a therapeutic composition comprising an effective amount of the antibody-functional molecule conjugate produced by the present methods and a pharmaceutically acceptable carrier.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid R™. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

Methods of Using Biosensors

Biosensors of the invention can be used in vitro or vivo. Biosensors can be used with any type of test sample, such as cultured cells, tissue samples, cell suspensions, cell lysates, partially purified isolates of a potential target and purified isolates of a potential target. A sample that includes cells can be in any form convenient for observation of the target, for example, cells plated on a culture dish, cells on a microscope slide, suspensions of cells, tissues in physiological or culture media or tissues on a microscope slide In general, the biosensor is contacted with a sample that may contain a target of interest under conditions and for a time sufficient to permit interaction or binding of the biosensor to the target of interest. The biosensor can be contacted with sample that is in solution by simply mixing the biosensor into the solution. When the target is in a cell or tissue, the biosensor can be injected into the cell or tissue. In some experiments placing the needle into the region just adjacent to the nucleus produced a good combination of efficient injection and cell health. Alternatively, the cell or tissue can be transfected or transformed with a nucleic acid capable of expressing the biosensor. One of skill in the art can use readily available procedures for injecting and transfecting cells with such biosensors.

Conditions sufficient to permit interaction of the biosensor with target are generally conditions that permit protein-protein interactions. A temperature sufficient to permit protein-protein interactions is a temperature that maintains and encourages secondary and tertiary polypeptide structure formation. For example, the temperature can be about 4° C. to about 40° C., and preferably a temperature of about 4° C. to about 37° C. When the sample includes cells, the temperature is preferably a temperature which maintains cellular function, for example, a temperature of about 20° C. to about 38° C. A time sufficient for interaction of the biosensor with a target can be determined by one of skill in the art. Such a time can be, for example, about 1 minute to about 2 hours, preferably about 3 minutes to about one hour. In one experiment, visualization of biosensor-target interaction was successfully performed after cells were given about 5-10 minutes to recover after injection.

The invention will now be illustrated by the following non-limiting Examples.

EXAMPLE 1

Site-Specific Labeling of a Secondary Aminooxy Group

Figure 1:
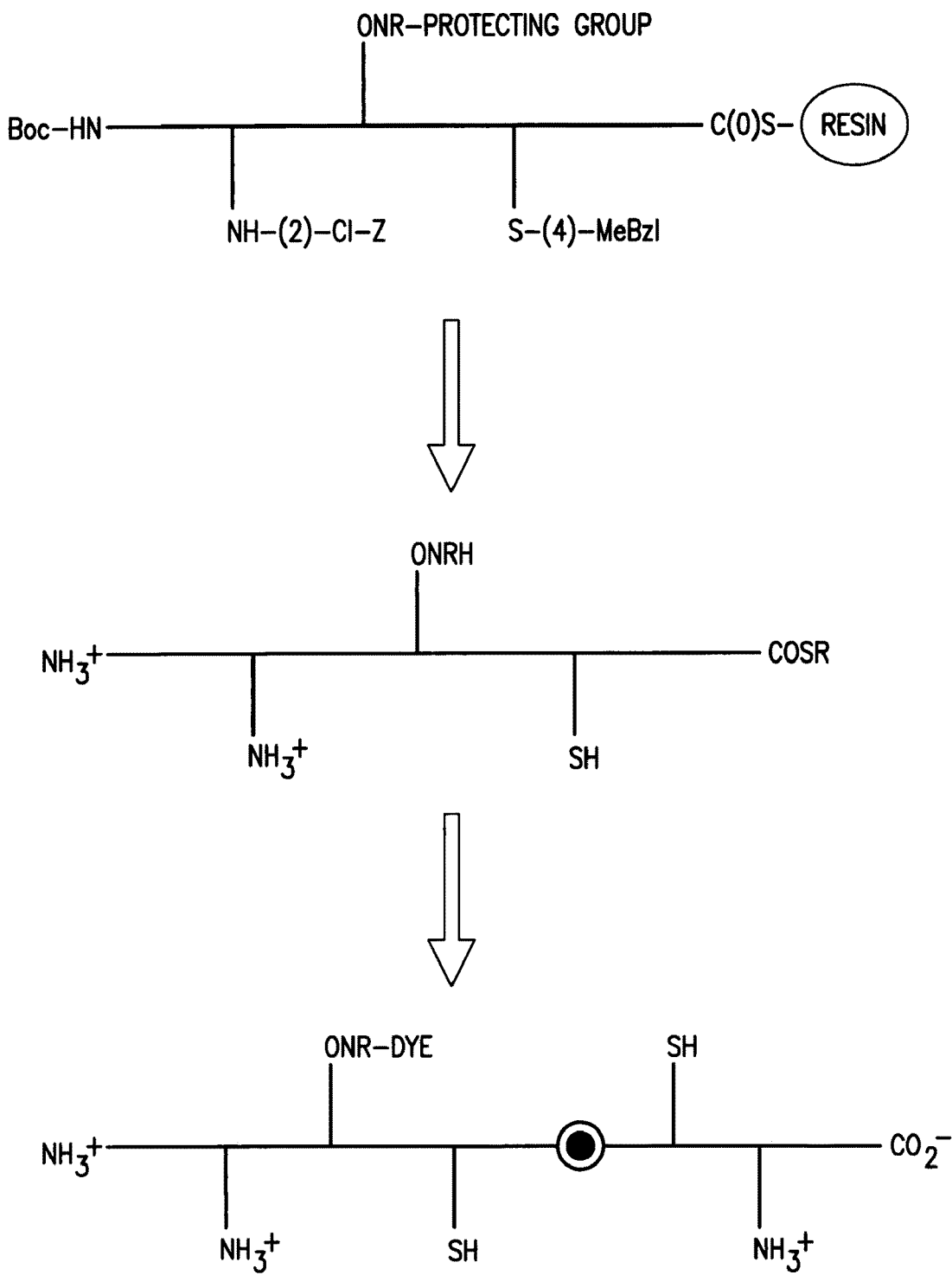
FIG. 1 illustrates a general strategy for site-specific labeling of polypeptides. The protected aminooxy group is incorporated during solid-phase peptide synthesis (synthesis on a thioester-linker resin is shown); cleavage from the resin generates a peptide possessing unprotected sidechains, an aminooxy group and a C-terminal thioester; and ligation and subsequent site-specific labeling produces the full-length peptide with a functional molecule attached at the aminooxy nitrogen.

Under controlled pH conditions, the low pKa and enhanced nucleophilicity of an aminooxy group relative to other nucleophilic side chains found in peptides suggested the possibility of site-specific reaction with standard electrophiles such as succimidyl esters (FIG. 1). While selective labeling of a primary aminooxy group in the context of an unprotected peptide was achieved, extensive attempts to utilize the primary aminooxy group during synthesis failed. Even when protected as the 2-chlorobenzyloxycarbonyl carbamate, deprotonation of the primary aminooxy group allowed rapid acylation, so it could not be readily incorporated during peptide synthesis. Thus, under certain conditions, the use of a secondary aminooxy group may be preferred.

Figure 2:
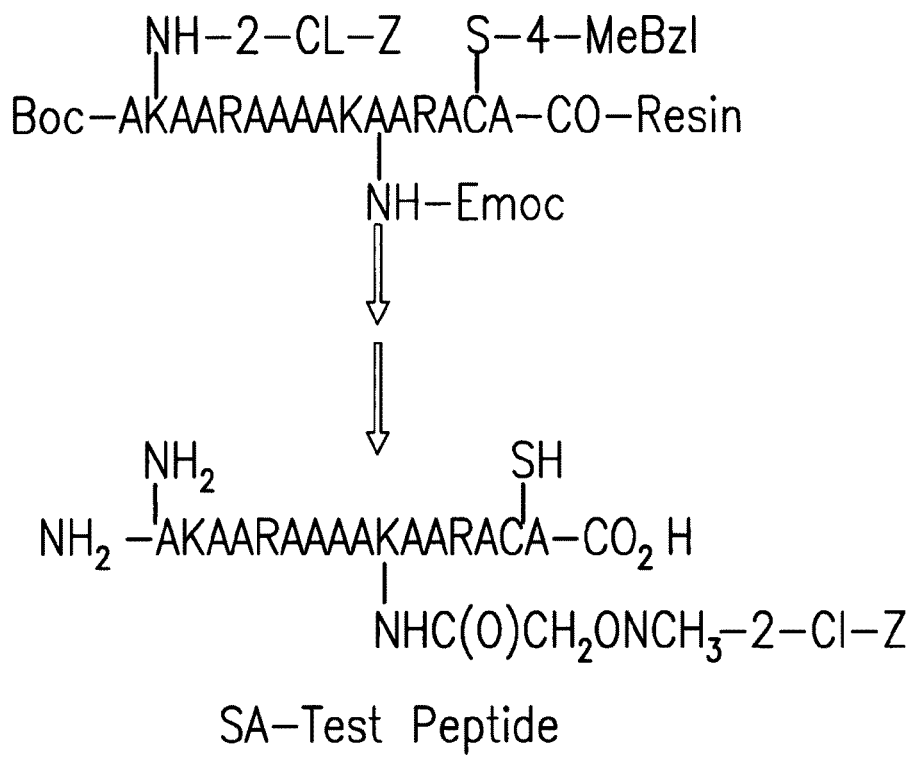
FIG. 2 illustrates the synthesis of PA-test and SA-test peptides.

A test peptide containing both a secondary aminooxy group and nucleophilic amino acids that were most likely to interfere with selective labeling at the aminooxy nitrogen (lysine, cysteine, and the amino-terminus) was prepared. As illustrated in FIG. 2, $NH_2$-AKAARAAAAK*AARACA-$CO_2H$ (SEQ ID NO: 2), here designated SA-test peptide, was synthesized by incorporation and deprotection of N-(2-Cl-benzyloxycarbonyl)-N-methylaminooxy acetic acid (FIG. 4, 3) during solid phase peptide synthesis. The reactivity of the protected secondary aminooxy group was sufficiently attenuated to remain unreactive during Boc solid-phase peptide synthesis on thioester-linker resins. The 2-Cl-Z protection for the N-methylaminooxy amino acid was efficiently removed by standard HF cleavage procedures.

Conditions for selectively labeling the secondary aminooxy group were determined by varying the reaction pH and dye stoichiometry. Labeling with the succinimide ester of tetramethylrhodamine (TMR-OSu) was determined to be optimal in a solvent system consisting of 50% DMSO/50% aqueous acetate buffer at pH of 4.7 with 2 equivalents of dye per mole of peptide (Table 1). The crude reaction products were separated from unreacted dye, and characterized by RP-HPLC and ESI-MS. Under these conditions, a single molecule of dye was incorporated on the aminooxy group with a 78% yield, based on HPLC quantification. However, side reaction products were also isolated and determined to be either SA-test peptide labeled with two dye molecules (~13%) or acetylated peptide products (~5%). The selectivity, as defined by the ratio of the peak areas of desired single-labeled product over double-labeled products, was 6/1 (Table 1).

It was determined that many of the side reactions occurred during size exclusion chromatography in the ammonium bicarbonate solvent used to separate reaction products. Using an acidic solvent system, 0.1% TFA, virtually eliminated multiply labeled side products leading to considerable improvements in both selectivity and yield. Including a mild reducing agent, tris(2-carboxyethyl)phosphine (TCEP), in the reaction buffer also significantly curtailed several minor side reactions revealed by HPLC, especially disulfide formation. Labeling and gel filtration under these optimized conditions produced a 70% recovered yield of labeled SA-test peptide (90% yield based on HPLC quantitation), 90% of which was labeled with only a single dye at the aminooxy amine. The labeling selectivity was increased to 22/1 (Table 1).

Figure 3:
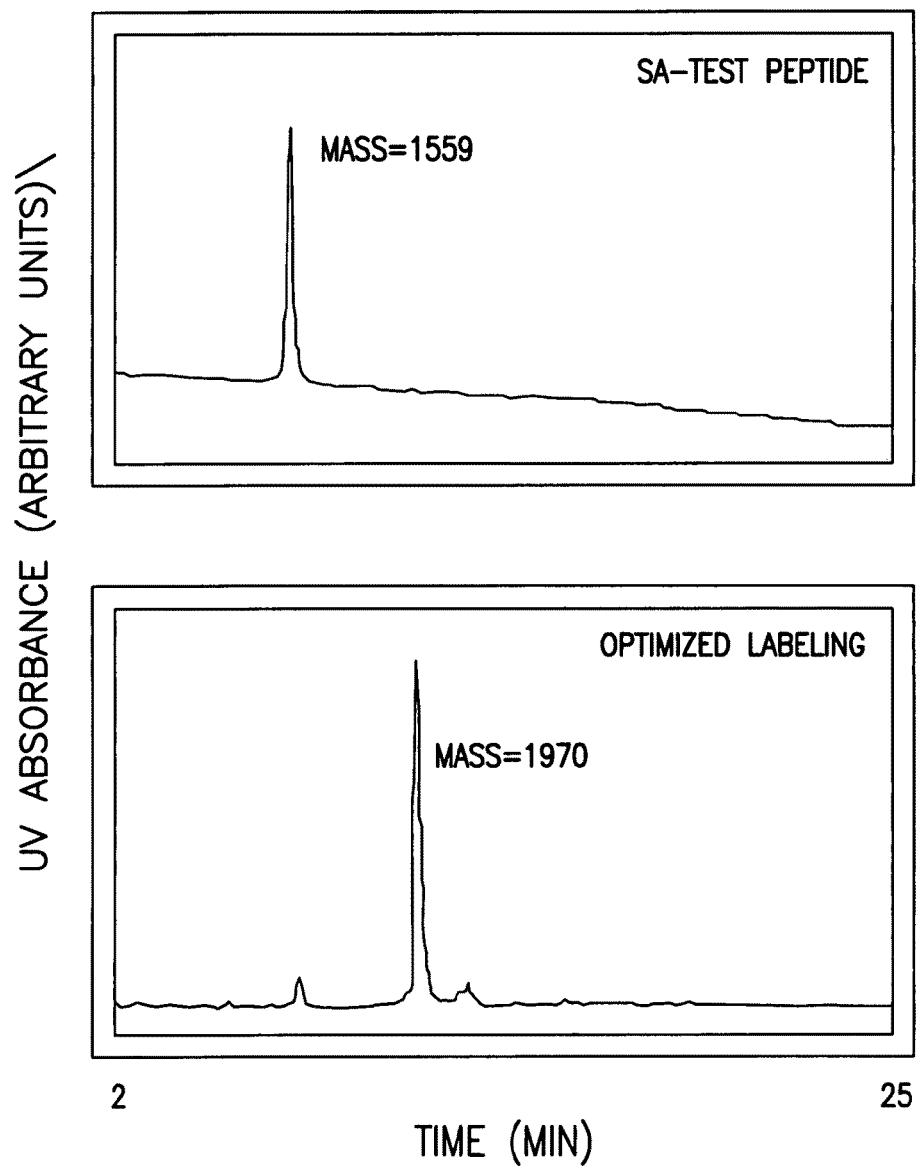
FIG. 3 shows HPLC analysis of purified SA-test peptide (top) and crude reaction products from optimized labeling conditions (bottom).

The purity of the product was confirmed using RP-HPLC, mass spectroscopy, further chemical reaction, and isolation of purposefully overlabeled products. The labeled peptide eluted as a single peak under all HPLC conditions tested with a mass consistent with that predicted for singly-labeled SA-test peptide (Mass=1970). To determine that the labeling site was indeed at the N-methylaminooxy group, a selective zinc/acetic acid reduction procedure was used to cleave the N—O bond (FIG. 3). HPLC of the reduction reaction showed >98% conversion of the starting material and a new earlier eluting peak. The mass of this peak (1530 amu) corresponded to the predicted mass of the unlabeled SA-test peptide cleaved at the aminooxy N—O bond. The residual zinc was washed several times with a saturated solution of EDTA in water, which demonstrated that the reduction reaction was complete.

To eliminate the unlikely possibility that the HPLC peak containing isolated single-labeled SA-test peptide product was a mixture of two labeled species, SA-test peptide was reacted under higher pH conditions (pH 9.0) to label all reactive sites. SA-test peptide contained 3 nucleophilic labeling sites which would be irreversibly labeled: aminooxy, lysine, and N-terminal amine. Dye labeling at high pH generated a mixture of peptides labeled at all possible combinations of sites with 1, 2 or 3 dyes. HPLC analysis of this reaction mixture showed 8 peaks, indicated by ESI-MS to correspond to unreacted SA-test peptide, SA-test peptide single-labeled at the aminooxy nitrogen, and six additional peaks corresponding to two single-labeled peptides, three peptides bearing two dyes and a single triply-labeled peptide species. This experiment revealed the HPLC retention times of all these products, none of which co-eluted with the peak identified as SA-test peptide labeled with a single dye on the secondary aminooxy nitrogen.

TABLE 1

Labeling of SA-Test Peptide

| Reaction | Buffers | | TCEP | pH* | Dye Equivalents | Percentage | | | Selectivity |
| | Gel Filtration | | | | | SM | 1 Dye | 2 Dye | |
| --- | --- | --- | --- | --- | --- | --- | --- | --- | --- |
| Acetate | $(NH_4)HCO_3$ | | No | 4.7 | 1.0 | 32 | 56 | 7 | 8:1 |
| Acetate | $(NH_4)HCO_3$ | | No | 4.7 | 1.5 | 14 | 63 | 13 | 4.5:1 |
| Acetate | $(NH_4)HCO_3$ | | No | 4.7 | 2.0 | 0 | 78 | 13 | 6:1 |
| Acetate | $(NH_4)HCO_3$ | | No | 4.7 | 2.4 | 0 | 76 | 17 | 4.5:1 |
| Acetate | $(NH_4)HCO_3$ | | No | 4.7 | 3.0 | 0 | 71 | 23 | 3:1 |
| Citrate | 0.1% TFA | | Yes | 4.7 | 4.3 | 4.3 | 89.6 | 4.1 | 22:1 |
| Carbonate | 0.1% TGA | | Yes | 9.0 | 0.99 | 13 | 85 | 0 | 51:1** |

Site-specific labeling of the aminooxy group could even be achieved at basic pH (Table 1). Using pH 9.0 carbonate buffer in our solvent system, addition of 0.5 equivalents of dye produced, after 3 hours, ~50% conversion of the starting SA-test peptide to a single peak with the elution time of the desired singly-labeled product. After addition of another 0.5 equivalents of TMR-OSu and an additional 3 hours of reaction time, HPLC showed ~85% conversion to a peak with the retention time of the desired product. Two minor peaks (~2-3% of total peak area), were also apparent and corresponded to the two other single-labeled SA-test peptide species identified in the multiple labeling experiment above. The N-hydroxysuccinimide ester of rhodamine clearly showed selective reactivity with the aminooxy group.

The selectivity observed at higher pH cannot be explained by the nucleophilicity of the aminooxy group alone. In fact, others have shown that at, in an uncatalyzed reaction with phenyl acetate at high pH, amines are more reactive than O-alkyl aminooxy groups. Therefore we suggest that kinetic factors are contributing to the selective reactivity of the N-methylaminooxy group, even when competing groups are not protonated. Possible reasons for this include: (1) the aminooxy oxygen localizes the nitrogen near the activated ester via formation of a hydrogen bonded "bridged" intermediate (2) a base catalyzed reaction pathway under the conditions of our reaction. This exceptional reactivity has important practical implications, as it can allow the selective labeling of acid-labile polypeptides and synthetic proteins under physiological or basic conditions.

EXAMPLE 2

The Secondary Aminooxy Group is Compatible with $C^\alpha$-Thioesters and Amide-Forming Ligation Preparation of proteins by total chemical synthesis often requires the ligation of large polypeptides prepared by solid-phase peptide synthesis on thioester-linker resins. The most generally applicable methods available for ligations are native chemical ligation and expressed protein ligation. These processes utilize the same basic chemistry to join two peptides, one with an N-terminal cysteine and the other with a C-terminal thioester, through a regiospecific and site-specific reaction to generate a larger polypeptide. The application of aminooxy-labeling chemistry to the synthesis of large polypeptides and proteins requires compatibility with these solid-phase peptide synthesis and ligation chemistries.

Figure 4:
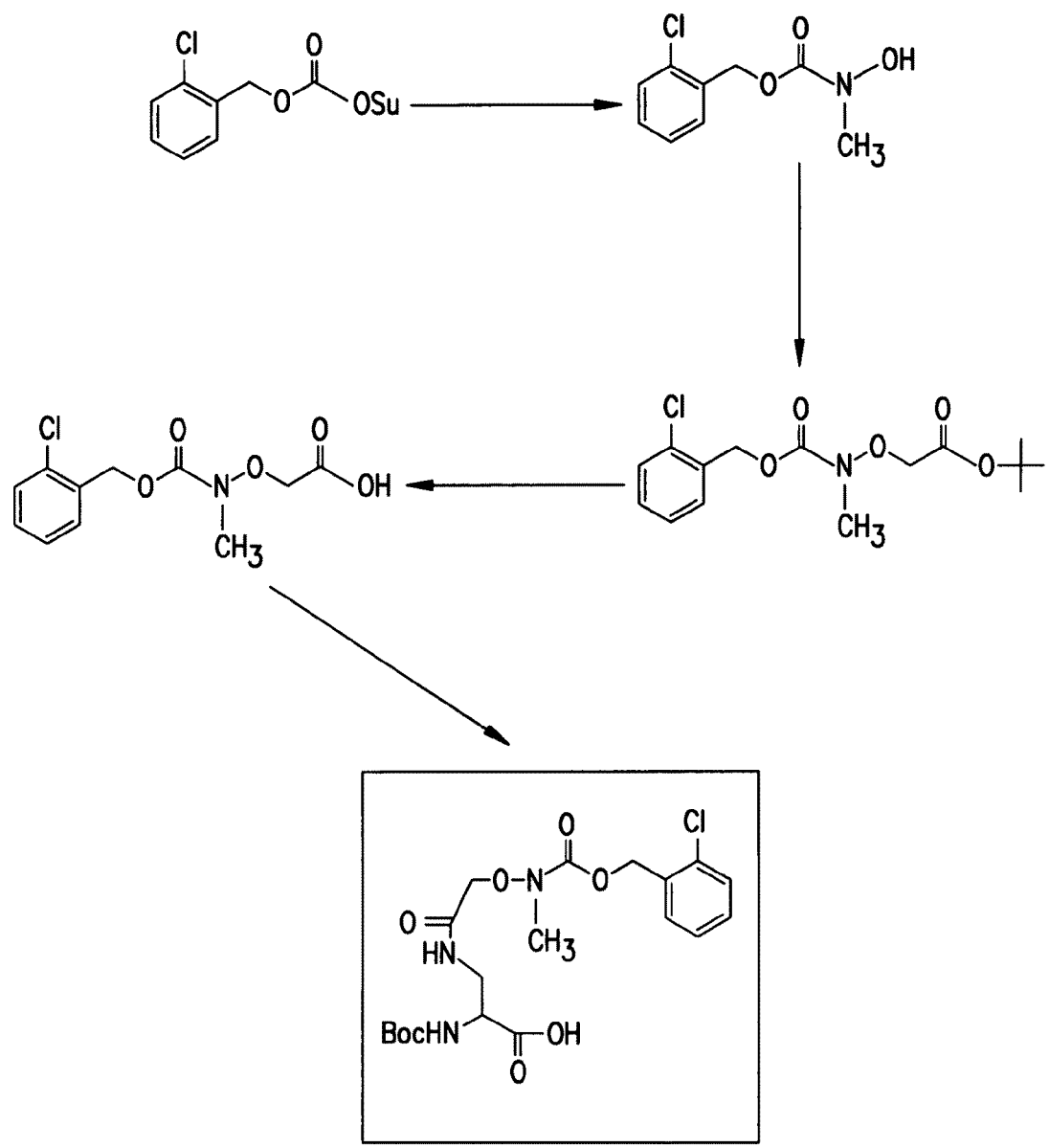
FIG. 4 illustrates the synthesis of a protected intermediate (4) of the invention.

The optimal approach for utilizing aminooxy-labeling chemistry in the chemical synthesis of proteins is direct incorporation of the aminooxy group as part of an amino acid used during standard solid-phase peptide synthesis. For this purpose, we generated a suitably protected N-methylaminooxy amino acid, $\alpha$-Boc-$\beta$-[N-(2-Chlorobenzyloxycarbonyl)-N-Methylaminooxy Acetyl]-$\alpha,\beta$-Diaminopropionic Acid [Boc-2-Cl-Z-(SA)Dapa-OH] (4), as shown in FIG. 4. This amino acid, referred to as SAOD, was incorporated into the peptide sequence LY-(SAOD)-AG-MPAL thioester by synthesis on TAMPAL thioester-linker resin, as described below in the Methods. (MPAL is the C-terminal mercaptopropionyl-leucine group generated by cleavage of a peptide from TAMPAL resin, see Hojo, H., et al., *Bull. Chem. Soc. Jpn.* 1993, 66:2700-2706; and Hackeng, T. M. et al., *Proc. Natl. Acad. Sci. USA*. In press)

Ligation of the LY-(SAOD)-AG-MPAL (SEQ ID NO: 3) thioester peptide with the peptide CRANK-NH$_2$ (SEQ ID NO: 4), was tested using standard procedures employing phosphate buffer with 6M guanidine hydrochloride at neutral pH in the presence of 2-3% thiophenol by volume. The ligation proceeded over 24 hours and generated the desired ligation product, LY-(SAOD)-AGCRANK-NH$_2$ (SEQ ID NO: 5), at ~85% yield. The major side product was attributable to modification of unligated CRANK-NH$_2$ peptide under the ligation conditions (mass=714.5, data not shown), and was not related to the presence of the aminooxy group. There was also a single time-dependent side reaction, which generated a product of 14 mass units lower than the desired. Using high concentrations of reacting peptides and isolating the ligation product after 24 hours reduced this side reaction to acceptable levels (<5%).

The ligation of a peptide containing multiple potentially reactive functional groups, including a hexahistidine tag useful for affinity chromatography was also tested. Coupling CEYRIDRVRLFVDKLDNIAQVPRVGAA-HHHHHH (SEQ ID NO: 6) to LY-(SAOD)-AG-MPAL thioester proceeded to completion in 5 hours with minimal side reactions. In both ligation reactions, there was less than 1% LY-(SAOD)-AG-MPAL self condensation product, indicating that the aminooxy group and thioester do not appreciably react with one another under the ligation conditions. These results demonstrate that the inclusion of an unprotected aminooxy group in the peptide chain is compatible with native chemical ligation.

Labeling of the two ligation products using tetramethylrhodamine succinimide ester proceeded with selectivity similar to that for the SA-test peptide. HPLC integration indicated that the product of the LY-(SAOD)-AG-MPAL ligation with CRANK-NH$_2$ was labeled with greater that 95% efficiency and with a selectivity of 34:1. Mass spectral analysis and zinc reduction demonstrated labeling at only the aminooxy group. For the longer hexahistidine-containing polypeptide ligation product, selectivity for the aminooxy group was greater than 10:1, but it was difficult to achieve high yields. The histidines could potentially have been affecting yield and selectivity by catalyzing nucleophilic attack on the succinimide ester of the reactive dye. Inclusion of guanidine hydrochloride in the reaction solvent increased the yield to approximately 50%, indicating that folding or poor solubility of the peptide was a factor in preventing access of the reactive dye to the aminooxy group. Selectivity was also improved, presumably because of the availability of the reactive secondary aminooxy group. Single-site labeling at the aminooxy group was proven by mass spectral analysis of trypsin and $\alpha$-chymotrypsin digests of the labeled polypeptide product.

EXAMPLE 3

Specificity of Labeling in Protein Domains Containing Aminooxy Amino Acids

As a control to establish the selectivity of labeling for aminooxy amino acid, the labeling of native $\beta$-Lactoglobulin with tetramethylrhodamine N-hydroxysuccinimide ester was attempted. It was found that non-specific labeling of this 162 aa protein containing 15 lysines and 4 cysteines was minimal (<1%), even after 6 hours.

Finally, the GTPase binding domain of p21 activated kinase (45 aa, 4 lys, 1 cys) with a secondary aminooxy amino acid incorporated at the amino-terminus (SAOD-PBD) was prepared. Previous experiments have demonstrated that PBD domains labeled with fluorescent reporter dyes at this terminus could be used as biosensors of GTPase activation. Labeling of PBD using the new methodology would enable the production of sufficient quantities to apply the biosensors in vivo and in pharmaceutical screening applications, and would allow incorporation of sensitive detectable groups enabling applications within living cells.

SAOD-PBD was readily labeled with Alexa-532 N-hydroxy-succinimide ester by titration addition of dye at pH 4.7 over 72 hours. The labeling efficiency was commensurate with that reported for the longest model peptide (50% yield by HPLC quantitation) and there was no indication of multiple labeling. In this case, isolation of labeled SAOD-PBD by RP-HPLC proved difficult. Separation to baseline resolution was not achieved, but small quantities of unlabelled PBD in the labeled product do not preclude the use of the labeled material in biosensor applications. Previous reports indicate that separation of labeled product from starting polypeptide is highly dependent on the specific peptide and the attached dye.

These results demonstrate that the optimized site-specific labeling chemistry reported here is compatible with the steps required for the preparation of proteins by total chemical synthesis.

EXAMPLE 4

Materials and Methods

General: For column chromatography, silica gel (230-400 mesh) was used in standard glass columns with gravity or air pressure. Reversed-phase high performance liquid chromatography (RP-HPLC) was performed on a Waters HPLC system with UV detection at 214 nm using either a Vydac C-18 analytical column (5 µm, 0.46×25 cm), a Waters RCM 8×10 module equipped with a semi-preparative Delta Pack C-18 Radial Pack cartridge column (15 µm, 8×100 mm) from Millipore, or a Vydac C-18 preparative scale column (15 µm, 1.0×25 cm). Linear gradients of solvent B (0.09% TFA in 90% acetonitrile/10% water) in solvent A (0.1% TFA in water) were used for all HPLC chromatographic separations.

Mass spectra of peptides were obtained either with a Sciex API-III electrospray ionization (ESI) triple-quadrupole mass spectrometer (PE Biosystems, Foster City), or matrix assisted laser desorption ionization time-of-flight (MALDI-TOF) instruments from Thermo Bioanalysis (Thermo Bioanalysis, LTD., UK) or Kratos Analytical (Chestnut Ridge, NY.). For ESI-MS, the observed masses reported were derived from the experimental m/z states for all observed charge states of a molecular species using the program MacSpec (Sciex, version 2.4.1) for electrospray mass spectrometry. MALDI-MS observed masses were relative to internal calibration using α-cyano-hydroxycinnammic acid or sinipinic acid matrices. Calculated masses reported were derived from either MacProMass (Terry Lee and Sunil Vemuri, Beckman Research Institute, Duarte, Calif.) or PAWS (Version 8.1.1, ProteoMetrics) and reflect the average isotope composition of the singly-charged molecular ion. Proton nuclear magnetic resonance spectrometry was recorded on a Bruker AC-250 mass spectrometer and data was analyzed using WinNMR (Bruker Instruments). Ultraviolet-Visible spectroscopy was performed on a Hewlett-Packard photodiode-array spectrophotometer.

Boc-L-amino acids were purchased from Novabiochem (La Jolla, Calif.) or Bachem Bioscience, Inc. (King of Prussia, Pa.). [[4-(Hydroxymethyl)phenyl]-acetamido]methyl (—$OCH_2$-Pam) Resin was purchased from PE Biosystems (Foster City, Calif.) and methylbenzhydrylamine (MBHA) resin was purchased from Peninsula Laboratories, Inc. (San Carlos, Calif.). Solvents were Synthesis grade or better and were purchased from Fisher Scientific (Tustin, Calif.). Trifluoroacetic acid (TFA) and anhydrous hydrogen fluoride were purchased from Halocarbon (New Jersey) and Matheson Gas (Rancho Cucamonga, Calif.). Dyes were obtained from Molecular Probes (Eugene, Oreg.). All other reagents were analytical grade or better and were purchased from Aldrich (Milwaukee, Wis.), Lancaster (Windham, N.H.), Peptides International (Louisville, Ky.) or Richelieu Biotechnologies (Montreal, Canada).

Peptide Segment Synthesis. Synthesis of peptides was carried out manually using optimized stepwise solid-phase synthesis methods with in situ neutralization and HBTU activation procedures for Boc chemistry on either —$OCH_2$-Pam, MBHA, or Trt-protected mercaptopropionyl-Leu (TAMPAL) resin (Hojo, H., et al., *Bull. Chem. Soc. Jpn.* 1993, 66:2700-2706; Hackeng, T. M. et al., *Proc. Natl. Acad. Sci. USA*. In press; and Schnolzer, M., et al., *Int. J. Peptide Protein Res.* 1992, 40:180-193). Standard Boc protecting group strategies were employed. Coupling was monitored by quantitative ninhydrin assay after 15 minute coupling cycles. After chain assembly, standard deprotection and cleavage from the resin support was carried out by treatment at 0° C. for 1 hour with anhydrous HF containing either 10% p-cresol or anisole as scavenger. Purification was performed using RP-HPLC.

Synthesis of TAMPAL Resin (Hojo, H., et al., *Bull. Chem. Soc. Jpn.* 1993, 66:2700-2706). 2.5 grams of MBHA resin (0.865 mmol/g, 2.16 mmol of amine) was swelled in DMF. Boc-Leu-OH (1.1 grams, 4.4 mmol) was activated with HBTU (8 ml, 0.5M solution) and DIEA (2 ml), then coupled to the MBHA resin until complete reaction by ninhydrin assay. The $N^\alpha$-Boc group of the linked leucine was removed with neat TFA, then S-Trt-β-mercaptopropionic acid (1.5 grams, 4.3 mmol), activated in the same manner as Boc-Leu-OH, was added to the deprotected Leu-MBHA resin and allowed to couple until complete reaction. The S-Trt-β-mercaptopropionyl-Leu-MBHA resin was washed extensively with DMF, then DCM/MeOH (1/1), and finally dried in vacuo to yield 3.39 grams of thioester resin. Substitution calculated by weight gain yielded 0.549 mmol/gram.

Deprotection of TAMPAL Resin: S-trityl protection was removed by two 5 minute treatments with 95% TFA/5% triisopropylsilane. The deprotected resin was extensively with DMF before coupling the first amino acid, activated using optimized in situ neutralization protocols.

Synthesis of N-(2-Cl-benzyloxycarbonyl)-N-Methylhydroxylamine (1) (Jencks, W. P., Carriuolo, J. *J. Am. Chem. Soc.* 1960, 82:675; Jencks, W. P. *J. Am. Chem. Soc.* 1958, 80:4581, 4585). N-methylhydroxylamine hydrochloride (0.95 g, 11.37 mmol) was dissolved in 3 ml of water with rapid stirring. The pH of this solution was adjusted to 6-7 by dropwise addition of a saturated solution of sodium bicarbonate. 2-Chlorobenzyloxycarbonyl-N-hydroxysuccinimidyl carbonate (1.2 g, 4.23 mmol) was dissolved in 4 ml of THF and added slowly to the rapidly stirring solution of neutralized N-methylhydroxylamine. After stirring at room temperature for 14 hours, the reaction was quenched with 20 ml of saturated sodium bicarbonate and extracted three times with 20 ml ethyl acetate. The combined ethyl acetate layers were washed once with saturated sodium bicarbonate, dried over anhydrous sodium sulfate and the solvent was removed in vacuo to yield 0.77 g (3.77 mmol, 84%) of an off-white solid. TLC Rf=0.2 (Hex/EtOAc/AcOH 80/20/1). $^1$H NMR: 3.23(s, 3H), 5.25 (s, 2H), 7.24 (m, 2H), 7.37 (m, 2H). HRMS: Expected=216.0427, Observed=216.0425.

Synthesis of N-(2-Cl-benzyloxycarbonyl)-N-Methylaminooxy Acetic Acid-Tert-butyl ester (2) (Jerry March in Advanced Organic Chemistry, Third Edition. John Wiley & Sons, New York. 1989, pp 381; and Nyberg, D. D., Christensen, B. E. *J. Am. Chem. Soc.* 1957, 79:1222; Motorina, I. A., et al., *Synlett* 1996, 389). Compound 1 (0.96 g, 4.71 mmol) was dissolved at room temperature in 10 ml of THF with rapid stirring. Bromoacetate tert-butyl ester (1.05 g, 5.38 mmol) was added, then sodium iodide (1.5 g, 10.01 mmol) followed by DIEA (2.5 ml, 15.92 mmol). The reaction changed to an orange-yellow color after addition of sodium iodide. The reaction was quenched with 30 ml water after complete reaction (~3 hours) and extracted 3 times with ethyl acetate. The combined ethyl acetate layers were dried over sodium sulfate and the ethyl acetate was removed in vacuo. The resultant oily solid was purified by silica chromatography on 230-400 mesh silica gel using hexanes/ethyl acetate/acetic acid (80/20/1) to yield 1.40 g (4.29 mmol, 90%) of a pure yellow oil. TLC Rf=0.5 (Hex/EtOAc/AcOH 80/20/1). $^1$H NMR: 1.46 (s, 9H), 3.29 (s, 3H), 4.36 (s, 2H), 5.26 (s, 2H), 7.24 (m, 2H), 7.40 (m, 2H). HRMS: Expected Mass=330.1108, Observed Mass=330.1104.

Synthesis of N-(2-Cl-benzyloxycarbonyl)-N-Methylaminooxy Acetic Acid (3) (Bryan, D. B., et al., *J. Am. Chem. Soc.* 1977, 99:2353). Compound 2 (1.1 g, 3.30 mmol) was dissolved into 4 ml of DCM and, with rapid stirring, neat TFA (5 ml) was added dropwise over 2 minutes at room temperature. After 1 hour, the reaction was quenched with 20 ml water, extracted 3 times with DCM, and the combined DCM layers were dried over sodium sulfate. The DCM was removed in vacuo to yield 0.9 g (3.28 mmol, 99%) of an off-white solid. TLC Rf=0.2 (Hex/EtOAc/AcOH 80/20/1). 1H NMR: 3.23 (s, 3H), 4.50 (s, 2H), 5.32 (s, 2H), 7.28 (m, 2H), 7.40 (m, 2H). HRMS: Expected Mass=274.0482, Observed Mass=274.0479.

Synthesis of N-(2-Cl-benzyloxycarbonyl)-N-Methylaminooxyacetyl-α-Boc-α,β-Diaminopropionic Acid [(SA)Dapa-OH] (4) (Wahl, F., Mutter, M. *Tett. Lett.* 1996, 37:6861-6864; and Anderson, G. W., et al., *J. Am. Chem. Soc.* 1964, 86:1839). N-(2-Chlorobenzyloxycarbonyl)-N-Methylaminooxy Acetic Acid (3) (2.5 g, 9.2 mmol) was activated with N-hydroxysuccinimide (2.11 g, 2 equiv.) and DIC (1.440 ml, 1.0 equiv.) in 20 ml DCM. This reaction was rapidly stirred at room temperature for 2 hours prior to the addition of N$^\alpha$-Boc-α,β-diaminopropionic acid (2.3 g, 1.2 equiv.) and DIEA (3.20 ml, 2 equiv.). After 4 hours, the DCM solvent was removed in vacuo, and 50 ml ethyl acetate was added. The ethyl acetate layer was washed twice with 0.5M acetate buffer, pH=4.0, then twice with 0.1N sulfuric acid. The combined acid washes were then washed with 50 ml ethyl acetate. The combined ethyl acetate layers were dried over sodium sulfate, then concentrated in vacuo to yield a viscous yellow oily solid. This solid was subjected to 3 hexane precipitations from diethyl ether to yield 2.16 g (51% yield) of an off-white solid. TLC Rf=0.2-0.4 (Hex/EtOAc/AcOH 30/70/0.5). 1H NMR: 1.45 (s, 9H), 3.16 (s, 3H), 3.54 (d-of-t, 1H, J=14.3, 4.6 Hz), 3.93 (m, 1H, J=14.3, 7.5, 4.6 Hz), 4.31 (s, 0.5H), 4.38 (s, 1H), 4.45 (s, 1H), 4.51 (s, 0.5H), 5.34 (s, 2H), 5.97 (broad-d, 1H, J=7.3 Hz), 7.30 (m, 2H), 7.43 (m, 2H), 8.50 (broad-s, 1H). HRMS: Expected Mass=460.1487, Observed Mass=460.1480.

Synthesis of Secondary Aminooxy Test Peptide (SA-test peptide). The SA-test peptide, NH$_2$-AKAARAAAAK*AARACA-CO$_2$H, was synthesized with Lys 10 side chain Fmoc protection as described previously (Canne, L. E., et al., *J. Am. Chem. Soc.* 1995, 117:2998-3007). Incorporation of the secondary aminooxy group was accomplished by coupling 2-Cl-Z protected N-methylaminooxyacetic (300 mgs, 1.09 mmol) activated with Diisopropylcarbodiimide (157 ul, 1.00 mmol) and N-hydroxysuccinimide (140 mgs, 1.22 mmol) in 2 ml DCM for 1-2 hours, hen diluted with 2 ml DMF just prior to coupling to the ε-amino group of Lys 10. Optimized coupling, cleavage and purification protocols were utilized. Amino acid analysis was consistent with the desired peptide. Expected Mass=1560, Observed Mass=1559.

Synthesis of LY-(SAOD)-AG-MPAL-Thioester. LY-(SAOD)-AG-MPAL-Thioester was synthesized using optimized in situ neutralization protocols for Boc chemistry on TAMPAL resin. Coupling of the N$^\alpha$-Boc-(SA)Dapa-OH amino acid was accomplished by reacting the in situ activated N-hydroxysuccinimide ester to the deprotected amino-terminal nitrogen of alanine (Canne, L. E., et al., *J. Am. Chem. Soc.* 1995, 117:2998-3007). (SA)Dapa-OH (4) (230 mgs, 0.5 mmol) was dissolved in 1 ml DCM and N-hydroxysuccinimide (115.1 mgs, 1.0 mmol) and DIC (74.4 µl, 0.47 mmol) were added. The reaction was mixed briefly and allowed to activate for 1-2 hours at room temperature prior to coupling to the deprotected N-terminus of the peptide chain. After this coupling, no further modifications of the synthetic protocols were required. Expected mass=797, Observed mass=797.

Ligation of LY-(SAOD)-AG-MPAL-Thioester with CRANK-NH$_2$ Peptide. LY-(SAOD)-AG-MPAL-Thioester (3 mg, 3.8 µmol) was dissolved into 100 ul of 50 mM phosphate buffer containing 6M guanidine hydrochloride, pH=7.2. To this solution was added CRANK-NH$_2$ peptide dissolved into 100 µl of the same phosphate buffer and 3 ul of thiophenol. The reaction was monitored by analytical reversed-phase HPLC. After 24 hours, the ligated product, LY-(SAOD)-AGCRANK-NH$_2$ (SEQ ID NO: 10), was isolated by semi-preparative reversed-phase HPLC (gradient=10-50% B over 60 minutes) and lyophilized to yield a fluffy white solid. Amino acid analysis was consistent with the desired product peptide. Expected Mass=1168, Observed Mass=1168.

Ligation of LY-(SAOD)-AGMPAL-Thioester with CEYRIDRVRLFVDKLDNIAQ-VPRVGAA-HHHHHH (SEQ ID NO: 7). LY-(SAOD)-AG-MPAL (0.3 mgs, 0.37 mmol) and CEYRIDR-VRLPFVDKLDNIAQ-VPRVGAA-HHHHHH (1.5 mgs, 3.8 mmol) were subjected to the same ligation and purification conditions as described above to yield 1.0 mgs (58% yield) of a white fluffy solid. Expected Mass=4518, Observed Mass=4517.

Synthesis of Amino-Terminal P21 Binding Domain (PBD) Peptide Fragment, (SAOD)-KKKEKERPEISLPSDFEHTI-HVGFDA-MPAL Thioester (SEQ ID NO: 8): Secondary aminooxy containing amino-terminal PBD thioester were synthesized as described above using TAMPAL resin. HF cleavage utilizing p-Cresol scavenger followed by HPLC purification yielded (SAOD)-KKKEKERPEISLPSDFEHTI-HVGFDA-MPAL containing two DNP groups protecting the histidines. Mass Expected=3745, Mass Observed=3745.

Synthesis of Carboxy-Terminal of P21 Binding Domain (PBD) Peptide Fragment, CTGEFTGMPEQWARLLQT (SEQ ID NO: 9): The native carboxy-terminal half of PBD was synthesized using standard FMOC synthesis protocols by the Scripps Peptide and Protein Core Facility. Mass Expected=2068, Mass Observed=2068.

Synthesis of SAOD-Modified PBD, SAOD-KKKEKER-PEISLPSDFEHTIH-VGFDACTGEFTGMPEQWARLLQT (SEQ ID NO: 11): 1.5 mg of SAOD-KKKEKERPEISLPSD-FEHTIHVGFDAMPAL (0.4 mmol) was ligated to 1 mg (4.8 mmol) of carboxy-terminal fragment, CTGEFTG-MPEQWARLLQT, as described above. After 48 hours, the ligated PBD proteins were isolated by RP-HPLC and lyophilized, 1.5 mg (70% yield), Mass Expected=5262, Mass Observed=5262.

Selective Labeling of SA-Test Peptide with Tetramethylrhodamine N-hydroxysuccinimidyl ester. A solution of SA-test peptide (3.396 µg/µl, 2.18 mM) in 5% acetate buffer, pH=4.7 incorporating 5 mM TCEP was utilized for labeling. A stock solution of dye (5 µg/µl, 9.5 mM) was made by dissolving TMR-OSu in neat DMSO. For each reaction, the dye stock was diluted so that the desired number of dye equivalents could be added in 20 µl of DMSO. The following equivalents of dye were tested: 1.2, 1.5, 1.8, 2.0, 2.4, 3.0, and 4.3. With constant stirring, 20 µl of dye solution was added in two 10 µl aliquots to 20 µl of peptide solution at room temperature. The second aliquot of dye in DMSO was added 10 minutes after the initial dye addition. After complete addition of dye, the reaction was briefly vortexed, then incubated at room temperature. After 3 hours, the labeled reaction product(s) were separated from unreacted dye by gel filtration on Sephadex G-10 or G-15 columns using either 100 μM ammonium bicarbonate or, after optimization, 0.1% TFA in water. The individual peptide product(s) were then separated by RP-HPLC and analyzed by ESI-MS. Mass Expected=1971, Mass Observed 1970.

Non-Selective Labeling of SA-Test Peptide with Tetramethylrhodamine N-hydroxysuccinimide ester. SA-test peptide (3.396 μg/μl, 2.18 mM) was dissolved 100 mM sodium carbonate, pH=9.01 containing 5 mM TCEP. 18 μl of neat DMSO was added to 20 μl of peptide solution. With rapid mixing, 1 μl stock dye solution in DMSO was added to this mixture. Upon completion of addition, the reaction was vortexed briefly, then incubated at room temperature. After 3 hours, a 1 μl aliquot was removed and evaluated by RP-HPLC and ESI-MS. This process was repeated until significant levels of reaction were detected by formation of single-labeled SA-lysine test peptide products.

Selective Labeling of LY-(SAOD)-AGCRANK-NH$_2$ and LY-(SAOD)-AGCEYRIDRVR-LFVDKLDNIAQVPRV-GAA-HHHHHH with Tetramethylrhodamine N-hydroxysuccinimidyl Ester. A sample of 20 μL of LY-(SAOD)-AGCRANK-NH$_2$ (2.5 μg/μl, 2.18 mM) in 200 mM citrate buffer, pH=4.7, 5 mM TCEP was labeled using 4.3 equivalents of dye in DMSO, purified and analyzed. Expected Mass=1580, Observed Mass=1580. A 20 μL sample of LY-(SAOD)-AGCEYRIDRVRLFVDKLDNIAQVPRVGAA-HHHHHH (SEQ ID NO: 12) (9.7 μg/μl, 2.12 mM) in 200 mM citrate buffer, pH=4.7, containing 5 mM TCEP and 3M guanidine hydrochloride was labeled using a modified procedure. 18 μl of a solution of tetramethylrhodamine N-hydroxysuccinimide (10 μg/μl) in DMSO was added in 6 μl aliquots over 15 minutes with rapid mixing. The reaction was incubated at room temperature for 5 hours prior to gel filtration/RP-HPLC purification and mass spectral analysis. Expected Mass=4930, Observed Mass=4929.

Labeling of β-Lactoglobulin with Tetramethylrhodamine N-hydroxysuccinimide ester: 10 μL of a 10 mg/ml solution of tetramethylrhodamine N-hydroxysuccinimide ester in DMSO (9.5 equivalents compared to protein), was added to a solution containing 10 μL of DMSO and 20 μL of a solution of β-Lactoglobulin (20.3 mg/ml or 1.1 mM) in 2.8 M guanidine hydrochloride with 5 mM TCEP (pH 4.7). After 3 hours, protein was separated from unreacted dye by gel filtration, and labeling was determined by analysis of the dye-to-protein ratio (protein concentration was determined by the method of Waddel and ε for tetramethylrhodamine in phosphate buffer, pH=8.0 of 81,000).

Labeling of PBD Proteins with Alexa-532 N-Hydroxysuccinimide Ester: 150 μg of the SAOD-modified PBD protein was dissolved in 105 □L of 200 mM sodium citrate buffer, pH=4.8, containing 5 mM TCEP (protein concentration ~0.28 mM). A solution of Alexa-532-OSu in DMSO (dye concentration ~10 mg/ml in DMSO) was titrated into the protein solution in 5 μL aliquots over 72 hours. Four hours after each addition, the extent of labeling was determined by RP-HPLC and MS. Labeling was continued until quantities of double-labeled PBD was obtained (SAOD-modified PBD). Alexa-532 labeled SAOD-modified PBD, Mass Expected=5871, Mass Observed=5870.

Zinc/Acetic Acid Reduction of the N-methylaminooxy N—O Bond in Peptides. Reductive cleavage of the N—O bond was performed using zinc and aqueous acetic acid. Effervescence in the reaction was evident after a few seconds and subsided after 60-120 minutes. After 14 hours, the reaction supernatant was analyzed by RP-HPLC and ESI-MS. Reduction of labeled SA-Test peptide, Expected Mass=1530, Observed Mass=1530: Reduction of labeled (SAOD)-AGCRANK-NH$_2$: Expected Mass=1139, Observed Mass=1139.

Trypsin/Chymotrypsin Cleavage of Labeled LY-(SAOD)-AGCEYRIDRVRLFVDKLDNIAQVPRVGAAHHHHHH Peptide. 10 μl of a 0.05 mg/ml solution of either trypsin or α-chymotrypsin in 25 mM ammonium carbonate (without pH adjustment) was added to 5 μl of a 10-20 μg/μl solution of pure tetramethylrhodamine-labeled peptide in water (final concentration of protease is 0.033 mg/ml). The reaction was incubated at room temperature for 24 hours prior to analysis of peptide fragments by MALDI-MS.

EXAMPLE 5

Synthesis and Characterization of Fluorescent Dyes

Materials and Methods. Commercially available solvents and reagents were purchased from major suppliers. $^1$H NMR spectra of dye solutions in DMSO-d$_6$ were recorded at 500.11 Hz on Bruker Avance DRX-500 MHz. The pentet corresponding to the residual protons of DMSO-d$_6$ (2.49 ppm) was used as internal reference.

The analytical sample of the dyes was purified by HPLC on a Vydac C-18 column (no. 218TP152022, 22*250 mm, 15-20 μm, 3 mL/min) using acetonitrile-water gradient elution.

Absorbance spectra were recorded on Hewlett-Packard HP8452 diode array spectrophotometer and fluorescence spectra were recorded on SPEX Fluorolog 2 spectrometer.

All reactions were run in a oven-dried round bottom flask, under argon atmosphere, and capped with a rubber septum. 1-Benzothiophen-3(2H)-one 1,1-dioxide was synthesized according the procedure of M. Regitz (Chem. Ber., 1965, 98: 36). 3-(dicyanomethylene)indan-1-one was synthesized from 1,3-indandione by the method of K. A. Bello, L. Cheng and J. Griffiths (Chem. Soc. Perkin Trans. II, 1987, 815-818).

Preparation of 2Z)-2-[(2E)-3-METHOXYPROP-2-ENYLIDENE]-1-BENZOTHIPHEN-3(2H)-ONE 1,1-DIOXIDE (Compound 1-SO), (2Z)-2-[(2E)-3-METHOXYPROP-2-ENYLIDENE]-3-(DICYANOMETHYLENE)INDAN-1-ONE (Compound 1-CN)

To a solution of corresponding ketone (2.5 mmol) in 20-50 ml of methanol was added trifluoroacetic acid in one aliquot at 80° C. followed immediately by the addition of 2 ml of 1,3,3-trimethoxy propene. The reaction mixture turned into a clear dark brown solution and after an interval of 30 sec a yellow solid precipitated out. The precipitate was filtered and dried.

For compound 1-SO, the yield was 60%. 1H NMR (CDCl$_3$): δ 4.04 (s, 3H, CH$_3$O), 6.53 (t, $^3J_{H-H}$=12.1 Hz, 1H), 7.53 (d, $^3J_{H-H}$=11.7 Hz, 1H), 7.74 (d, $^3J_{H-H}$=12.8 Hz, 1H), 8.2-8.4 (m, 4H, Ph).

For compound 1-CN, the yield was 60%. $^1$H NMR (CDCl$_3$): δ 8.67 (dd, 6.2 Hz, 2.9 Hz, 1H), 8.37 (d, 11.7 Hz, 1H), 7.87 (m, 1H), 7.73 (m, 3H), 7.51 (d, 12.05 Hz, 1H), 3.98 (s, 3H).

PREPARATION OF (2Z)-2-[(2E,4E)-4-(3-(3-SULFONATOPROPYL)-1,3-BENZOTHIAZOL-2(3H)-YLIDENE)BUT-2-ENYLIDENE]-1-BENZOTHIOPHEN-3(2H)-ONE 1,1-DIOXIDE (DYE 2)

1.16 g (2.00 mmol) of 3-(2-methyl-1,3-benzothiazol-3-ium-3-yl)propane-1-sulfonate and 625 mg (2.50 mmol) of compound 1-SO were dissolved in 65 ml of mixture $CH_3OH$—$CHCl_3$ (1:1) and heated at reflux. 328 mg (4.00 mmol) of AcONa in 10 ml was added at once and the reaction mixture was refluxed for additional 30 min. After cooling, the dye was separated by filtration, recrystallized from methanol and dried. The yield was 65%.

$^1$H NMR: (DMSO-$d_6$) δ 1.85 (p, $^3J_{H-H}$=6.2 Hz, 2H, $CH_2$—$CH_2$—$CH_2$), 2.60 (t, $^3J_{H-H}$=6.2 Hz, 2H, $CH_2$—$CH_2$—$SO_3$), 4.45(t, $^3J_{H-H}$=6.2 Hz, 1H, $CH_2$—N), 6.87 (d, $^3J_{H-H}$=13.2 Hz, 1H), 7.3-8.1 (m, 11H).

TABLE 2

Selected Merocyanine Dyes.

| Compound | Dye Structure |
|---|---|
| 1 | [structure] |
| 2 | [structure] |
| 3 | [structure] |
| 4 | [structure] |

TABLE 3

Spectral Data for Selected Merocyanine Dyes.[1]

| Compound | Extinction coefficient (*10$^{-3}$) | Absorption Maximum | Emission Maximum | Quantum Yield |
|---|---|---|---|---|
| 1 | 100 | 618 | 636 | 0.07 |
| 2 | 100 | 603 | 623 | 0.10 |
| 3 | 120 | 586 | 618 | 0.17 |
| 4 | 80 | 667 | 693 | 0.10 |

[1]All spectral data are recorded in n-butanol.

EXAMPLE 6

Imaging the Spatio-Temporal Dynamics of Rac Activation in vivo with FLAIR

FLAIR (Fluorescent Activation Indicator for Rho GTPases) is a biosensor system that maps the spatial and temporal dynamics of Rac activation in living cells. The approach is based on microinjection of a fluorescently labeled domain from p21-activated kinase into cells expressing GFP-Rac. The injected domain (called PBD, for p21-binding domain) binds only to Rac-GTP, and not to Rac-GDP (Thompson et al., 37 Biochemistry 7885 (1998); Benard et al., 274 J. Biol. Chem. 13198 (1999)). Within living cells, PBD binds to the GTP-Rac wherever it has bound GTP, bringing the Alexa546 dye on the PBD near the GFP on the Rac to produce fluorescence resonance energy transfer (FRET). Thus, the FRET signal marks subcellular locations where Rac is activated. This can be quantified to follow the changing levels and locations of Rac activation or to trace the kinetics of total Rac activation on an individual cell basis.

The labeling of PBD with Alexa, and mammalian expression vectors for expression of Rac-GFP is by any procedure, for example, as described in this application. This example provides protocols for production of pure PBD, protocols for generating cell images suitable for quantitative analysis of rac activation, and procedures and caveats for generating two types of data: images showing the spatial distribution of Rac activation within cells, and curves showing the kinetics of Rac activation in single cells.

PBD Expression and Purification. PBD was expressed in the form of C-terminal 6His fusion from the prokaryotic expression vector pET23 (Novagen). It was determined experimentally that the highest levels of expression are observed when a vector containing plain T7 promoter (not T7lac) is used in combination with a BL21(DE3) strain (not the more stringent BL21(DE3)pLysS) of *E. coli*. This system allows for "leaky" protein expression (Novagen). While the 6His tag can be cleaved from the purified protein with thrombin, it is not necessary, as the tag does not have any significant effect on probe functionality.

Competent BL21 (DE3) cells (Stratagene) are transformed with pET23-PBD using standard procedures. See, e.g., Sambrook et al., Molecular Cloning: A Laboratory Manual (Cold Spring Harbor Laboratory Press 1989) After transformation, cells were plated on an LB plate containing carbenicillin. Cells do not degrade carbenicillin as quickly as ampicillin, so a higher percentage of cells retain the vector at the culture density appropriate for induction (Novagen). Five ml of LB media with 100 µg/ml carbenicillin were inoculated with a single colony of cells, and grown in the shaker at 37° C. for 6-8 hours (until dense). Two ml of this are then used to inoculate 50 ml of LBcarb. The rest of the culture is diluted 1:1 with glycerol and frozen for long term storage at −80° C. The 50 ml culture is incubated in the shaker overnight at 37° C. Next morning 1-2 L of LBcarb are inoculated with the overnight culture (15-20 mL culture/500 mL media), and grown in the shaker (37° C.) to $OD_{600}$=0.8-0.9 (about 2-3 hours). After that the cultures are briefly chilled on ice to 30-32° C., then put back in the shaking incubator turned down to 30-32° C. The protein is expressed at a lowered temperature to increase the portion of the correctly folded, soluble PBD. IPTG is added to a final concentration of 0.4-0.5 mM, and the cultures are allowed to grow for another 4-5 hours at 30-32° C. (shaker). The cells are collected by centrifugation (8,000 G, 4 min), and stored as a pellet at −20° C. until use. Approximately 2.5-3 g of cells is usually obtained from each liter of culture.

Purification of PBD-6His is performed essentially as described in the Talon affinity resin manual (Clontech). The cells (3-5 g) are thawed in 20-30 ml of the Lysis buffer (30 mM Tris HCl, pH 7.8, 250 mM NaCl, 10% glycerol, 5 mM $MgCl_2$, 2 mM β-ME, 1 mM PMSF), homogenized with a spatula and sonicated (4 pulses, 10-15 sec each). T4 lysozyme and DNAse are added in catalytic amounts (approximately 100 micrograms/ml lysozyme and 500 U DNAse) to help the lysis, and the suspension is incubated on ice with periodic mixing for 30 min. The cells are then centrifuged at 12,500 rpm for 30 min, and the supernatant containing PBD is carefully transferred into a 50 mL Falcon tube.

Talon resin (1.5-2 ml) (Clontech) is washed twice with 10 volumes of the lysis buffer in a 15 ml Falcon tube, centrifuging in the swinging bucket centrifuge at low speed in between to separate the resin. The cell lysate is added to the 1.5 ml of washed Talon resin in a 50 mL falcon tube, and inverted or agitated gently (i.e. with an orbit shaker) for 20-30 mm at r.t. The resin is then separated by centrifugation in a swinging bucket centrifuge. The supernatant containing the unbound fraction is removed and saved for SDS-PAGE analysis. The resin is then transferred into a new 15 mL Falcon tube and washed twice (10-15 min each, r.t., orbit shaker) with 12 mL of the lysis buffer, without PMSF and βME. The third wash is performed with lysis buffer+10 mM imidazole (add 1 M stock in water, kept at −20° C.). After the final separation, the resin is resuspended in 2-3 mL of lysis buffer with 10 mM imidazole, and pipetted into a column (0.5 cm in diameter). The resin is allowed to sediment by gravity flow until the fluid above the resin bed is almost gone, and then another 3-5 mL of Lysis buffer with 10 mM imidazole is added to wash the column. The elution is performed using Lysis buffer with 60 mM imidazole, and ca. 500 µL fractions are collected. PBD usually elutes in fractions 5-13 (total volume about 3-4 mL). An aliquot of each fraction is run on a 12% SDS-PAGE and the fractions containing the pure PBD are combined and dialyzed against 1 L of 25 mM NaP buffer (pH 7.3). A dialysis bag (SpectraPor 7), or dialysis cassette (Pierce) with a molecular weight cutoff value of 3,500 kDa can be used.

After 2-3 hours of dialysis, the bag is wiped with a Kim-Wipe and buried in Aquacide powder (Caibiochem) for 15-45 min at 4° C., depending on the volume of the sample in the bag. This concentration process should be monitored carefully as complete drying may occur if the bag is left in the Aquacide for too long. The powder is scraped gently from the bag every 10-15 min to facilitate water absorption. When the sample reaches 0.5-1.5 mL in volume (3-10-fold concentration), the Aquacide is cleaned from the bag, and the sample is carefully removed. The sample is briefly centrifuged (14,000 rpm, 2 min) to separate it from the precipitated material, and transferred into a new dialysis bag or cassette. After the second dialysis step, the concentration of PBD is measured by taking a small aliquot (5-10 µL) and diluting into 50 mM TrisHCl (pH 7.5-8.0) or other appropriate buffer. The extinction coefficient of PBD at 280 nm is 8,250 (estimated from the primary sequence). On average, 1.5-2 mg of PBD is obtained per liter of cell culture.

Other methods of concentrating PBD were found to be less effective. For instance, centrifugal concentrators require prolonged centrifugations, and result in nonspecific adsorption of the small PBD protein to the membrane. It is essential to perform dialysis after concentration with Aquacide. This prevents the ionic strength of the resultant protein prep from becoming too high before labeling. Low ionic strength conditions are preferable to avoid excessive precipitation of the protein during attachment of the hydrophobic dye.

Loading GFP-Rac and Alexa-PBD in cells. Cells were first transfected with GFP-Rac through nuclear microinjection. The EGFP variant (Clontech) was used that produced significantly brighter cells than wild type GFP (Heim et al., 6 Current Biology 178 (1996)). For microinjection of DNA and of PBD-Alexa, glass pipettes with 1.0 mm outer diameter and 0.50 mm inner diameter (Sutter) were pulled using a micropipette puller (Sutter Model P-87) to make microinjection needles with tips of approximately 0.5 µm diameter. Rac-GEP c-DNA is injected into Swiss 3T3 fibroblasts at 200 ng/µL, using a constant needle pressure of approximately 100 hPa. DNA can be centrifuged prior to injection (20,000 G for 15 minutes) to prevent clogging the needle.

Cells expressing GFP-Rac were microinjected with Alexa-PBD using a microscope with optics and illumination capable of revealing the GFP fluorescence (detection sensitivity is typically improved by using higher NA objectives and brighter light sources, such as a 100 W Hg arc lamp). Thus, only GFP-expressing cells need to be injected. To reduce background fluorescence during injection and the following experiment, cells are placed in 1 mL of pre-warmed Dulbecco's Phosphate Buffer Solution (DPBS) containing 1000 mg/L D-glucose, 36 mg/L sodium pyruvate and supplemented with 0.2% BSA, 1% L-glutamine and 1% Penicillin-Streptomycin. During injection and the following experiment, cells are mounted in a Dvorak live cell chamber (Nicholson) preheated to 37° C., and maintained at 37° C. by a heated stage (20/20 Technology). The microscope can be equipped with a motorized stage and shutter controls (Ludi) to monitor multiple stage positions in one experiment.

Cells that are barely expressing or expressing too much GFP-Rac were ignored. The former produce FRET too weak for recording, and in the latter overexpressed Rac affects the biology of the cell. In general, we observed that cells expressing less than 300 intensity units (IU) do not display Rac-induced ruffling and altered morphology. The precise value of this cutoff will depend on the sensitivity of the imaging system, and should be determined by each lab for a relevant biological behavior.

A 100 μM solution of Alexa-PBD was centrifuged at 20,000 G for 1 hour prior to injection, and then injected into the cytoplasm of cells expressing the GEP-Rac. Lowering the needle into the region just adjacent to the nucleus seems to produce the best combination of efficient injection and cell health. After the injection, cells are placed back into the 37° C. incubator for 5-10 minutes to recover. Alexa-PBD could potentially act as an inhibitor of Rac activity, so controls were carried out showing that, for our imaging system, up to 1000 IU of Alexa-PBD do not inhibit induction of ruffling.

Imaging Rac activation. Imaging experiments were performed using a Photometrics KAF 1400 cooled CCD camera, and Inovision ISEE software for image processing and microscope automation. Although filters are undergoing further optimization, the best success to date has been achieved with the following filters, designed with sharp cutoffs specifically for this purpose by the Chroma corporation: GFP: HQ480/40, HQ 535/50, Q505LP FRET: D480/30, HQ610/75, 505DCLP Alexa: HQ545/30, HQ610/75, Q565LP.

The exact camera settings depend on the type of experiment being performed. When the total Rac activity within the cell is being determined, images are not generated, so spatial resolution can be sacrificed for increased sensitivity. Images are taken using 3×3 binning with exposure times of 0.1 sec, 0.1 sec, and 0.5 sec for GFP, Alexa and FRET respectively. When images are required, i.e. to examine the changing spatial distribution of Rac activation, 1×1 binning is used with exposure times of 1 sec, 1 sec and up to 5 sec for GFP, Alexa and FRET respectively. These settings depend on the sensitivity of the imaging system used, and the desired trade off between sensitivity and spatial or temporal resolution. Settings should always be chosen not exceed the dynamic range of the camera (Berland et al., in Sluder et al. (eds.), Video Microscopy at 33 (Academic Press 1998). Motion artifacts should also be considered during imaging experiments. For fast moving phenomena, features of the cell may move appreciably during the time between acquisition of the FRET and GFP images. This results in artifacts when the image is corrected for bleedthrough, as described in more detail below. Such artifacts can be prevented by reducing the time between exposures, or by using two cameras simultaneously.

When total Rac activation is being determined, a picture of GFP-Rac and FRET is taken at each time point. Only one image of Alexa-PBD, usually at the initial time point, will also be required (for bleedthrough corrections as described below). In contrast, when generating images (i.e. to determine the distribution of rac activation) an Alexa-PBD image is taken at each time point. The reasons for this are discussed in the 'Image Processing' section below. If the cells are to be treated with some type of stimulus, it is helpful to take a series of images prior to stimulation as controls for noise, bleaching, and other artifacts.

Image Processing. Image analysis is performed to follow the kinetics of total Rac activity within individual cells, displayed as curves of activation over time, or to generate images that show the subcellular location of rac activation. The proper application of corrections is needed essential for quantitative imaging. Common image processing operations can be used for this purpose (Berland et al., in Sluder et al., Video Microscopy at 33 (Academic Press 1998). Procedures for such image processing operations will depend on the software package used. The correction factors should be rigorously applied when using the FLAIR system, as FRET signals will be low relative to other sources of fluorescence in the sample. The FRET signal must purposefully be kept low, as minimum quantities of fluorescent molecules should be used to prevent perturbation of cell behavior. Hence, FLAIR procedures must be more carefully controlled than procedures generally used with fluorescent probes.

The following protocols assume use of a cooled CCD camera, which typically show low levels of noise, linear response to light intensity, and little variation in response from pixel to pixel. It is valuable to use cameras and software with the greatest possible bit depth (allotment of computer memory to each pixel to maximize the number of possible intensity gradations). This is especially important for ratio operations, which are typically performed using 12 bit images or greater. Operations are described in the order in which they should be performed:

1. Registration. For corrections applied in later steps, it is important that each of the images taken using different excitation and emission wavelengths be registered so that the cells lie atop one another, with cell edges and internal features exactly coinciding. Different image processing software will accomplish this in different ways, but manual translocation is usually involved so that one image lines up with a second, fixed image. This is best accomplished by zooming in on cells and adjusting brightness and contrast to clearly see cell edges and internal features. Since the GFP-Rac signal is generally the strongest, it was used as the reference image in these experiments. When the bleedthrough corrections described below are performed, errors in registration often become apparent as 'shadow effects.'

2. Background subtraction. There are two methods commonly used for background subtraction. If the only intention is to follow the changing spatial distribution of the FRET signal over time, and if the background (in the absence of cells) remains uniform across the field of view throughout the experiment, then it is sufficient to determine the background intensity in several regions of the image outside the cell. The average value of these intensities is then subtracted from each pixel in the image. This method can also be sufficient for following qualitative changes in the subcellular location of activation, but it must be used with caution. Subtle variations in background intensity across the cell could be large relative to the changes observed in FRET, producing artifacts. When quantifying the kinetics of total cell Rac activity over time (see following sections), it is better to take an image of a region of the coverslip containing no cells or fluorescent debris, under the same conditions used for taking the real image. This background image is then subtracted from the real image prior to further analysis. A separate background image must be taken for each type of image (GFP, FRET or Alexa) and at each time point when successive images are obtained 3. Masking. It is advisable to mask out regions surrounding the cells prior to further analysis. The edges of the cell are outlined, in most software either manually or by eliminating all sections of the images below a certain intensity value (interactive thresholding). The regions outside the cell are thus identified and eliminated from further calculations. The precise approach for accomplishing this will depend upon the software employed. However, the mask is usually a binary image with all values within the cell=1, and all outside=0, and the real image is multiplied by the mask. The mask is best generated using the GEP image, which has the strongest signal and therefore the most clearly defined edges. When determining the total intensity within the cell, analysis should be carried out on the same pixels within the FRET, GFP, and Alexa images. Therefore, the same mask is applied to each image after registration, assuring that exactly the same pixels are analyzed.

4. Bleedthrough correction. During FRET it is necessary to excite the donor fluorophore while monitoring emission from the acceptor fluorophore. It is extremely difficult to design FRET filters that see only FRET emission and block all GFP emission, or block all light from Alexa excited directly rather than by FRET. To correct for "bleedthrough" of such light into the FRET image, the fluorescence filters must be characterized by taking images of cells containing GFP-Rac or AlexaPBD alone. For example, in bleedthrough correction for GFP, cells are imaged using both the GFP and FRET filter set. When observing the GFP fluorescence through FRET filters, a fixed percentage of the GFP emission will be seen. The total fluorescence intensity is determined for both the GFP and FRET images from cells containing only GFP-Rac. A GFP bleedthrough factor is computed for each cell by dividing the intensity through the FRET filters by that through the GFP filters (the 'bleedthrough factor' for GFP: FRET intensity/GFP intensity). This value is plotted against cell intensity for numerous cells, and a line is fit to this data to produce an accurate value of the bleedthrough factor. It is important to use background-subtracted images. The process is repeated for Alexa-PBD. When the actual experiment is performed, an Alexa-PBD, GFP-Rac, and FRET image are obtained. After background subtraction of all three images, the Alexa-PBD and GFP-Rac images are multiplied by the appropriate bleedthrough factor and subtracted from the FRET image. This is an extremely important step that must be applied carefully to prevent artifacts that appear to be regions of high FRET, especially as the magnitude of the FRET signal approaches that of the bleedthrough. It is important not to use GFP-Rac or Alexa-PBD images that exceed the dynamic range of the camera ('overexposure') as they will not fully eliminate bleedthrough. Motion artifacts can also produce errors derived from bleedthrough corrections.

Production of total activation curves (bleaching correction). To determine how overall Rac activity within a cell changes over time, the total fluorescence intensity within a GFP-Rac and FRET image is determined at each time point. The intensity of the FRET image is divided by that of the GFP-Rac image. This ratio better reflects total Rac activity than does FRET intensity alone. Division by GFP-Rac normalizes out errors due to bleaching of GFP, effects of uneven illumination, and other factors affecting both the GFP and FRET signals. Because all FRET occurs through irradiation of GFP, bleaching of GFP will decrease both GFP and FRET emissions to the same extent. Therefore, the FRET/GFP ratio will be a measure of Rac activity that is not affected by bleaching. It is critical that each image be properly background subtracted and corrected for bleedthrough. Bleedthrough corrections are somewhat simplified when generating these curves, as they need not be carried out on actual images, but simply on the total intensity values derived from the images. The total intensity of the GFP-Rac image is multiplied by the GFP bleedthrough factor, and the resulting value is subtracted from the FRET intensity. An analogous operation is performed for Alexa-PBD bleedthrough. One need only obtain a single Alexa-PBD image (usually at the beginning of the time series) and use this for bleedthrough correction of all images in the time series. If Alexa-PBD is not irradiated during the experiment, its bleaching will be negligible and this single image will reflect the actual Alexa-PBD level throughout the entire time series.

Any ratio calculations are best performed using floating point operations. Large errors can be generated by software that truncates noninteger values into integers to display data as images. Such problems can be overcome by multiplying the images by a large scalar value prior to division. This value should be as high as possible without causing any pixel to exceed the bit depth of the image file. For example, a 12-bit image file can only hold values up to 4095 ($2^{12}$), so the constant selected must not cause the highest intensity value in the image to exceed 4095. When operations are performed on whole cell values rather than on images, as with production of the Rac activation curves described here, it is convenient to determine total cell intensities and then perform any division operations in a floating point spreadsheet program, such as Microsoft Excel.

Examining changes in the localization of Rac activation. The sections above describe how to generate images showing the distribution of FRET within cells. A sequence of such images can be compared to show how localizations vary with time. While simple examination can suffice to show distribution changes, the overall intensity of FRET, and hence the perceived activation level, could become successively lower over time due to bleaching of the GFP. We have found that bleaching is not a serious issue for at least 20 images under the exposure conditions described here. The total GFP intensity at the beginning and end of the experiment should be examined to gauge bleaching effects. One can correct for bleaching by dividing each pixel in the image by the total intensity of GFP determined at the same time point.

Many aspects of cytoskeletal control and signaling crosstalk depend upon the localization of Rho family GTPase activation, and may depend as well on the level and duration of activation. Signaling control by the precise dynamics of GTPase activation has been suggested by indirect experiments, but has been very difficult to quantify or study using previous methods. The FLAIR system reported here can reveal Rac activation dynamics in vivo and can accurately report the changing activation levels within a cell.

EXAMPLE 7

Cellular Localization of Rac GTPase Activation Using p21 Activated Kinase (PAK) as a Protein Biosensor Prevailing evidence suggests that signaling proteins must be tightly regulated both spatially and temporally in order to generate specific and localized downstream effects. For Rac1 and other small GTPases, binding to GTP is a critical regulatory event that leads to interaction with downstream targets and regulates subcellular localization. Here we use FLAIR (fluorescence activation indicator for Rho proteins), to quantify the spatio-temporal dynamics of Rac1 GTP interaction in living cells. FLAIR reveals precise spatial control of growth factor-induced Rac activation in membrane ruffles, and in a gradient of activation at the leading edge of motile cells.

Rac is a member of the Ras superfamily of small GTPase proteins (A. Hall, Science 279, 509-14 (1998)). It plays a critical role in diverse signaling pathways, including control of cell morphology, actin dynamics, transcriptional activation, apoptosis signaling, and other more specialized functions (L. Kjoller, A. Hall, Exp. Cell Res. 253 166-79 (1999)). The broad range of events controlled by this GTPase requires subtle regulation of interactions with multiple downstream targets. Accumulating evidence suggests that the effects of Rac are in part controlled by regulating the subcellular localization of its activation through GTP binding. For example, Rac is known to induce localized actin rearrangements to generate polarized morphological changes (C. D. Nobes, A.

Hall, J. Cell Biol. 144(6), 1235-1244 (1999). GTP exchange factors (GEFs) which regulate nucleotide exchange on Rho GTPases contain a variety of localization domains and may modulate downstream signaling from Rac (Zhou et al, J. Biol. Chem. 273(27), 16782-16786 (1998).

Although control of Rac1 signaling through localized activation is clearly important, it is difficult to study in an intact cell. Here we develop and apply a new method based on fluorescence resonance energy transfer (FRET) which can quantify the timing and location of Rac activation through GTP binding. This method is applied to examine the hypothesis that specific and localized Rac1 activation occurs during the course of extracellular signal-induced cytoskeletal dynamics.

Figure 5:
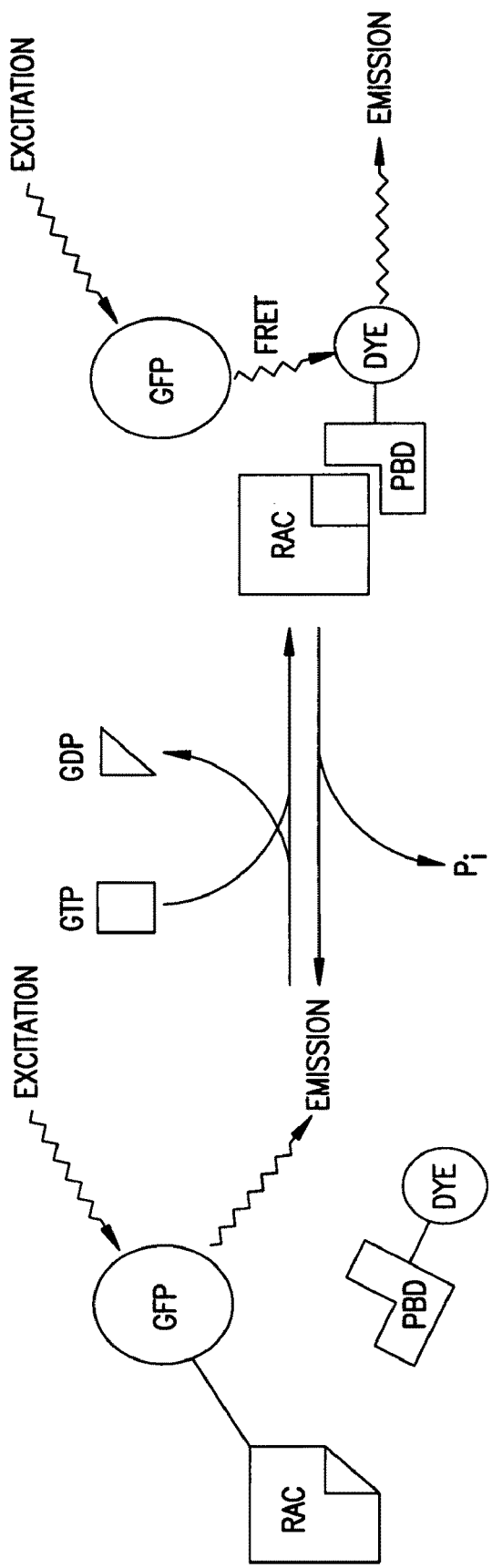
FIG. 5 illustrates one method for using biosensors according to the present invention. In this example, the activation of Rac1 ("RAC") by GTP was observed. A fragment of p21-Activated kinase (PAK) capable of binding to Rac1 (termed "PBD") was used as a biosensor because PAK will only bind to Rac1 when Rac1 is activated by GTP. A Rac1-Green Fluorescent Protein fusion protein (shown as a square named "RAC" attached to a circle named "GFP") was made and a cell line expressing this fusion protein was generated. Cells expressing RAC-GFP were injected with PBD labeled with Alexa-546 dye ("Dye"). The PBD biosensor binds selectively to GTP-RAC-GFP, but not to GDP-RAC-GFP. Upon binding to GTP-RAC-GFP, the Alexa on the labeled fragment undergoes fluorescence resonance energy transfer (FRET) as the Alexa and GFP fluorophores are brought close together. This FRET can be measured within a living cell or in vitro to map the distribution, localization and level of Rac-GTP activation. FRET produces a fluorescence signal which is distinct from a GFP fluorescence signal because energy is transferred from the excited GFP fluorophore to the nearby Alexa dye (J. R. Lakowicz, *Principles of Fluorescence Spectroscopy* (Plenum Press, New York, 1983), pp. 305-341)). By imaging the cell with different wavelengths, both the distribution of Rac and Rac activation can be studied in the same cell. GFP excitation and emission are used for overall Rac distribution, while GFP excitation and Alexa emission are used for FRET.

The design of the Rac nucleotide state biosensor is shown schematically in FIG. 5. A fluorescently labeled protein biosensor is introduced into the cell together with a biologically active GFP-fused Rac (C. Subauste et al, J. Biol. Chem. 275(13), 9725-9733 (2000). This protein biosensor is labeled with an acceptor dye capable of undergoing FRET with GFP. Since the biosensor is derived from a specific GTP-Rac target protein, it binds to GFP-Rac 1 only when the Rac1 is in its activated, GTP-bound form, and produces a localized FRET signal revealing the level and location of Rac activation. When cells expressing GFP-Rac were injected with the biosensor, we were able to simultaneously map the changing location of GFP-Rac1 and the subpopulation of GFP-Rac1 molecules in the activated, GTP-bound state. FRET is proportional to the amount of GTP binding, enabling quantitation of changing activation levels. It is also very specific, as only biosensor binding to the GFP-tagged protein will generate FRET. This approach has the potential to examine many protein states, including posttranslational modifications, conformation, and ligand binding.

The biosensor was made by fluorescently labeling a domain from p21 activated kinase I (PAK1) known to bind selectively to GTP-Rac. PBD (fragment of human PAK1, residues 65-150, with a single cysteine added in the penultimate N-terminal position) was expressed as a C-terminal 6His fusion protein from the pET23 vector (Novagen) and purified from E. coli strain BL21DE3 using Talon metal affinity resin (Clontech) as instructed by the manufacturer. All GFP constructs were prepared using the EGFP mutant (T. Joneson, Mol. Cell Biol. 19(9) 5892-901(1999); T. T. Yang et al., Gene 173, 19-23 (1996)), kindly provided by Dr. Roger Tsien of the University of California, San Diego. GFP-Rac 1 fusion and wild type Rac1 for in vitro studies were also expressed as 6His constructs and purified using a similar procedure. Purified protein was dialyzed against 50 mM sodium phosphate (pH 7.8), and labeled with 7 equivalents Alexa 546 maleimide (Molecular Probes) at 25 degrees for 2 hours. The conjugate was purified from unincorporated dye by G25 size exclusion chromatography followed by dialysis. The dye:protein ratio was between 0.8 and 1.3, as determined from absorbance of the conjugate at 558 nm (Alexa 546 extinction coefficient 104,000 $M^{-1}$ $cm^{-1}$) and 280 nm (PBD, extinction coefficient 8,250 $M^{-1}$ $cm^{-1}$ plus Alexa absorbance, determined as 12% of the absorbance at 546). Protein concentration was also independently determined using a Coomassie Plus protein assay (Pierce) and SDS-PAGE calibration with known concentrations of bovine serum albumin.

The p21 binding domain (PBD, aa 65-150) has been used successfully to precipitate GTP-Rac 1 from cell lysates (V. Benard, B. P. Bohl, G. M. Bokoch, J. Biol. Chem. 274, 13198-204(1999). In order to produce efficient FRET, the optimum site for attachment of an acceptor dye was determined by analyzing FRET between purified GFP-Rac1 and PBD labeled with various dyes in different positions. PBD contained no native cysteines, so the site of labeling could be controlled through introduction of a single cysteine, followed by labeling with cysteine-selective iodoacetamide dyes. After considerable optimization, the best candidate was found to be a PBD with cysteine appended to the N-terminus, labeled with commercially available Alexa 546 dye. The distance between the Alexa dye at the N-terminus of PBD and the fluorophore in GFP was calculated to be 52 A based on the efficiency of FRET and assuming random rotation of the fluorophores (Ro=51, n=¼, $k^2$=⅔) (T. Nomanbhoy et al., Biochemistry 35, 4620-4628 (1996). We coined the name FLAIR (fluorescent activation indicator for Rho proteins) for this new live cell imaging technique.

Figure 7A:
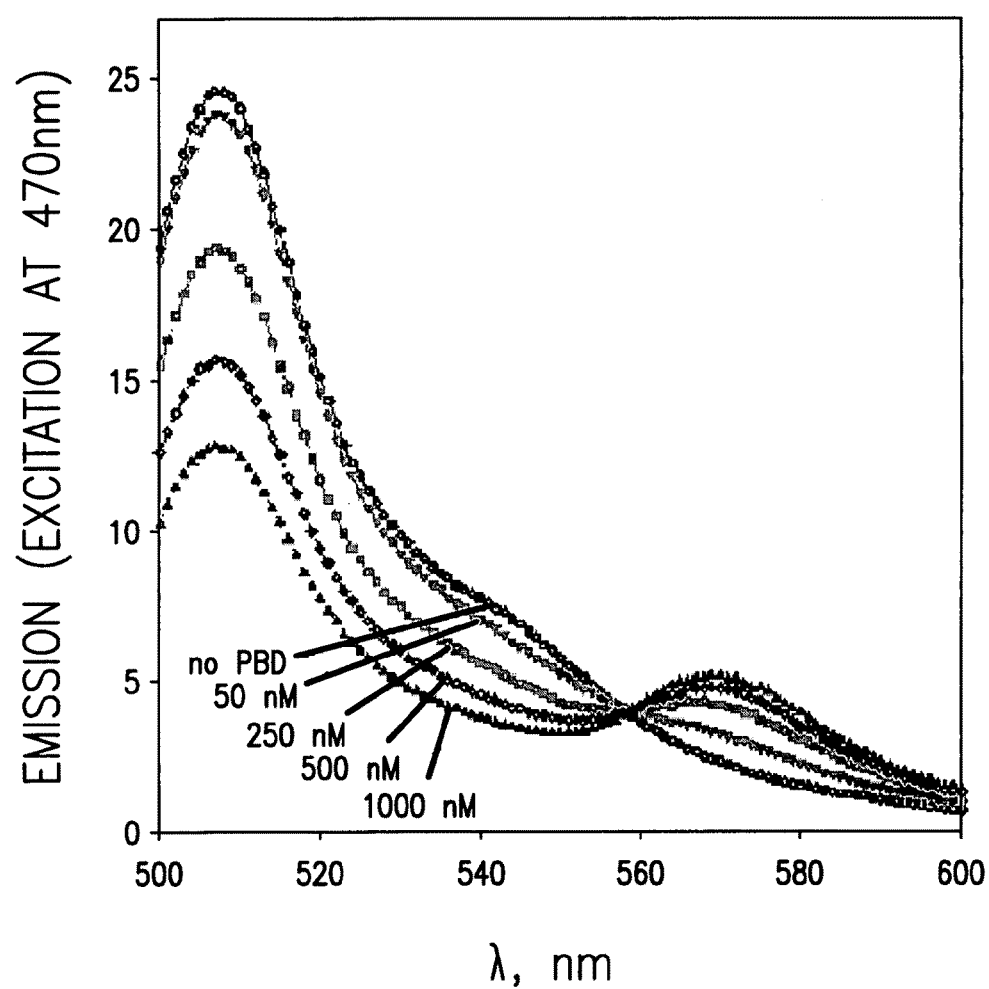
FIG. 7A shows fluorescence emission from solutions containing a fixed level of GFP-Rac bound to GTPγS at different concentrations of Alexa-PBD (PBD labeled with Alexa-546). Light at 480 nm was selectively used for GFP excitation, and direct (non-FRET) excitation of Alexa was subtracted from these spectra. In the absence of Alexa-PBD, the emission from GFP (peak at 508 nm) is maximal and no Alexa emission (peak at 568 nm) is seen. As the concentration of Alexa-PBD is increased, binding of Alexa-PBD to Rac-GFP leads to FRET, producing increasing emission at 568 nm and a decrease at 508 nm.
Figure 7B:
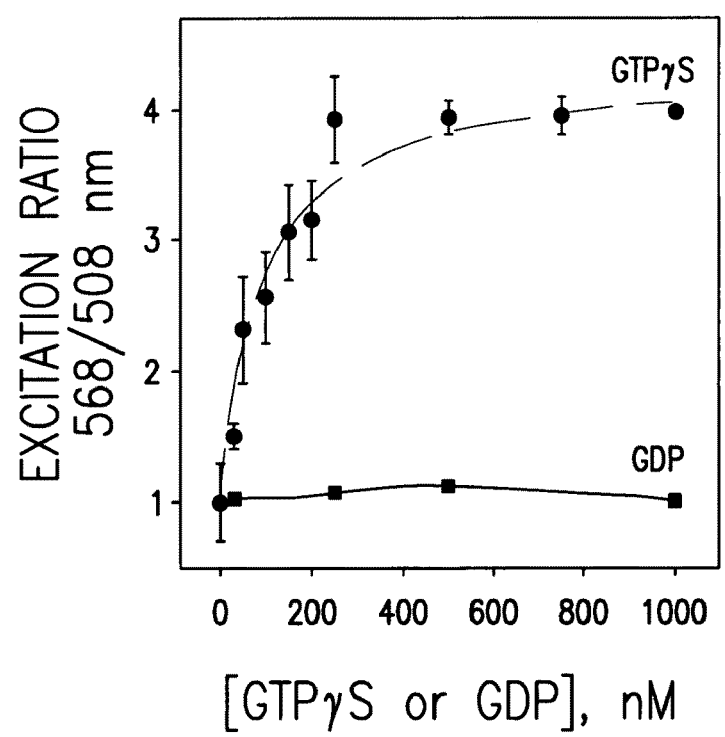
FIG. 7B shows the variation of the 568/508 nm emission ratios with changes in the level of GTP (solid circles) or GDP (solid squares). All data points were the average of three independent experiments.

FRET between Alexa-PBD and GFP-Rac1 was efficient and dependent on GTP-Rac 1 binding. Using fluorescence excitation wavelengths that selectively excite GEP (480 nm), fluorescence emission was monitored while maintaining a fixed concentration of GFP-Rac 1 and varying AlexaPBD concentrations (see FIG. 7a). Purified GFP-Rac1 (200 nM) was bound to varying concentrations of GTPδS or GDP at low magnesium by 30 min incubation at 30° C. as described previously (U. G. Knaus et al., J. Biol. Chem. 267, 23575-23582 (1992)), using the following nucleotide equilibration buffer: 50 mM Tris HCl (pH 7.6), 50 mM NaCl, 5 mM $MgCl_2$, 10 mM EDTA, and 1 mM DTT. Equal volumes of Alexa-PBD in the same buffer were added to the GFP-Rac1 solution and fluorescence emission spectra (500-600 nm) were acquired at room temperature and 480 nm excitation. Spectra were corrected for dilution upon Alexa-PBD addition. Alexa-PBD concentrations were either varied as shown, or maintained at 1 micromolar when saturating Alexa-PBD was required. The spectra shown were corrected for direct excitation of the Alexa fluorophore by acquiring spectra of Alexa-PBD alone at equivalent concentrations, and subtracting these from spectra shown in FIG. 7. $K_d$ were determined by fitting to the equation: $Y=A*X/(K_d+X)$. In the FIG. 7, panel A inset, only points actually used in the curve fitting are shown. Higher, saturating concentrations of AlexaPBD were not used because errors from subtraction of direct Alexa excitation became larger. Binding of Alexa-PBD to GFP-Rac resulted in a change in fluorescence intensity of both donor (GFP) and acceptor (Alexa) emission. When the GFP and Alexa fluorophores were brought into close proximity, FRET caused the Alexa (acceptor) emission to increase while the GFP (donor) emission decreased. No change in emission was observed when using either unlabeled PBD or Rac1 not fused to GFP, indicating that fluorescence changes were in fact due to energy transfer (data not shown). Because FRET alters donor and acceptor intensities in opposite directions, the ratio of emission at these two wavelengths is a sensitive measure of the PBD-Rac1 interaction. The corrected Alexa/GFP emission ratio underwent a 4-fold change upon saturation of Rac 1 with GTP (FIG. 7b). The change in emission ratio versus PBD concentration was fit to the Michaelis equation to derive an apparent $K_d$ for PBD-Rac1 binding of 1.1±0.3 µM (FIG. 7a inset). This is slightly higher than the values that have been determined for various unlabeled PAK1 fragments (E. Manser, T. Leung, H. Salihuddin, Z.-S. Zhao, L. Lim, Nature 67, 40-46 (1994); D. A. Leonard et al, Biochemistry 36, 1173-1180 (1997); G. Thompson, D. Owen, P. A. Chalk, P. N. Lowe, Biochemistry 37, 7885-7891 (1998). This may indicate that the presence of the Alexa may somewhat weaken the binding interaction. Our studies in live cells, described below, demonstrated that this affinity was sufficient for detection of Rac activation in vivo, and reversible binding is in fact desirable as it permits the biosensor to rapidly respond to changes in the location or level of Rac activation. Importantly, Alexa-PBD was shown to minimally perturb Rac-GTP binding interactions. The apparent GTPγS dissociation constant was determined at saturating Alexa-PBD by fitting the experimental data to the Michaelis equation (FIG. 7b). The derived value of 47±9 nM is consistent with the previously reported value of 50 nM (L. Menard, E. Tomhave, P. J. Casey, R. J. Uhing. R. Snyderman, J. R. Didsbury, Eur. J. Biochem. 206, 537-546 (1992). This validated application of FLAIR as an indicator of biologically relevant Rac-nucleotide binding.

Much is known about the localized dynamics of actin, but it has been difficult to explore how signals can generate precisely localized actin behavior. Rac has been shown to participate in signaling cascades leading to localized polymerization in several systems, but it is unclear whether Rac activity is constrained to specific subcellular regions, or whether global activation of Rac leads to more localized activation of downstream molecules. The precise spatial correlation of localized signaling and downstream actin behavior remains completely unknown. Here, we used FLAIR to study the localization and activation of Rac in two cell systems where actin behaviors are clearly constrained to specific subcellular regions, the induction of ruffling by growth factor stimulation of quiescent cells, and polarized cell motility induced by wounding.

We examined stimulation of quiescent Swiss 3T3 fibroblasts by serum or platelet derived growth factor (PDGF) known to initiate membrane ruffling and transcription through activation of Rac 1 (Ridley A. J., Paterson H. F., Johnston C. L., Diekmann D., Hall A., Cell 70, 401-10 (1992); P. T. Hawkins, Curr. Biol. 5(4), 393-403 (1995)). For serum stimulation experiments, Swiss 3T3 fibroblasts (ATCC, passage 15-27) were plated on glass cover slips and then maintained in Dulbeccos modified Eagle's medium (DMEM) with 10% fetal calf serum (FCS), 1% L-glutamine and 1% penicillin-streptomycin for at least 24 hours. Media was then replaced with media containing only 0.5% FCS, and cells were maintained for 42 hours. Cells were transfected by microinjecting 200 micrograms/ml GFP-Rac1 c-DNA into cell nuclei 2-8 hours prior to the experiment. The EGFP mutant was used in all experiments, cloned and expressed as previously described (C. Subauste et al, J. Biol. Chem. 275 (13), 9725-9733 (2000)). Cells expressing the GFP-Rac were then microinjected with 100 micromolar Alexa-PBD, mounted in a heated chamber on a Zeiss axiovert 100 TV microscope and maintained in Dulbecco's phosphate buffered saline (DPBS) (GIBCO) to reduce background fluorescence. Cells were then stimulated by replacing the media with DPBS containing 10% FCS or 50 ng/mL PDGF. Images were obtained every 30 seconds using a Photometrics PXL cooled CCD camera with 1×1 or 3×3 binning, and a Zeiss 40×1.3 NA oil immersion objective. Fluorescence filters from Chroma were as follows: GFP: HQ480/40, HQ535/50, Q505LP; FRET: D480/30, HQ610/75, 505LP; Alexa:HQ 545/30, HQ 610/75, Q565LP. Cells were illuminated using a 100 W Hg arc lamp. Exposure times for 3×3 binning were: GFP-0.1 seconds, Alexa-PBD-0.1 seconds, FRET-0.5 seconds. For 1×1 binning, GFP-1 second, Alexa-PBD-1 second, FRET-5 seconds.

Figure 8A:
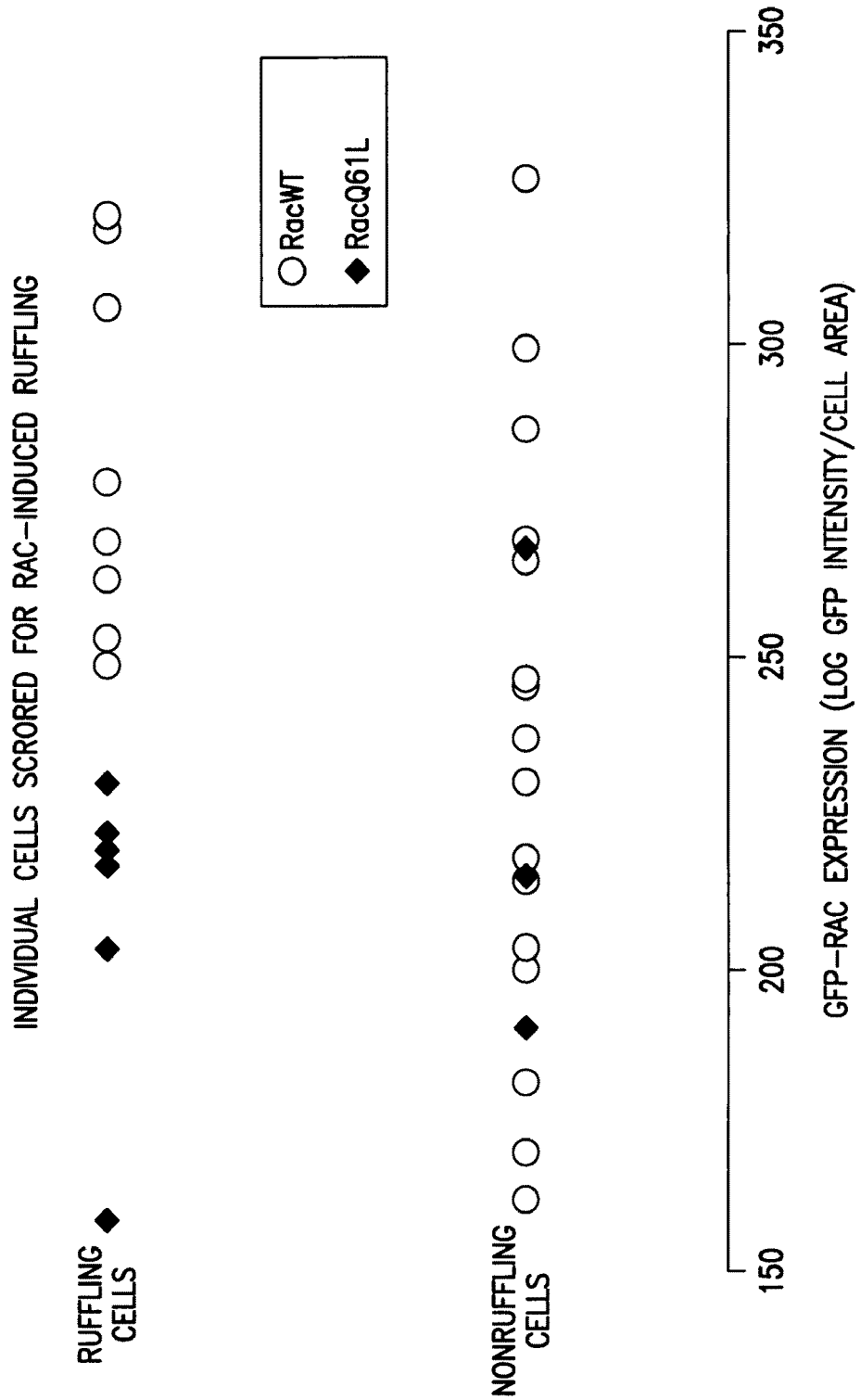
FIG. 8A shows what levels of GFP-Rac expression, as measured by log GFP intensity per cell area, were correlated with ruffling. Cells with different expression levels of either wild type or a constitutively active Q6 IL mutant of GFP-Rac were scored for ruffling. Each point represents an individual cell, placed in the higher (Ruffling) or lower (Nonruffling) row depending on whether ruffling was induced. As illustrated, there is a level of GFP intensity below which ruffling was consistently not induced by expression of wild type GFP-Rac. Only cells with Rac expression levels below 250 on this scale were used in biological experiments. The validity of this approach was supported by scoring of constitutively active Rac, which showed ruffle induction at much lower levels of expression.
Figure 8B:
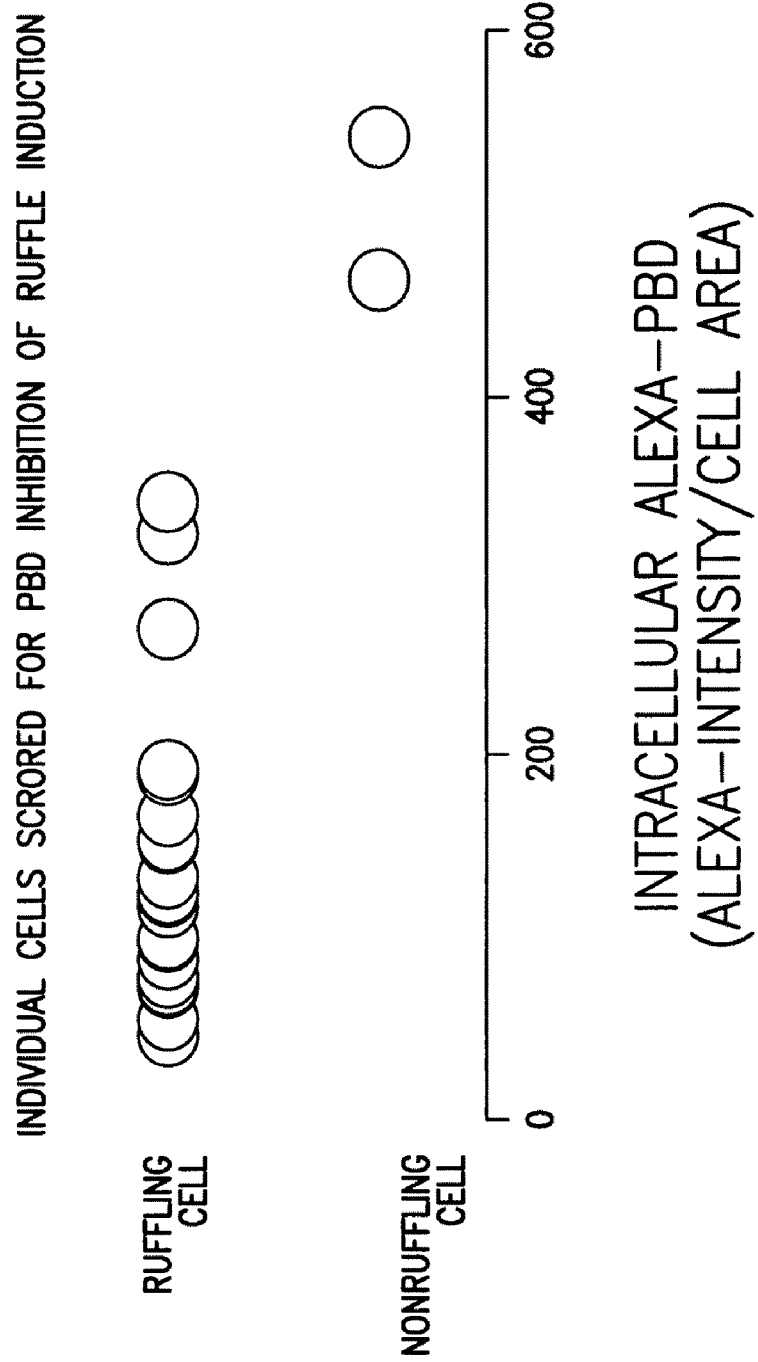
FIG. 8B shows which levels of intracellular Alexa-PBD would perturb normal serum-induced ruffling, as observed by Alexa intensity per cell area. Cells were scored as in FIG. 8A, at different levels of Alexa-PBD fluorescence. Based on this experiment, only cells with Alexa-PBD concentrations below 400 intensity units on this scale were used in biological experiments. These studies demonstrated that FRET could still be readily detected at appropriately low levels of introduced protein.

Levels of exogenous proteins had to be limited to concentrations that would not perturb cell behavior. We determined the intracellular levels of Alexa-PBD and GEP-Rac 1 that altered normal serum-induced ruffle formation (FIG. 8), and kept exogenous protein below these levels throughout our studies.

Figures 9A, 9B:
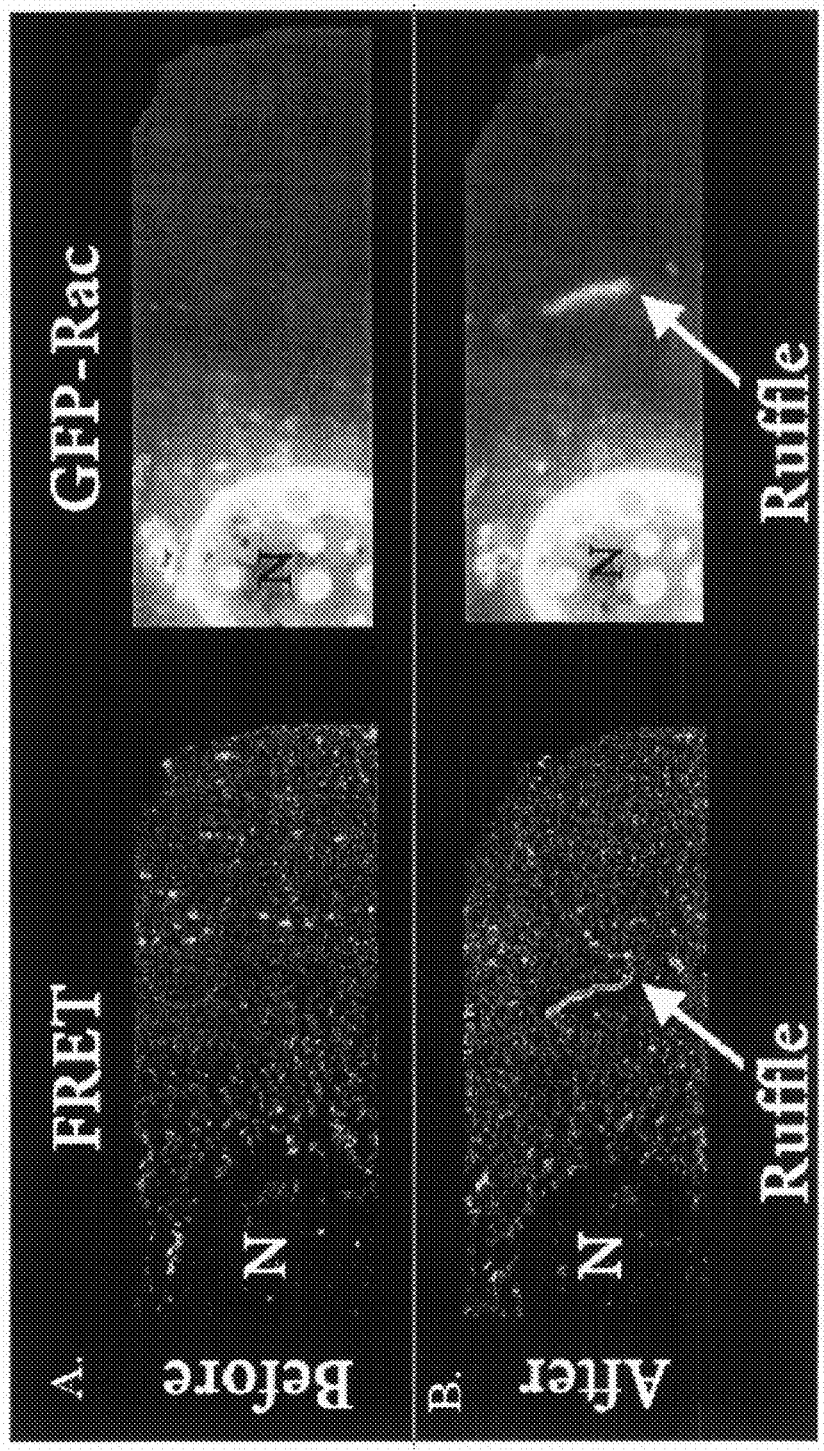
FIG. 9A provides photomicrographs showing Rac localization (GFP-Rac) and Rac activation (FRET) before stimulation of quiescent Swiss 3T3 fibroblasts.
FIG. 9B provides photomicrographs of the same Swiss 3T3 fibroblasts three minutes after addition of serum. Wanner or lighter colors correspond to higher intensity values. The cells showed accumulation of Rac at and around the nucleus before stimulation (GFP-Rac image). Most of the nuclear GFP-Rac was associated with the nuclear envelope. Serum or PDGF addition generated multiple moving ruffles that showed FRET, while no FRET was seen at the nucleus before or after stimulation. Of thirty-five cells stimulated with either serum or PDGF, thirty-one began ruffling within 15 minutes. FRET was seen in the ruffles of all but one of the ruffling cells.

Image triplets of GFP, FRET, and Alexa fluorescence were taken at each successive time point before and after stimulation. Thus, as shown in FIG. 9, both the changing localizations of GFP-Rac, and the level and location of Rac activation could be monitored. Images were first background subtracted and carefully registered to ensure accurate pixel alignment. The GFP-Rac image was then thresholded, changing the intensities of all pixels outside of the cell to zero. Thresholding was based on the GFP image since it had the largest signal to noise ratio, providing the clearest distinction between the cell and background. The thresholded GFP-Rac image was used to generate a binary image with all values within the cell=1 and all outside=0. The FRET and Alexa-PBD images were multiplied by the binary image, assuring that exactly the same pixels were analyzed in all three images. Emission appearing in the FRET image from direct excitation of Alexa and GFP was removed by subtracting a fraction of the GEP-Rac and Alexa-PBD images from the FRET image. This fraction depended on the filter set and exposure conditions used. It was determined, as described in detail elsewhere (C. E. Chamberlain, V. Kraynov, K. M. Hahn, *Methods Enzymology* (In Press 2000)), by taking images of cells containing only GFP-Rac or Alexa-PBD alone, and quantifying the relative intensity of emission in the FRET channel and that in the GFP or Alexa-PBD channel. A broad range of intensities was examined and a line was fit to these for accurate determinations. These corrections had to be applied carefully when studying rapidly moving objects such as ruffles. If the ruffle moved between acquisition of the FRET, GFP, or Alexa images, the subtractive correction process would remove light from the FRET image in the wrong place, generating artefactual FRET localizations. Data from moving features was used only when careful inspection showed the feature to be coincident in the Alexa, GFP, and FRET images, and controls were performed with images taken in different orders. A low pass filter kernel was applied to the corrected FRET image to remove high frequency noise (K. Castleman, *Digital Image Processing* (Prentice Hall, New Jersey, 1996), pp. 207-209). Image processing and microscope automation were performed using Inovision ISEE software. Images were contrast stretched and formatted for display using Adobe Photoshop software.

We tested Rac and PBD fused to GFP mutants that undergo FRET (ECFP and EYFP) (S. Dharmawardhane, D. Brownson, M. Lennartz, G. M. Bokoch, *J. Leukoc. Biol.* 66(3), p. 521-527 (1999); B. A. Pollok and R. Heim, *Trends Cell Biol.* 9(2), 57-60 (1999)). Unfortunately, their spectral overlap was more problematic than that of Alexa and GFP, making the corrections described here more difficult In addition, the GFP mutants showed roughly 25% the FRET of FLAIR. We decided to use FLAIR for these reasons, but the ability to monitor Rac activity simply through protein expression may justify using GFP mutants in some applications.

Simple GFP-Rac fluorescence revealed pools of Rac1 at the nucleus, in the juxtanuclear region, and in small foci throughout the cell prior to stimulation. Confocal and deconvolution imaging showed the nuclear Rac to be concentrated at the nuclear envelope, and expression and immunostaining of HA-tagged Rac1 indicated that these localizations were not an artifact of GFP tagging. Addition of PDGF or serum led to formation of moving ruffles throughout the cell periphery within 2 minutes. These contained GFP-Rac, shown by phalloidin staining of fixed specimens to colocalize with actin (data not shown). The FRET images showed a stark contrast between the level of Rac activation in the ruffles and the nucleus. No FRET was seen at the nucleus despite the high concentration of Rac1 there, while the moving ruffles showed the highest FRET, clearly restricted to the ruffle and discernable from the rest of the cell. The Rac activation remained tightly correlated with the position of the ruffle even as it moved throughout the cell.

As a negative control, FRET was imaged in cells expressing a mutant of GFP-Rho, a close relative of Rac that should not bind PBD. This GFP-Rho Q63L mutant, which generates high levels of GTP-bound protein, produced clear Rho localizations but no corresponding FRET signals (data not shown).

These studies provide the first direct evidence that Rac1 activation is restricted to the site of actin polymerization, independent of the overall distribution of the protein. Rac activation was tightly correlated with moving ruffles, indicating that structures specifically associated with the ruffle were either binding and concentrating activated Rac or that growth-factor induced Rac activation was specifically localized to ruffles. The function of the Rac found at the nuclear envelope remains uncertain. It may be activated for regulation of transcription at times later than those tested here, or may be activated for an unknown role by other stimuli. When activation was concentrated in a small area such as a ruffle, spatially resolved FRET could detect significant activation changes too small to appreciably alter the overall levels of cellular Rac activity. Our data showed that FRET provided much greater sensitivity and selectivity than following Rac activation simply by imaging Alexa-PBD localization (FIG. 9, panels C and D). FRET produces much lower backgrounds and provides complete selectivity even when the biosensor can bind to multiple proteins (i.e. Alexa-PBD also binds to cdc42). Unlike simple localization, FRET can provide quantitative measures of activation levels. It is important to note that the Alexa-PBD could have been sterically hindered from reaching Rac1 in some locations, so that not all activated Rac1 may have been detected. Nonetheless, a FRET signal in a given location does reveal that Rac activation is occurring there.

Rac has been shown to be essential for the directed movement of cells during chemotaxis, and for extension of the front end of cells during motility (C. Y. Chung et al, Proc. Natl. Acad. Sci. U.S.A. 97(10), 5225-5230 (2000). We used FLAIR to ask if Rac activation in polarized, motile cells occurred in particular subcellular localizations to regulate localized actin behaviors. A 'wound' was scraped in a monolayer of confluent Swiss 3T3 fibroblasts, causing cells to become polarized and move into the open space. For wound healing experiments, Swiss 3T3 fibroblasts were induced to undergo polarized movement as previously described (R. DeBiasio, G. R. Bright, L. A. Ernst, A. S. Waggoner, D. L. Taylor, *J. Cell. Biol.* 105, 1613-22 (1987). The cells were cultured in Dulbecco's modified Eagle's medium (GIBCO) supplemented with 10% fetal calf serum at 37° C. Cells were trypsinized and then plated on glass coverslips. They were grown to a confluent monolayer and maintained for an additional 3-4 days. Cells were then wounded by creating a straight laceration with a sterile razor blade. Cells along the edge of the wound were microinjected with 200 micrograms/ml GFP-Rac c-DNA. Six hours after the wound was formed, cells expressing the GFP-Rac were microinjected with 100 micromolar Alexa-PBD and allowed approximately 10 minutes for recovery. Media was then replaced with DPBS containing 10% FCS to reduce background fluorescence. Images were obtained as described above, using exposure times of 1 second for GFP, 1 second for Alexa-PBD, and 5 seconds for FRET. FLAIR revealed highest Rac activation in the juxtanuclear area, and a gradient of Rac activity highest near the leading edge and tapering off towards the nucleus (FIG. 10).

Quantitative analysis clearly indicated that the gradient was correlated with the direction of movement. In individual cells, total Rac activity was measured in two subcellular locations: where activity was highest at the front of the cell, and lowest at the very rear of the cell. These values, measured in squares three microns on a side, were used to calculate the gradient (Percent gradient=$100 \times$[front−back]/back). Of the 16 cells examined, twelve had higher Rac activity at the leading edge, while four showed a slight negative gradient. For cells with high Rac activity at the leading edge, the gradient was 128+/−51%, while for cells showing the reverse gradient, it was only 9+/−4% (mean+/−standard error). The gradient was much broader than the narrow area at the leading edge where actin polymerization occurs (Y. L. Wang et al, *J. Cell Biol* 101, 597-602 (1985; J. A. Theriot and T. J. Mitchison, *Nature* 352, 126-131 (1991). Other activities required for motility, such as depolymerization of fiber networks to recycle monomers and delivery of molecules to the leading edge (O. D. Weiner et al., *Nat. Cell. Biol.* 1, 75-81 (1999) occur throughout the region where Rac is activated. Perhaps Rac is acting over a broader cell area to activate multiple downstream effectors, each producing different effects in more restricted locations. Other studies have shown tight localization of molecules downstream of Rac, at the leading edge or in regions immediately behind it to regulate a variety of functions associated with motility (F. Michiels et al., *Nature* 375, 338-340 (1995).

The prevalence of Rac activation around the nucleus was quantified by scoring 16 cells. All cells showed both juxtanuclear and nuclear GFP fluorescence. Of these, fourteen showed juxtanuclear FRET, and none showed nuclear FRET. It was noteworthy that small areas of the nucleus sometimes showed a FRET signal, but these could be due either to cytoplasmic Rac associated with the nuclear envelope or to juxtanuclear localizations lying over the nucleus. The localization of activation within the juxtanuclear Rac often did not parallel Rac distribution, with "hot spots" of FRET within areas of lower Rac concentration. The meaning of the juxtanuclear Rac localizations is unclear, but their morphology and distribution suggests activation within the ER, golgi. or vesicle populations, perhaps consistent with recent reports suggesting an important role for Rac in ER to golgi transport (M. P. Quinlan, *Cell Growth Diff.* 10(12), 839-854 (1999), and in pinocytic vesicle cycling (Ridley A. J., Paterson H. F., Johnston C. L., Diekmann D., Hall A., Cell 70,401-10 (1992).

In summary, we have described a novel approach to quantify the spatial distribution and rapidly changing levels of Rac signaling in living cells. FLAIR provided the first direct demonstration that Rac activity is spatially regulated to generate specific actin behaviors in different subeellular regions. Activated Rac was tightly coupled to small membrane ruffles even as the ruffles moved throughout the cytoplasm, yet was broadly distributed as a gradient at the leading edge of motile cells. These very different activation patterns suggest that the cell will utilize different distributions of activated Rac depending on the number and localization of downstream targets.

Ultimately, FLAIR can reveal how different stimuli interact to affect Rac through the complex circuitry of an intact cell. We have focused here on spatial control of signaling. The ability of the biosensor to quantify the level and kinetics of activation should also prove very useful, as accumulating evidence indicates that Rac and related proteins do not function as simple binary switches. Different levels and kinetics of activation produce profoundly different results (T. Joneson, *Mol. Cell Biol.* 19(9) 5892-901(1999). Using FLAIR together with other biosensors of different wavelengths it should be possible to examine the balance between Rac, Ras, and other protein activation levels undergoing rapid changes in real time. With increasing access to FRET imaging equipment, the technique we describe provides a relatively straightforward way to greatly extend the utility of readily accessible GFP fusion proteins.

EXAMPLE 8

Activation Biosensors for cdc42 and Erk2

Like Rac, cdc42 is a member of the Rho family of small GTPases involved in signal transduction in eukaryotic cells. Cdc42 becomes "activated" by releasing GDP and binding GTP. Such GTPases interact with a host of downstream effectors, ultimately resulting in one or the other cellular response via a variety of phosphorylation cascades. In these experiments, a unique synthetic fluorophore with environment-sensitive fluorescence properties was linked to the cdc42 binding domain ("CBD") of the Wiscott-Aldrich Syndrome Protein (WASP) to generate a CBD biosensor. Upon binding to the cdc42, this fluorescent CBD biosensor is able to increase its fluorescence intensity by up to 3.5-fold, providing a convenient measure of endogenous cdc42 activation in living cells or for in vitro applications (concept outlined in FIG. 6b).

Mitogen-activated protein kinase (MAP kinase) was first identified as a protein phosphorylase which is activated when a growth factor is added to cultured cells (Proc. Natl. Acad. Sci. USA, 84, 1502-1506, 1987). However, subsequent research revealed that this enzyme is involved in various vital phenomena such as neuronal differentiation (J. Biol. Chem., 265, 4730-4735, 1990), activation of immune cells (J. Immunol., 144, 2683-2689, 1990) and secretions (J. Cell Biol., 110, 731-742, 1990). MAP kinase is also called Extracellular Signal-Regulated Kinase, or ERK. Cloning of the gene for human ERK gene showed that it consists of several molecular species with high homology, but the main species are two, namely ERK1 and ERK2. These two proteins are highly homologous (84.7%) (FEBS LETT., 304, 170-178, 1992). Mitogen-Activated Protein Kinase Kinase (called MEK) can interact with and stimulate ERK2.

Experimental Protocols:

Production of recombinant proteins. DNA encoding the Cdc42-binding fragment of human WASP containing the CRIB motif and surrounding amino acids (WASP amino acids 201 to 321) was amplified by PCR from ATCC clone #99534. This peptide fragment has the following amino acid sequence (SEQ ID NO:13).

```
DIQNPDITSSRYRGLPAPGPSPADKKRSGKKKISKADIGAPSGFKHVSHV

GWDPQNGFDVNNLDPDLRSLFSRAGISEAQLTDAETSKLIYDFIEDQGGL

EAVRQEMRRQEPLPPPPPS
```

The full sequence of the WASP protein is as follows (SEQ ID NO:14):

```
MSGGPMGGRP  GGRGAPAVQQ  NIPSTLLQDH  ENQRLFEMLG

RKCLTLATAV  VQLYLALPPG  AEHWTKEHCG  AVCFVKDNPQ

KSYFIRLYGL  QAGRLLWEQE  LYSQLVYSTP  TPFFHTFAGD

DCQAGLNFAD  EDEAQAFRAL  VQEKIQKRNQ  RQSGDRRQLP

PPPTPANEER  RGGLPPLPLH  PGGDQGGPPV  GPLSLGLATV

DIQNPDITSS  RYRGLPAPGP  SPADKKRSGK  KKISKADIGA
```

```
                       -continued
PSGFKHVSHV  GWDPQNGFDV  NNLDPDLRSL  FSRAGISEAQ

LTDAETSKLI  YDFIEDQGGL  EAVRQEMRRQ  EPLPPPPPS

RGGNQLPRPP  IVGGNKGRSG  PLPPVPLGIA  PPPPTPRGPP

PPGRGGPPPP  PPPATGRSGP  LPPPPPGAGG  PPMPPPPPPP

PPPPSSGNGP  APPPLPPALV  PAGGLAPGGG  RGALLDQIRQ

GIQLNKTPGA  PESSALQPPP  QSSEGLVGAL  MHVMQKRSRA

IHSSDEGEDQ  AGDEDEDDEW  DD
```

The DNA fragment encoding SEQ ID NO:13 was subcloned into pET23a (Novagen) as a C-terminal 6His fusion. Site-specific cysteine mutants were constructed by QuikChange (Stratagene) mutagenesis using synthetic oligos and the presence of mutations was confirmed by DNA sequencing. Resultant constructs were transformed into BL21DE3 strain of E. coli (Novagen), and the proteins were produced by expression at 30° C. for 5 hours in 1 L Leuria-Bertani media (Sigma) in the presence of 100 µg/ml of carbenicilin. Expression was induced with 0.5 mM IPTG at $OD_{600}$=0.8-1. Cells were collected by centrifugation and stored at −20° C. until use.

Cell pellet was resuspended in cold lysis buffer (25 mM Tris-HCl, pH 7.9, 150 mM NaCl, 5 mM $MgCl_2$, 5% glycerol, 1 mM PMSF, 2 mM β-mercaptoethanol), and briefly sonicated on ice. Lysozyme and DNase were added to the suspension to a final concentration of 0.1 mg/ml and 100 U/ml, respectively, and solution was incubated with occasional stirring at 4° C. for 30 min. Lysate was centrifuged (12,000 g, 30 min), and the clarified supernatant was incubated with 1 ml of Talon resin (Clontech) at 25° C. for 30 min. The resin containing bound CBD was separated from the lysate by brief low-speed centrifugation and washed twice with 15 ml of lysis buffer. Finally, the resin was washed with the lysis buffer, supplemented with 10 mM imidazole, and poured into a column. Elution was performed with 5 ml of the lysis buffer, containing 60 mM imidazole. Fractions containing bulk of CBD (as evidenced by SDS gel) were combined and dialyzed against 1 L of dialysis buffer (25 mM $Na_2HPO_4$ (pH 7.5), 10 mM NaCl) for 5 hours at 4 C. Solution was then concentrated using Aquacide powder to a final protein concentration of 2 to 10 mg/ml, and dialyzed once again against dialysis buffer. Final preparation was flash-frozen in 100 µL aliquots and stored at −80° C. Generally, 1 to 3 mg of CBD was obtained from 1 L of cell culture. Recombinant 6His-tagged cdc42, RhoA, Rac1, ERK2 and MEK were produced by analogous procedures. The enzymes were determined to be >90% active by the GTP binding assay (Knaus, U. G., Heyworth, P. G., Kinsella, B. T., Cumutte, J. T., and Bokoch, G. M. (1992) J. Biol. Chem. 267, 23575-23582).

Conjugation of CBD with fluorescent dyes—Dialyzed CBD samples (100-150 µM) were gently inverted with 6 to 7-fold molar excess of the reactive dye at 25° C. for 3 to 4 hours. The reaction was stopped by addition of 10 mM dithiothreitol (DTT), and the mixture was incubated for 15 min. Unreacted dye was separated from the labeled protein using G25-Sepharose (Pharmacia) gel filtration column equilibrated and developed with 25 mM $Na_2HPO_4$ (pH 7.5). Purity of the eluting fractions was analyzed by running an aliquot on an SDS gel and visualizing the fluorescence. Only the fractions containing minimal amounts of free dye were used in the subsequent experiments. Dye-to-protein ratio was determined by measuring CBD concentration ($\epsilon^{280}$=8,250 $M^{-1}$), and A4C concentration at 617 nm ($\epsilon$=70,000 M$^{-1}$ in dimethylsulfoxide) or Alexa546 at 554 nm ($\epsilon$=104,000 M$^{-1}$ in 50 mM potassium phosphate, pH 7.0). Concentrations of CBD were independently confirmed by Coomassie Plus assay (Pierce) calibrated with bovine serum albumin as a standard. Dye-to-protein ratios thus obtained varied between 0.8 and 1.2, 1.7 and 2.1 for the single-dye and dual-dye conjugates, respectively. Aliquots of the labeled CBD (15 to 50 μM) were stored at −80° C. No significant loss of binding ability was observed after 6 months of storage. In this example, CBD-conjugates were made with the dye shown in FIG. 11, and are referred to as mero-CBD (for merocyanines dye conjugated to CBD).

Dye Attachment Single Site on ERK2—The ERK2-dye adduct was produced using conditions which should label only the single solvent-exposed cysteine on ERK. This exposed cysteine was located away from known protein interaction sites. A maleimide reactive group on the dye was attached to this cysteine residue at pH 7.5. The attachment of label and the activation of ERK2 was examined under different conditions (FIG. 23). ERK2 was activated with MEK for 0-60 min, as indicated in FIG. 23. When Mg and ATP were added, ERK2 was phosphorylated; no such phosphorylation was observed when no Mg, ATP or MEK was present (FIG. 23).

Fluorescence increase as a measure of ERK2-MEK interaction—The functionality and specificity of ERK2 biosensor was characterized by measuring fluorescence in the presence and absence of saturating amounts of ATP (FIGS. 24 and 25). An approximate 1.6-fold increase in emission was observed, when the Erk2 was phosphorylated (FIG. 24). No effect on Erk2 fluorescence was observed when no MEK was present (FIG. 25). This result demonstrated the suitability of the present methods for detecting activation of ERK2 in live cells.

Analyses of the solvatochromic activation indicator—A solution of mero-CBD (300 nM) in assay buffer was mixed 1:1 (v/v) with solutions of cdc42 (concentration as indicated), pre-equilibrated with 10 mM GDP or GTPγS as described in Knaus, U. G., Heyworth, P. G., Kinsella, B. T., Cumutte, J. T., and Bokoch, G. M. (1992) *J. Biol. Chem.* 267, 23575-23582. Emission wavelength of 630 nm and excitation wavelength of 600 nm were used to acquire excitation and emission spectra, respectively. For nucleotide dependence, cdc42 (500 nM) was pre-incubated with varying concentrations of GTPγS (1 to 500 nM). Rac1 and RhoA GTPases were pre-equilibrated with GTPγS in the same manner.

Assay of cdc42 activity in stimulated neutrophil cell lysates.—Freshly prepared neutrophils (2.5×10$^7$ cells/sample) were incubated in a Krebbs-Ringer HEPES buffer supplemented with 5.5 mM glucose (KHRG), in the presence of 1 mM CaCl$_2$ and 1 μM of fMet-Leu-Phe tripeptide (FMLP) for various periods of time at 37° C. (see Benard, V., Bohl, B. P., and Bokoch, G. M. (1999) *J. Biol. Chem.* 274, 13198-13204). Stimulation was stopped by adding equal volume of 2× lysis buffer, supplemented with 2% Nonidet P-40, 2 μg/ml aprotinin. After a brief vortexing the lysates were clarified by centrifugation and immediately analyzed for cdc42 activity with mero-CBD as described above. In control samples, the lysates were pre-equilibrated with either GDP or GTPγS at 30° C. for 20 to 30 min. This was a convenient method to determine the extent of cdc-42 activation in cell lysates, as shown in FIG. 16.

Using the structural information available (Abdul-Manan et al. (1999) *Nature* 399, 379-383; Kim et al. (2000) *Nature* 404, 151-158), we had selected three positions for placing the fluorescent dye within the CBD peptide (I233, D264 and F271, by WASP numbering), that could experience a considerable change in solvent polarity as a result of binding to cdc42 (see FIG. 14). F271 and D264 are located in the loop contacting the effector "switch" domain of the GTPase, whereas I233 appears to interact with the hydrophobic pocket formed by residues at the N-terminus of cdc42 (see FIG. 14). The three CBD residues were mutated to cysteines, easily amenable to covalent modification with the thiol-reactive derivatives of the solvatochromic dyes. Recombinant mutant CBD proteins were overexpressed in bacteria, purified and site-specifically modified with several of solvatochromic dyes. Only the conjugates with the dye shown in FIG. 11 are described here.

Among the three mutants tested, the mero-CBD-F271 C conjugate exhibited the largest (ca 3.5-fold) fluorescence change in response to binding of activated cdc42 (see FIG. 15).

Fluorescence increase as a measure of CBD-cdc42 interaction—The functionality and specificity of mero-CBD was characterized by measuring fluorescence in the presence of saturating amounts of cdc42-GDP or cdc42-GTPγS. Approximately 3.5-fold increase in both excitation and emission maxima was observed, when the probe was bound to cdc42-GTPγS, but not cdc42-GDP. Negligible increase (<5%) was also observed in the presence of activated Rac1. No effect on the mero-CBD fluorescence was observed when RhoA-GTPγS was present. Furthermore, even in the presence of excess of activated Rac1 and RhoA, GDP- and GTPγS-bound forms of cdc42 were easily distinguished by CBD-A4C fluorescence (data not shown). This result demonstrated the suitability of the CBD bisensor for use in live cells where different Rho GTPases may be present at comparable concentrations.

FIG. 17 demonstrates use of the biosensor in living cells. To eliminate potential artifacts due to varying cell thickness, uneven illumination, etc., the biosensor was loaded into the cell together with CBD labeled with nonresponsive Alexa546 fluorophore. The ratio of the mero-CBD image to the CBD-Alexa image provided a quantitative measure of the extent of GTPase activation. The lighter, warmer colors show areas of higher cdc42 activation.

EXAMPLE 9

Rhodamine-Tagged Peptide Biosensors

Proteins within living cells were fluorescently labeled in situ, without isolation or reintroduction of the protein. A short peptide tag derived from the leucine zipper of GCN4 transcription factor was fused to a cellular protein and this fusion protein was expressed in live cells. A second peptide from GCN4, which binds with high affinity to the peptide fused onto the cellular protein, was covalently labeled with rhodamine and also introduced into live cells, where it specifically and selectively labeled the tagged protein. Attachment of rhodamine at the chosen site provided good peptide-peptide binding affinity (5 nM Kd). Two proteins were labeled and visualized in living cells, the cytoplasmic protein α-actinin, and a protein spanning the endoplasmic reticulum (ER) membrane, the α-chain of the high affinity IgE receptor (F$_c$εRI). The latter membrane bound protein has previously been inaccessible to synthetic dye attachment through isolation and labeling.

Materials and Methods

Peptide synthesis. Peptides were synthesized manually using solid-phase methods with in situ neutralization and HBTU activation procedures for Boc chemistry, on either —OCH2-Pam or MBHA resins as previously described. Standard Boc-protecting groups strategies were employed except for Lys 21 on the labeled peptide, which was protected with an FMOC base-labile protecting group to allow for selective deprotection. Purification was performed using reversed-phase high performance liquid chromatography (RP-HPLC) to obtain peptides greater than 95% pure by analytical HPLC (UV detection at 214 nm and linear gradients of solvent B (0.09% TFA in 90% acetonitrile/10% water) in solvent A (0.1% TFA in water)). Labeled peptide expected mass (w/o FMOC)=3846, observed mass=3846+/−0.7. Protein tag peptide expected mass=3735, observed mass=3735+/−0.7.

Derivatization of the Labeled Peptide at Lys 21 with Rhodamine.

The labeled peptide employed had the following sequence.

CEMAQLEKEVQALESEVASLEKEVQALEKEVAQR-NH$_2$ (SEQ ID NO: 15)

This peptide binds with specificity to the following peptide ("tag") sequence.

KMAQLKKKVQALKSKVASLKKKVQALKKKVAQR-NH$_2$ (SEQ ID NO: 16)

Lysine 21 of the peptide having SEQ ID NO:15 was selected as the site for tetramethylrhodamine attachment. During Boc-solid phase synthesis, the lysine was protected with a fluorenylmethyloxy-carbonyl protecting group, enabling selective deprotection and ready labeling while the peptide was still attached to the synthesis resin. Peptides containing three heptamer repeats were used to produce low nanomolar affinities.

To begin the attachment procedure, 20 mg N-hydroxysuccinimide (0.174 mmol) and 30.6 mg of 5-(and 6-) tetramethylrhodamine (0.071 mmol) were dissolved in 300 microliters of DMF. To this mixture, 10.85 microliters of diisopropylcarbodiimide were added. The reaction was then mixed and incubated at room temperature for 2 hours. After 2-3 minutes, diisopropylurea precipitation was evident in the activated dye reaction. 200 mg of resin with attached peptide (~0.05 mmol peptide) was treated 3 times with 50% piperidine in DMF to selectively remove the FMOC protection of Lys 21 (total piperidine deprotecton time was 15 minutes). Deprotection of Lys 21 was confirmed by quantitative ninhydrin assay. After FMOC removal, the resin was thoroughly washed with DMF and drained completely. The in situ activated tetramethylrhodamine N-hydroxysuccinimide ester was diluted to 400 microliters and added to the peptide-bearing resin dropwise until the resin was saturated with activated dye solution. The reaction was incubated at room temperature for 4 hours, washed with DMF and then with DCM/MeOH (1/1) until washes contained minimal color (4-5 washes each). The resin was dried under vacuum overnight. Standard protocols for cleavage/deprotection and purification of tetramethylrhodamine-labeled label peptide were utilized. Expected mass=4258, Observed mass=4258+/−0.36.

Peptide in vitro interaction measurements. Steady-state fluorescence measurements were performed on an SLM 8100 spectro-fluorometer at 25° C. with spectral bandwidths set to 8/16/8 nm and 16/16 nm for excitation and emission, respectively. The absorption of the tetramethylrhodamine (TMR) dye linked to the lysine side-chain was used to calculate the solution concentration of the peptide in 10 fold diluted PBS, using the assumption that the extinction coefficient of lysine-linked TMR is the same as that of free dye. The TMR absorption maximum was 553 nm on the peptide vs. 550 for free dye. The extinction coefficient of the free dye was 75916 M$^{-1}$ cm$^{-}$. For these assays only, the sequence YGRKKRRNRRRP (SEQ ID NO:17) was appended to the N-terminus of the rhodamine-containing peptide, as this sequence was being tested in a parallel study of cell import. For the anisotropy titrations, the labeled peptide at a concentration of 12.52 nM was incubated with a stock solution of unlabeled peptide in 0.1× PBS. Titrations were performed at magic angle setting with the excitation wavelength set to 553 nm and the emission wavelength to 580 nm. The spectra were corrected for Raman scattering from the PBS solution, for dilution, and checked for interactions of the label with the ligand by a parallel titration with label peptide using 5-carboxytetramethylrhodamine in PBS in the reference cuvette. For each addition of unlabeled peptide, ten anisotropy measurements were taken, and the total intensity and anisotropy were calculated according to standard equations with the G-Factor consistency determined at each titration point. The average of the anisotropy was used for data analysis. Standard deviations were <1%. If the quantum yield of the fluorophore changed upon binding, this change had to be taken into account for calculation of the ratio between free and bound biosensor-tag. The anisotropy binding data were therefore fit to the following equation that describes the anisotropy enhancement of tetramethylrhodamine in the labeled peptide (TMRPep) as function of the total concentration of added unlabeled peptide (UPep).

$$r = \frac{r_{min} + \frac{(r_{max} * Q - r_{min}) * [TMRPep/UPep]}{[(TMRPep)\circ]}}{1 - (1 - Q) * \frac{[TMRPep/UPep]}{[(TMRPep)\circ]}}$$

with $Q=q_{bound}/q_{free}$, the ratio between quantum yield of TMRPep in bound to free form, and $[TMRPep/UPep]=([TMRPep]+[UPep]+Kd]-(([TMRPep]+[UPep]+Kd])^2-4*[TMRPep]_0*[UPep]_0)^{1/2})/2*[TMRPep]_0$.

Expression Constructs

The various constructs used in this study were similarly prepared using standard cloning (Sambrook et al) of PCR-generated coding sequences into the indicated vectors. The sequence of all constructs was confirmed using an ABI model 377 version 3.0 DNA sequencer.

Cloning pEGFP-α-actinin1-peptide tag. The oligonucleotides, 5'GAGCTGTACAAGGGAGG-CATGAAGATGGC-CCAGCTG AAG 3' (SEQ ID NO:18) and 5'GTCGCGGC-CGCCTTATCGCTGGGCCAC-CTTCTTC3' (SEQ ID NO:19) synthesized by Gibco Life Technologies, were used to amplify the peptide tag insert. The humanized DNA sequence for the peptide tag, derived from the available peptide, was amplified from pCDNA-Nova2-EGFP-cdc42 (T17N) to incorporate a BsrGI restriction site on the 5' end and a NotI restriction site on the 3' end. These blunt end PCR products produced by pfu polymerase were ligated into pEGFP-N1-α-actinin. After BsrGI and NotI restriction enzymes were used the construct was gel purified (Qiagen Qiaquick Gel Extraction Kit) and ligated with T4 ligase (Gibco, Life Technologies) into the pEGFP-N1-αactinin1 vector downstream of EGFP. The pEGFP-N1-α-actinin1-Nova2 sequence was verified through sequencing performed by The Scripps Research Institute core facility.

Cloning of peptide-tagged FcεRI α-chain. The cDNA encoding the human high affinity IgE receptor (FcεRI) α-chain containing the NOVA-2 tag positioned at C-terminus was generated by a succession of four PCR reactions to sequentially build the desired full length coding sequence, which was then cloned into the pcDNA3.1(+)zeo vector (Invitrogen, Carlsbad, Calif.) to sequentially build the desired full length coding sequence. Each amplification used the 5' primer: 5'-GACTGGATCCGAGTCCATGAAGAAGATG-GCTCCTGCC (SEQ ID NO:20) together with the 3' primers described below, using human FcεRI α-chain plasmid as template and Pfu polymerase (Stratagene, San Diego, Calif.) with 25-30 cycles of 94° C. for 1 min; 65° C. for 1 min; and 72° C. for 2 min, followed by one cycle of 72° C. for 10 min. The following downstream PCR primers were used to generate PCR products 1-4, respectively.

(SEQ ID NO: 21)
1:5' CTGAACTTTCTTCTTGAGCTGGGCCATCTTACTTCCGCCACCGTTG

TTTTTGGGGTTTGGCTTAGG;

(SEQ ID NO: 22)
2:5' CACCTTTTTCTTCAAGCTCGCCACTTTGCTCTTGAGCGCCTGAACT

TTCTTCTTGAGCTGGGC;

(SEQ ID NO: 23)
3:5' GGCCTCGAGTCAACGTTGAGCGACTTTCTTTTTTAAGGCTTGCACC

TTTTTCTTCAAGCTCGCCAC;

(SEQ ID NO: 24)
4:5'-CTCGATCGCTCGAGTCAACGTTGAGCGACTTTCTT.

The full-length PCR product from reaction 4 was isolated and then cloned as a Xho I/Hind 3 fragment into the pcDNA3.(+) zeo vector (Sambrook, J., E. F. Fritsch, and T. Maniatis. 1989. *Molecular Cloning: A Laboratory Manual*, 2nd ed., Cold Spring Harbor Laboratory Press, Plainview, N.Y.). The nucleotide sequence of the NOVA2-tagged α-chain coding sequence was confirmed on an ABI model 377 version 3.0 DNA sequencer.

Cloning of the GFP-MHC HLA B27 Fusion Protein.

The GFP protein was fused to the ER-resident major histocompatability complex I glycoprotein $D_b$ (MHC). The cDNA encoding the human HLA B27 was generated by PCR amplification using the following oligonucleotide primers: 5'-GGGGATCCTCTCAGACGCCG-3' (SEQ ID NO:25) and 5'-CATGCCATGGCTCCGGATCCACCAGCT-GTGAGAGACAC-3' (SEQ ID NO:26) to produce BamHI and NcoI ends. This product was ligated with the GFP coding sequence that had been previously excised from the pSGFP vector as a NcoI-NotI fragment. This ligation product was then cloned the into the BamHI-NotI sites of the vector pcDNA3 to produce the desired MHC-GFP fusion protein construct.

Cell culture and imaging. Cos-7 cells were cultured and transfected with FuGENE6 (Roche Molecular Biochemicals) according to the manufacturer's protocol. Cells expressing EGFP-α-actinin were microinjected with 20-μM Rhodamine-labeled peptide in water. After injection, cells were washed with Dulbecco's phosphate buffered saline (DPBS) (Life Technologies) with 10% FBS, then mounted in a heated chamber on a Zeiss Axiovert 100 TV microscope and maintained in DPBS with 10% Fetal Bovine Serum (FBS) to reduce background fluorescence. Images were obtained using a Photometrics PXL cooled CCD camera with 1×1 binning, and a Zeiss Fluar 40×1.3 NA oil immersion objective. Fluorescence filters from Chroma were as follows: GFP: HQ480/40, HQ535/50, Q505LP; Rhodamine: HQ545/30, HQ610/75, Q565LP. Images were background subtracted and contrast stretched using Inovision ISEE software, then formatted for display using Adobe Photoshop software.

Results

To assess the ability of the peptide to maintain tight binding after labeling with dye, the affinity of the labeled peptide-peptide tag interaction was determined by equilibrium fluorescence titration, monitoring the changes in anisotropy and fluorescence intensity (see FIG. 18). High affinity was critical for live cell fluorescence imaging to maximize the proportion of labeled peptide bound to the targeted protein. Unattached labeled peptide could reduce sensitivity by generating uniform fluorescence background, and higher free peptide concentrations could perturb normal cell function or generate appreciable nonspecific binding. Upon binding, the labeled peptide showed a drop in quantum yield and a more than 230% increase in rhodamine anisotropy, indicating considerable reduction in rotation of the dye. Fitting the anisotropy values and peptide concentrations to a quadratic equation describing a simple 1:1 binding interaction (see experimental procedures) indicated that the interaction had a Kd value of 5.4±1.1 nM. This high affinity suggested that there was little or no influence of the dye on the peptide-peptide interaction.

Next, α-actinin in living cells was visualized and the fluorescence of the GFP-fusion protein was compared to that of the peptide labeled with rhodamine. An α-actinin construct with GFP fused to the N-terminus and the tag peptide on the C-terminus was expressed in Cos-7 cells. These cells were loaded with rhodamine peptide through microinjection. The concentration of the rhodamine-labeled peptide was optimized at 20 μM to minimize background fluorescence while clearly labeling the tagged peptide. We had determined previously that a uniform fluorescence background is not a serious obstacle using other fluorescently labeled proteins, including rhodamine actin in cytoskeletal fibers, which produces a physiologically normal background of unpolymerized protein.

FIGS. 19a and 19c show GFP images and FIGS. 19b and 19d show rhodamine images taken of the same cells. The fluorescence from a different cell is shown in FIG. 20. The peptide tag gave remarkably detailed images of α-actinin distribution, which was difficult to distinguish from those obtained using GFP. Controls in which only the rhodamine-peptide or the α-actinin GFP were present in the cell proved that the colocalization of the rhodamine and GFP signals was not due simply to imperfect selectivity of the fluorescence filters used to separate rhodamine and GFP signals. (See FIG. 21.) These controls also demonstrated that binding to other leucine zipper proteins or undesired sites was not a problem, although a slight affinity of rhodamine for the nuclear envelope could be seen.

An important advantage of our labeling methodology is the ability to label proteins that cannot be readily isolated or reintroduced in the cell. This was demonstrated by fusing the tag peptide to the C-terminus of the $F_c$εRI, a membrane-spanning protein that remains in the endoplasmic reticulum unless co-expressed with the $F_c$εRI γ-subunit. The tagged protein was expressed in Cos-7 cells together with a GFP fusion of the ER-resident major histocompatability complex I glycoprotein $D_b$ (MHC), used here as an ER marker.

FIG. 22 shows that the ER-localized $F_c$εRI α-chain was clearly visualized using the rhodamine-tagged peptide. The distribution of the two proteins was not identical, with the Fc receptor showing some concentrations in the perinuclear region. Controls using each fluorescent species alone in cells showed that results were not due to bleedthrough of emission from one fluorophore into the image of the other, and that localizations were not the result of nonspecific binding (data not shown).

In summary, this approach provides access to many proteins which were previously very difficult to label with synthetic fluorophores for live cell experiments. Unlike other methods requiring relatively difficult synthesis of reagents or bulky antibody tags, this procedure can be accomplished using routine cloning and peptide synthesis procedures.

All publications, patents, and patent documents are incorporated by reference herein, as though individually incorporated by reference. The invention has been described with reference to various specific and preferred embodiments and techniques. However, it should be understood that many variations and modifications can be made while remaining within the spirit and scope of the invention.

---

What is claimed:

1. A method for detecting binding of an antibody to an antigen which comprises reacting an antibody with an antigen and detecting an antibody-antigen complex, wherein the antibody is conjugated to a fluorescent compound of the formula:

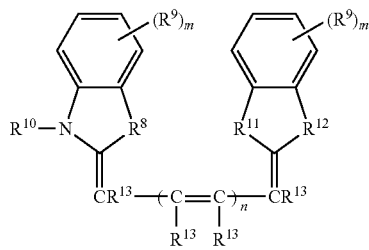

wherein:
  each m is separately an integer ranging from 1-3;
  n is an integer ranging from 0 to 5;
  $R^8$, $R^{11}$ and $R^{12}$ are separately CO, $SO_2$, C=$C(CN)_2$, S, O or $C(CH_3)_2$;
  each $R^{13}$ is alkyl, branched alkyl or heterocyclic ring derivatized with charged groups to enhance water solubility and enhance photostability;
  each $R^9$ and $R^{10}$ is separately an alkyl chain derivatized with charged groups to enhance water solubility or with reactive groups for conjugation to other molecules.

2. A method for detecting binding of an antigen to an antibody which comprises reacting an antigen with an antibody and detecting an antibody-antigen complex, wherein the antigen is conjugated to a fluorescent compound of the formula:

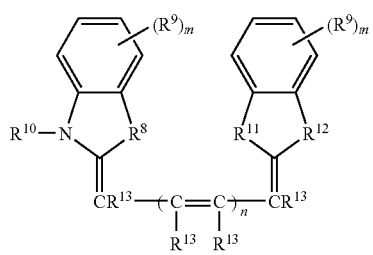

wherein:
  each m is separately an integer ranging from 1-3;
  n is an integer ranging from 0 to 5;
  $R^8$, $R^{11}$ and $R^{12}$ are separately CO, $SO_2$, C=$C(CN)_2$, S, O or $C(CH_3)_2$;
  each $R^{13}$ is alkyl, branched alkyl or heterocyclic ring derivatized with charged groups to enhance water solubility and enhance photostability;
  each $R^9$ and $R^{10}$ is separately an alkyl chain derivatized with charged groups to enhance water solubility or with reactive groups for conjugation to other molecules.

3. The method of claim 1 wherein each $R^9$ and $R^{10}$ is separately sulfonate, amide or ether.

4. The method of claim 1 wherein each $R^9$ and $R^{10}$ is separately —NH—(C=O)—$CH_2$-halide, amine, maleimide, —N=C=O, —N=C=S, acyl halide, succinimidyl ester, sulfosuccinimidyl ester, sulfonyl halide, sulfonyl azide, alcohol, thiol, semicarbazide, hydrazine or hydroxylamine.

5. The method of claim 1 wherein each $R^9$ and $R^{10}$ is separately carboxylic acid, alkali or alkaline earth metal salt of carboxylic acid, carboxylic acid activated by carbodiimide, acyl chloride, succinimidyl, sulfosuccinimidyl ester or COORx, wherein Rx is phenol or naphtol further substituted by at least one strong electron withdrawing group.

6. The method of claim 1 wherein the fluorescent compound has the formula:

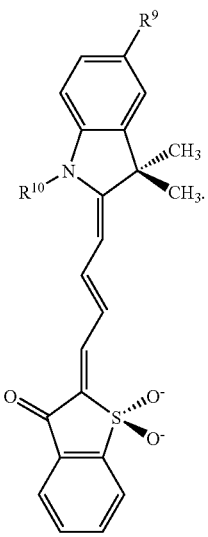

7. The method of claim 1 wherein the fluorescent compound has the formula:

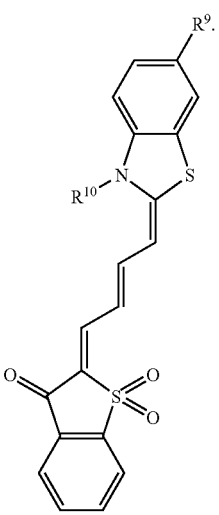

8. The method of claim 1 wherein the fluorescent compound has the formula:

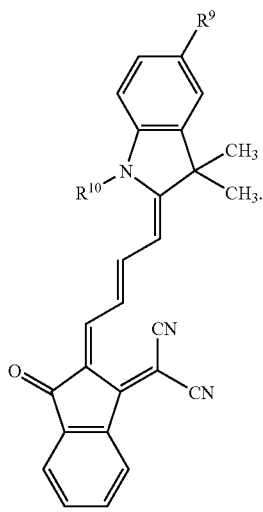

9. The method of claim 2 wherein each $R^9$ and $R^{10}$ is separately sulfonate, amide or ether.

10. The method of claim 1 wherein each $R^9$ and $R^{10}$ is separately —NH—(C=O)—CH$_2$-halide, amine, maleimide, —N=C=O, —N=C=S, acyl halide, succinimidyl ester, sulfosuccinimidyl ester, sulfonyl halide, sulfonyl azide, alcohol, thiol, semicarbazide, hydrazine or hydroxylamine.

11. The method of claim 1 wherein each $R^9$ and $R^{10}$ is separately carboxylic acid, alkali or alkaline earth metal salt of carboxylic acid, carboxylic acid activated by carbodiimide, acyl chloride, succinimidyl, sulfosuccinimidyl ester or COORx, wherein Rx is phenol or naphtol further substituted by at least one strong electron withdrawing group.

12. The method of claim 2 wherein the fluorescent compound has the formula:

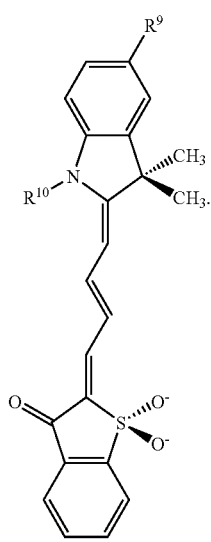

13. The method of claim 2 wherein the fluorescent compound has the formula:

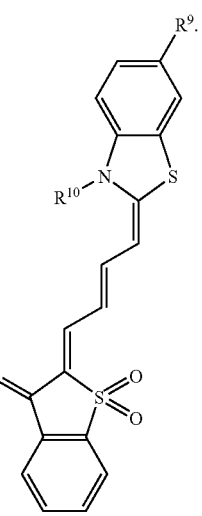

14. The method of claim 2 wherein the fluorescent compound has the formula:

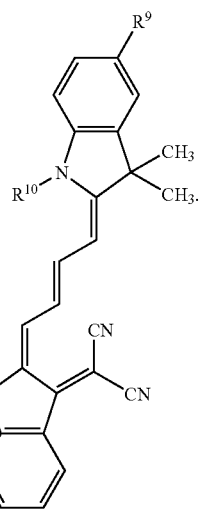

15. An antibody covalently linked to a fluorescent compound of the formula:

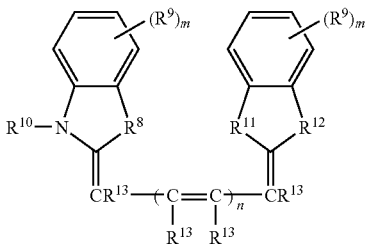

wherein:

each m is separately an integer ranging from 1-3;

n is an integer ranging from 0 to 5;

$R^8$, $R^{11}$ and $R^{12}$ are separately CO, $SO_2$, $C=C(CN)_2$, S, O or $C(CH_3)_2$;

each $R^{13}$ is alkyl, branched alkyl or heterocyclic ring derivatized with charged groups to enhance water solubility and enhance photostability;

each $R^9$ and $R^{10}$ is separately an alkyl chain derivatized with charged groups to enhance water solubility or with reactive groups for conjugation to other molecules.

16. The antibody of claim 15 wherein the fluorescent compound has the formula:

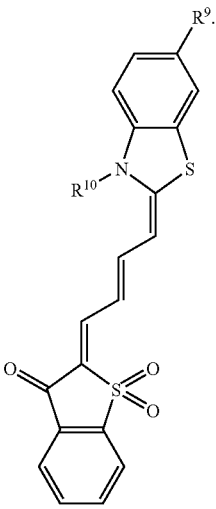

17. The antibody of claim 15 wherein the fluorescent compound has the formula:

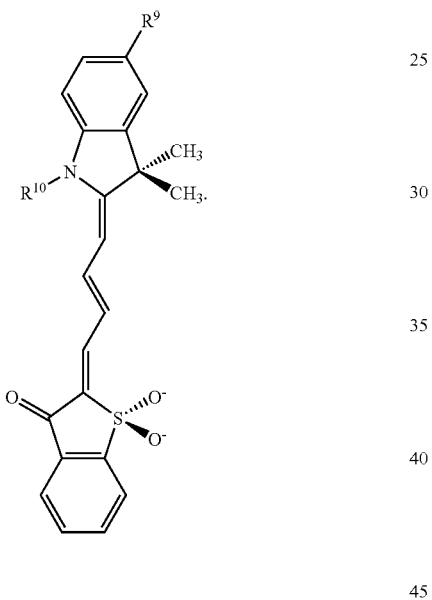

18. The antibody of claim 15 wherein the fluorescent compound has the formula:

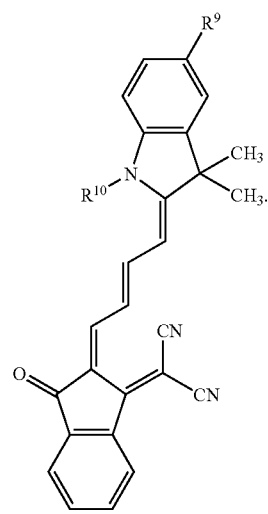

* * * * *

UNITED STATES PATENT AND TRADEMARK OFFICE
CERTIFICATE OF CORRECTION

PATENT NO. : 7,662,644 B2 Page 1 of 1
APPLICATION NO. : 11/673909
DATED : February 16, 2010
INVENTOR(S) : Hahn et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 272 days.

Signed and Sealed this

Thirtieth Day of November, 2010

David J. Kappos
*Director of the United States Patent and Trademark Office*

SEQUENCE LISTING

<160> NUMBER OF SEQ ID NOS: 26

<210> SEQ ID NO 1
<211> LENGTH: 44
<212> TYPE: PRT
<213> ORGANISM: Homo sapiens

<400> SEQUENCE: 1

Lys Lys Lys Glu Lys Glu Arg Pro Glu Ile Ser Leu Pro Ser Asp Phe
1               5                   10                  15

Glu His Thr Ile His Val Gly Phe Asp Ala Cys Thr Gly Glu Phe Thr
            20                  25                  30

Gly Met Pro Glu Gln Trp Ala Arg Leu Leu Gln Thr
        35                  40

<210> SEQ ID NO 2
<211> LENGTH: 16
<212> TYPE: PRT
<213> ORGANISM: Artificial Sequence
<220> FEATURE:
<223> OTHER INFORMATION: A synthetic peptide.

<400> SEQUENCE: 2

Ala Lys Ala Ala Arg Ala Ala Ala Ala Lys Ala Ala Arg Ala Cys Ala
1               5                   10                  15

<210> SEQ ID NO 3
<211> LENGTH: 6
<212> TYPE: PRT
<213> ORGANISM: Artificial Sequence
<220> FEATURE:
<223> OTHER INFORMATION: A synthetic peptide.
<220> FEATURE:
<221> NAME/KEY: SITE
<222> LOCATION: 3
<223> OTHER INFORMATION: Xaa = SAOD = alpha-Boc-beta[N-(2-
      Chlorobenzyloxycarbonyl)-N-MethylaminooxyAcetyl]-alpha,beta-
      Diaminopropionic Acid [Boc-2-Cl-Z-(SA)Dapa-OH].
<220> FEATURE:
<221> NAME/KEY: SITE
<222> LOCATION: 6
<223> OTHER INFORMATION: Xaa = The C-terminal mercaptopropionyl-leucine
      group generated by cleavage of a peptide from TAMPAL resin.

<400> SEQUENCE: 3

Leu Tyr Xaa Ala Gly Xaa
1               5

<210> SEQ ID NO 4
<211> LENGTH: 5
<212> TYPE: PRT
<213> ORGANISM: Artificial Sequence
<220> FEATURE:
<223> OTHER INFORMATION: A synthetic peptide.

<400> SEQUENCE: 4

```
Cys Arg Ala Asn Lys
  1               5
```

<210> SEQ ID NO 5
<211> LENGTH: 10
<212> TYPE: PRT
<213> ORGANISM: Artificial Sequence
<220> FEATURE:
<223> OTHER INFORMATION: A synthetic peptide.
<220> FEATURE:
<221> NAME/KEY: SITE
<222> LOCATION: 3
<223> OTHER INFORMATION: Xaa = SAOD = alpha-Boc-beta[N-(2-
      Chlorobenzyloxycarbonyl)-N-MethylaminooxyAcetyl]-alpha,beta-
      Diaminopropionic Acid [Boc-2-Cl-Z-(SA)Dapa-OH]

<400> SEQUENCE: 5

```
Leu Tyr Xaa Ala Gly Cys Arg Ala Asn Lys
  1               5                  10
```

<210> SEQ ID NO 6
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 6

```
Cys Glu Tyr Arg Ile Asp Arg Val Arg Leu Phe Val Asp Lys Leu Asp
  1               5                  10                  15

Asn Ile Ala Gln Val Pro Arg Val Gly Ala Ala His His His His His
             20                  25                  30

His
```

<210> SEQ ID NO 7
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 7

```
Cys Glu Tyr Arg Ile Asp Arg Val Arg Leu Phe Val Asp Lys Leu Asp
  1               5                  10                  15

Asn Ile Ala Gln Val Pro Arg Val Gly Ala Ala His His His His His
             20                  25                  30

His
```

<210> SEQ ID NO 8
<211> LENGTH: 28
<212> TYPE: PRT
<213> ORGANISM: Artificial Sequence
<220> FEATURE:
<223> OTHER INFORMATION: A synthetic peptide.
<220> FEATURE:
<221> NAME/KEY: SITE
<222> LOCATION: 1
<223> OTHER INFORMATION: Xaa = SAOD = alpha-Boc-beta[N-(2-
      Chlorobenzyloxycarbonyl)-N-MethylaminooxyAcetyl]-alpha,beta-
      Diaminopropionic Acid [Boc-2-Cl-Z-(SA)Dapa-OH]
<220> FEATURE:
<221> NAME/KEY: SITE
<222> LOCATION: 28
<223> OTHER INFORMATION: Xaa = The C-terminal mercaptopropionyl-leucine
      group generated by cleavage of a peptide from TAMPAL resin.

<400> SEQUENCE: 8

```
Xaa Lys Lys Lys Glu Lys Glu Arg Pro Glu Ile Ser Leu Pro Ser Asp
1               5                   10                  15

Phe Glu His Thr Ile His Val Gly Phe Asp Ala Xaa
            20                  25
```

<210> SEQ ID NO 9
<211> LENGTH: 18
<212> TYPE: PRT
<213> ORGANISM: Homo sapiens

<400> SEQUENCE: 9

```
Cys Thr Gly Glu Phe Thr Gly Met Pro Glu Gln Trp Ala Arg Leu Leu
1               5                   10                  15

Gln Thr
```

<210> SEQ ID NO 10
<211> LENGTH: 10
<212> TYPE: PRT
<213> ORGANISM: Artificial Sequence
<220> FEATURE:
<223> OTHER INFORMATION: A synthetic peptide.
<220> FEATURE:
<221> NAME/KEY: SITE
<222> LOCATION: 3
<223> OTHER INFORMATION: Xaa = SAOD = alpha-Boc-beta[N-(2-
      Chlorobenzyloxycarbonyl)-N-MethylaminooxyAcetyl]-alpha,beta-
      Diaminopropionic Acid [Boc-2-Cl-Z-(SA)Dapa-OH]

<400> SEQUENCE: 10

```
Leu Tyr Xaa Ala Gly Cys Arg Ala Asn Lys
1               5                   10
```

<210> SEQ ID NO 11
<211> LENGTH: 45
<212> TYPE: PRT
<213> ORGANISM: Artificial Sequence
<220> FEATURE:
<223> OTHER INFORMATION: A synthetic peptide.
<220> FEATURE:
<221> NAME/KEY: SITE
<222> LOCATION: 1
<223> OTHER INFORMATION: Xaa = SAOD = alpha-Boc-beta[N-(2-
      Chlorobenzyloxycarbonyl)-N-MethylaminooxyAcetyl]-alpha,beta-
      Diaminopropionic Acid [Boc-2-Cl-Z-(SA)Dapa-OH]

<400> SEQUENCE: 11

```
Xaa Lys Lys Lys Glu Lys Glu Arg Pro Glu Ile Ser Leu Pro Ser Asp
1               5                   10                  15

Phe Glu His Thr Ile His Val Gly Phe Asp Ala Cys Thr Gly Glu Phe
            20                  25                  30

Thr Gly Met Pro Glu Gln Trp Ala Arg Leu Leu Gln Thr
        35                  40                  45
```

<210> SEQ ID NO 12
<211> LENGTH: 38
<212> TYPE: PRT
<213> ORGANISM: Artificial Sequence
<220> FEATURE:
<223> OTHER INFORMATION: A synthetic peptide.
<220> FEATURE:
<221> NAME/KEY: SITE
<222> LOCATION: 3
<223> OTHER INFORMATION: Xaa = SAOD = alpha-Boc-beta[N-(2-
      Chlorobenzyloxycarbonyl)-N-MethylaminooxyAcetyl]-alpha,beta-
      Diaminopropionic Acid [Boc-2-Cl-Z-(SA)Dapa-OH]

<400> SEQUENCE: 12

Leu Tyr Xaa Ala Gly Cys Glu Tyr Arg Ile Asp Arg Val Arg Leu Phe
1               5                   10                  15

Val Asp Lys Leu Asp Asn Ile Ala Gln Val Pro Arg Val Gly Ala Ala
            20                  25                  30

His His His His His His
            35

<210> SEQ ID NO 13
<211> LENGTH: 120
<212> TYPE: PRT
<213> ORGANISM: Homo sapiens

<400> SEQUENCE: 13

Asp Ile Gln Asn Pro Asp Ile Thr Ser Ser Arg Tyr Arg Gly Leu Pro
1               5                   10                  15

Ala Pro Gly Pro Ser Pro Ala Asp Lys Lys Arg Ser Gly Lys Lys Lys
            20                  25                  30

Ile Ser Lys Ala Asp Ile Gly Ala Pro Ser Gly Phe Lys His Val Ser
            35                  40                  45

His Val Gly Trp Asp Pro Gln Asn Gly Phe Asp Val Asn Asn Leu Asp
50                  55                  60

Pro Asp Leu Arg Ser Leu Phe Ser Arg Ala Gly Ile Ser Glu Ala Gln
65                  70                  75                  80

Leu Thr Asp Ala Glu Thr Ser Lys Leu Ile Tyr Asp Phe Ile Glu Asp
                85                  90                  95

Gln Gly Gly Leu Glu Ala Val Arg Gln Glu Met Arg Arg Gln Glu Pro
            100                 105                 110

Leu Pro Pro Pro Pro Pro Ser
            115                 120

<210> SEQ ID NO 14
<211> LENGTH: 502
<212> TYPE: PRT
<213> ORGANISM: Homo sapiens

<400> SEQUENCE: 14

Met Ser Gly Gly Pro Met Gly Gly Arg Pro Gly Gly Arg Gly Ala Pro
1               5                   10                  15

Ala Val Gln Gln Asn Ile Pro Ser Thr Leu Leu Gln Asp His Glu Asn
            20                  25                  30

Gln Arg Leu Phe Glu Met Leu Gly Arg Lys Cys Leu Thr Leu Ala Thr
            35                  40                  45

Ala Val Val Gln Leu Tyr Leu Ala Leu Pro Pro Gly Ala Glu His Trp
50                  55                  60

Thr Lys Glu His Cys Gly Ala Val Cys Phe Val Lys Asp Asn Pro Gln
65                  70                  75                  80

Lys Ser Tyr Phe Ile Arg Leu Tyr Gly Leu Gln Ala Gly Arg Leu Leu
                85                  90                  95

Trp Glu Gln Glu Leu Tyr Ser Gln Leu Val Tyr Ser Thr Pro Thr Pro
            100                 105                 110

Phe Phe His Thr Phe Ala Gly Asp Asp Cys Gln Ala Gly Leu Asn Phe
            115                 120                 125

Ala Asp Glu Asp Glu Ala Gln Ala Phe Arg Ala Leu Val Gln Glu Lys
            130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
            180                 185                 190

Leu Ser Leu Gly Leu Ala Thr Val Asp Ile Gln Asn Pro Asp Ile Thr
        195                 200                 205

Ser Ser Arg Tyr Arg Gly Leu Pro Ala Pro Gly Pro Ser Pro Ala Asp
    210                 215                 220

Lys Lys Arg Ser Gly Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
            260                 265                 270

Arg Ala Gly Ile Ser Glu Ala Gln Leu Thr Asp Ala Glu Thr Ser Lys
        275                 280                 285

Leu Ile Tyr Asp Phe Ile Glu Asp Gln Gly Gly Leu Glu Ala Val Arg
    290                 295                 300

Gln Glu Met Arg Arg Gln Glu Pro Leu Pro Pro Pro Pro Pro Pro Ser
305                 310                 315                 320

Arg Gly Gly Asn Gln Leu Pro Arg Pro Pro Ile Val Gly Gly Asn Lys
                325                 330                 335

Gly Arg Ser Gly Pro Leu Pro Pro Val Pro Leu Gly Ile Ala Pro Pro
            340                 345                 350

Pro Pro Thr Pro Arg Gly Pro Pro Pro Gly Arg Gly Gly Pro Pro
        355                 360                 365

Pro Pro Pro Pro Ala Thr Gly Arg Ser Gly Pro Leu Pro Pro Pro
    370                 375                 380

Pro Pro Gly Ala Gly Gly Pro Pro Met Pro Pro Pro Pro Pro Pro Pro
385                 390                 395                 400

Pro Pro Pro Pro Ser Ser Gly Asn Gly Pro Ala Pro Pro Pro Leu Pro
                405                 410                 415

Pro Ala Leu Val Pro Ala Gly Gly Leu Ala Pro Gly Gly Gly Arg Gly
            420                 425                 430

Ala Leu Leu Asp Gln Ile Arg Gln Gly Ile Gln Leu Asn Lys Thr Pro
        435                 440                 445

Gly Ala Pro Glu Ser Ser Ala Leu Gln Pro Pro Gln Ser Ser Glu
    450                 455                 460

Gly Leu Val Gly Ala Leu Met His Val Met Gln Lys Arg Ser Arg Ala
465                 470                 475                 480

Ile His Ser Ser Asp Glu Gly Glu Asp Gln Ala Gly Asp Glu Asp Glu
                485                 490                 495

Asp Asp Glu Trp Asp Asp
            500

<210> SEQ ID NO 15
<211> LENGTH: 34
<212> TYPE: PRT
<213> ORGANISM: Artificial Sequence
<220> FEATURE:
<223> OTHER INFORMATION: A synthetic peptide.

<400> SEQUENCE: 15

Cys Glu Met Ala Gln Leu Glu Lys Glu Val Gln Ala Leu Glu Ser Glu
1               5                   10                  15

Val Ala Ser Leu Glu Lys Glu Val Gln Ala Leu Glu Lys Glu Val Ala
            20                  25                  30

Gln Arg

<210> SEQ ID NO 16
<211> LENGTH: 33
<212> TYPE: PRT
<213> ORGANISM: Artificial Sequence
<220> FEATURE:
<223> OTHER INFORMATION: A synthetic peptide.

<400> SEQUENCE: 16

Lys Met Ala Gln Leu Lys Lys Val Gln Ala Leu Lys Ser Lys Val
1               5                   10                  15

Ala Ser Leu Lys Lys Lys Val Gln Ala Leu Lys Lys Lys Val Ala Gln
            20                  25                  30

Arg

<210> SEQ ID NO 17
<211> LENGTH: 12
<212> TYPE: PRT
<213> ORGANISM: Artificial Sequence
<220> FEATURE:
<223> OTHER INFORMATION: A synthetic peptide.

<400> SEQUENCE: 17

Tyr Gly Arg Lys Lys Arg Arg Asn Arg Arg Pro
1               5                   10

<210> SEQ ID NO 18
<211> LENGTH: 39
<212> TYPE: DNA
<213> ORGANISM: Artificial Sequence
<220> FEATURE:
<223> OTHER INFORMATION: A synthetic oligonucleotide.

<400> SEQUENCE: 18
gagctgtaca agggaggcat gaagatggcc cagctgaag                          39

<210> SEQ ID NO 19
<211> LENGTH: 34
<212> TYPE: DNA
<213> ORGANISM: Artificial Sequence
<220> FEATURE:
<223> OTHER INFORMATION: A synthetic oligonucleotide.

<400> SEQUENCE: 19
gtcgcggccg ccttatcgct gggccacctt cttc                               34

<210> SEQ ID NO 20
<211> LENGTH: 37
<212> TYPE: DNA
<213> ORGANISM: Artificial Sequence
<220> FEATURE:
<223> OTHER INFORMATION: A synthetic oligonucleotide.

<400> SEQUENCE: 20
gactggatcc gagtccatga agaagatggc tcctgcc                            37

<210> SEQ ID NO 21
<211> LENGTH: 66
<212> TYPE: DNA
<213> ORGANISM: Artificial Sequence
<220> FEATURE:

```
<223> OTHER INFORMATION: A synthetic oligonucleotide.

<400> SEQUENCE: 21
ctgaactttc ttcttgagct gggccatctt acttccgcca ccgttgtttt tggggtttgg    60
cttagg                                                                66

<210> SEQ ID NO 22
<211> LENGTH: 63
<212> TYPE: DNA
<213> ORGANISM: Artificial Sequence
<220> FEATURE:
<223> OTHER INFORMATION: A synthetic oligonucleotide.

<400> SEQUENCE: 22
cacctttttc ttcaagctcg ccactttgct cttgagcgcc tgaactttct tcttgagctg    60
ggc                                                                   63

<210> SEQ ID NO 23
<211> LENGTH: 66
<212> TYPE: DNA
<213> ORGANISM: Artificial Sequence
<220> FEATURE:
<223> OTHER INFORMATION: A synthetic oligonucleotide.

<400> SEQUENCE: 23
ggcctcgagt caacgttgag cgactttctt ttttaaggct tgcaccttttt tcttcaagct    60 cgccac                                                                66

<210> SEQ ID NO 24
<211> LENGTH: 35
<212> TYPE: DNA
<213> ORGANISM: Artificial Sequence
<220> FEATURE:
<223> OTHER INFORMATION: A synthetic oligonucleotide.

<400> SEQUENCE: 24
ctcgatcgct cgagtcaacg ttgagcgact ttctt                                35

<210> SEQ ID NO 25
<211> LENGTH: 20
<212> TYPE: DNA
<213> ORGANISM: Artificial Sequence
<220> FEATURE:
<223> OTHER INFORMATION: A synthetic oligonucleotide.

<400> SEQUENCE: 25
ggggatcctc tcagacgccg                                                 20

<210> SEQ ID NO 26
<211> LENGTH: 38
<212> TYPE: DNA
<213> ORGANISM: Artificial Sequence
<220> FEATURE:
<223> OTHER INFORMATION: A synthetic oligonucleotide.

<400> SEQUENCE: 26
catgccatgg ctccggatcc accagctgtg agagacac                             38
```